United States Patent
Scheideler et al.

(10) Patent No.: US 9,320,756 B2
(45) Date of Patent: Apr. 26, 2016

(54) UCP1 (THERMOGENIN)—INDUCING AGENTS FOR USE IN THE TREATMENT OF A DISORDER OF THE ENERGY HOMEOSTASIS

(75) Inventors: Marcel Scheideler, Graz (AT); Michael Karbiener, Graz (AT); Ez-Zoubir Amri, Nice (FR); Gérard Ailhaud, Gonfaron (FR); Christian Dani, Nice (FR)

(73) Assignees: Centre National de la Recherche Scientifique, Paris (FR); l'Université Nice Sophia Antipolis, Nice (FR)

( * ) Notice: Subject to any disclaimer, the term of this patent is extended or adjusted under 35 U.S.C. 154(b) by 409 days.

(21) Appl. No.: 13/696,406

(22) PCT Filed: May 6, 2011

(86) PCT No.: PCT/EP2011/057361
§ 371 (c)(1),
(2), (4) Date: Aug. 28, 2013

(87) PCT Pub. No.: WO2011/138457
PCT Pub. Date: Nov. 10, 2011

(65) Prior Publication Data
US 2013/0331440 A1 Dec. 12, 2013

(30) Foreign Application Priority Data
May 7, 2010 (EP) .................................... 10162363

(51) Int. Cl.
| | | |
|---|---|---|
| *A61K 48/00* | (2006.01) | |
| *C07H 21/02* | (2006.01) | |
| *C07H 21/04* | (2006.01) | |
| *A61K 31/7105* | (2006.01) | |
| *C12N 15/113* | (2010.01) | |
| *A61K 31/7088* | (2006.01) | |
| *A61K 45/06* | (2006.01) | |

(52) U.S. Cl.
CPC ......... *A61K 31/7105* (2013.01); *A61K 31/7088* (2013.01); *A61K 45/06* (2013.01); *C12N 15/113* (2013.01); *C12N 2310/113* (2013.01); *C12N 2310/141* (2013.01)

(58) Field of Classification Search
CPC .............................. A61K 48/00; C12N 15/113
See application file for complete search history.

(56) References Cited

FOREIGN PATENT DOCUMENTS

| WO | WO 2005/013901 | 2/2005 |
| WO | WO 2008/036765 | 3/2008 |

OTHER PUBLICATIONS

Cannon and Nedergaard, "Brown adipose tissue: function and physiological significance", *Physiol Rev.*, 84: 277-359, 2004.
del Mar Gonzalez-Barroso et al., "Transcriptional activation of the human ucp1 gene in a rodent cell line. Synergism of retinoids, isoproterenol, and thiazolidinedione is mediated by a multipartite response element", *JBC*, 275: 31722-32, 2000.
Elabd et al. "Human multipotent adipose-derived stem cells differentiate into functional brown adipocytes." *Stem Cells.*, 27(11):2753-60, 2009.
Feldmann et al., "UCP1 ablation induces obesity and abolishes diet-induced thermogenesis in mice exempt from thermal stress by living at thermoneutrality", *Cell Metab.*, 9: 203-209, 2009.
Hallberg et al., "A functional interaction between RIP140 and PGC-1alpha regulates the expression of the lipid droplet protein CIDEA", *Mol Cell Biol.*, 28: 6785-6795, 2008.
Kim et al. "Integrative genome analysis reveals an oncomir/oncogene cluster regulating glioblastoma survivorship." *Proc Natl Acad Sci U S A.*,107(5):2183-8, 2010.
Ortega et al. "MiRNA expression profile of human subcutaneous adipose and during adipocyte differentiation." *PLoS One.*, 5(2):e9022, 2010.
PCT International Preliminary Report on Patentability, issued in International Application No. PCT.EP2011/057361, dated Nov. 22, 2012.
PCT International Search Report and Written Opinion, issued in International Application No. PCT.EP2011/057361, dated Dec. 9, 2011.
Powelka et al., "Suppression of oxidative metabolism and mitochondrial biogenesis by the transcriptional corepressor RIP140 in mouse adipocytes", *J Clin Invest.*, 116: 125-136, 2006.
Singh et al., "Autophagy regulates lipid metabolism", *JCI*, 458(7242): 1131-1135, 2009.
Spalding et al., "Dynamics of fat cell turnover in humans", *Nature*, 453: 783-787, 2008.
Um et al., "Absence of S6K1 protects against age- and diet-induced obesity while enhancing insulin sensitivity", *Nature*, 431: 200-205, 2004.
Xie et al., "Targeting microRNAs in obesity", *Expert Opin Ther Targets*, 13: 1227-1238, 2009.
Zhang et al., "Adipose-specific deletion of autophagy-related gene 7 (atg7) in mice reveals a role in adipogenesis", *PNAS*, 106(47):19860-19865, 2009.
Bartel, "MicroRNAs: target recognition and regulatory functions," *Cell*, 136:215-233, 2009.
Karbiener et al., "MicroRNA-26 family is required for human adipogenesis and drives characteristics of brown adipocytes," *Stem Cells*, 32:1578-1590, 2014.
Lewis et al., "Conserved seed pairing, often flanked by adenosines, indicates that thousands of human genes are microRNA targets," *Cell*, 120:15-20, 2005.
Pasquinelli et al., "Conservation of the sequence and temporal expression of let-7 heterochronic regulatory RNA," *Nature*, 408:86-89, 2000.

*Primary Examiner* — Amy Bowman
(74) *Attorney, Agent, or Firm* — Parker Highlander PLLC

(57) ABSTRACT

The present invention relates to compositions comprising an agent, like a polynucleotide, which induces or upregulates expression of UCP1 for use in treating or preventing a disorder of the energy homeostasis, overweight, adiposity, obesity, metabolic syndrome or related diseases or disorders in a subject. The present invention also relates to a method of treating or preventing a disorder of the energy homeostasis, overweight, adiposity, obesity, metabolic syndrome or related diseases or disorders in a subject comprising administrating a composition comprising a polynucleotide which induces or upregulates expression of UCP1.

13 Claims, 12 Drawing Sheets

A

B

FIGS. 5A-C

A

Figure 1:
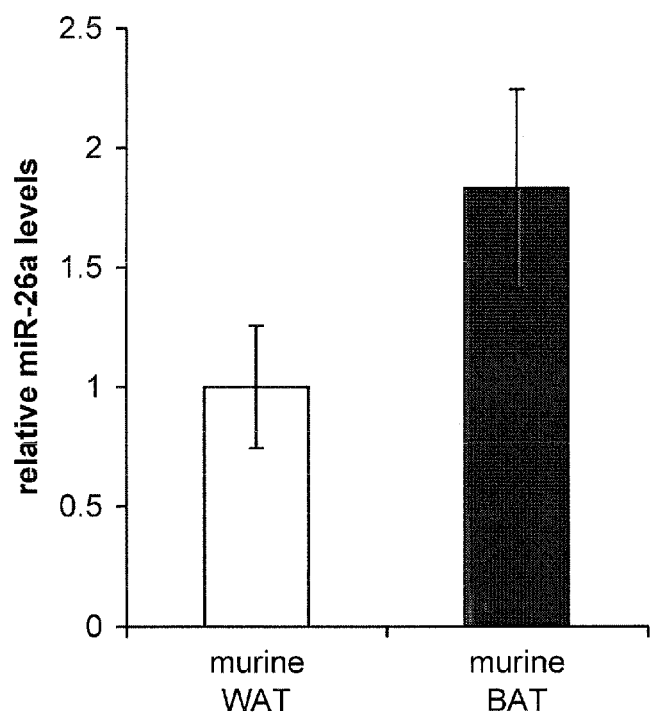

|  | predicted consequential pairing of target region (top) and miRNA (bottom) |  |
|---|---|---|
| position 815-821 of RB1 3' UTR | 5'   ...AAACUACCCAUCUAGUACUUGAA... | (SEQ ID NO: 59) |
| hsa-miR-26a | 3'   UCCCAUAGCACCUAAUGAACUU | (SEQ ID NO: 60) |

B

```
              600       810       820
Hsa  --UGAAUUUAUAAAGUACCCAUCU-AGUACUUGAA--AAAGUAA   (SEQ ID NO: 61)
Ptr  --UGAAUUUAUAAAGUACCCAUCU-AGUACUUGAA--AAAGUAA   (SEQ ID NO: 62)
Mml  --UGAAUUUAUAAAGUACUCAUCU-AGUACUUGAA--AAAGUAA   (SEQ ID NO: 63)
Mmu  --UGAAUUUAU-AAGUACCCAUGU-AGUACUUGAA--AGUCAAG   (SEQ ID NO: 64)
Rno  --UGAAUCUUU-AAGUACCCAUGU-AGUACUUGAA--AAUCAAG   (SEQ ID NO: 65)
Cpo  --UGAAUUUAU-AAGUACCCAUCU-AGUACUUGAA--AAACUAA   (SEQ ID NO: 66)
Sar  --UGAAUUAAUAAACUACCCACCU-AGUACUUGAA--AGC-UAA   (SEQ ID NO: 67)
```

C

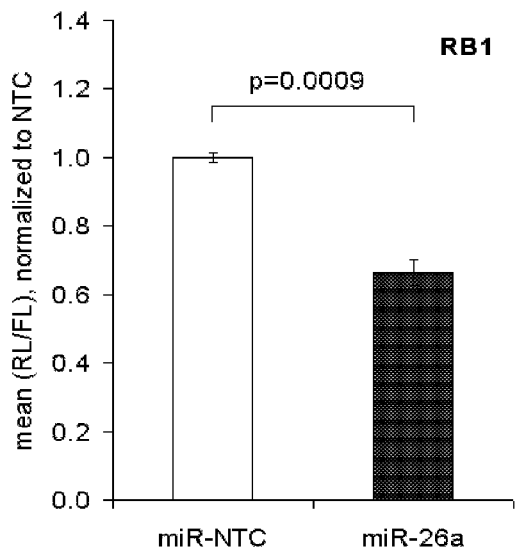

FIGS. 6A-C

A

|  | predicted consequential pairing of target region (top) and miRNA (bottom) |  |
|---|---|---|
| position 1841-1847 of NRIP1 3' UTR | 5' ...GAUUUAAAAUUGUUCUACUUGAA... | (SEQ ID NO: 68) |
| hsa-miR-26a | 3' UCGGAUAGGACCUAAUGAACUU | (SEQ ID NO: 60) |

B

```
            .........1820......1830......1840.........1850
Hsa  CUAGUU---AGGAUAUUGAUUUAAAAUUGUUCUAC----UUGAAGUGGU  (SEQ ID NO: 69)
Ptr  CUAGUUAGAAGGAUAUUGAUUUAAAAUUGUUCUAC----UUGAAGUGGU  (SEQ ID NO: 70)
Mml  CUAGUUAGAAGGAUAUUGAUUUAAAGUUGUUCUUC----UUGAAGUGGU  (SEQ ID NO: 71)
Mmu  UUAAGUAGGAAGAAGUUUAUUUGGAAUUGUUAUACAUACUUGAAGUUGU  (SEQ ID NO: 72)
Rno  UUACGUAGGAAGAAGCUUAUUUGAAGUUGUCGUACGUACUUGAAGUUGU  (SEQ ID NO: 73)
Cpo  UUAAUUAGAAGGCAAUUAAUUUGAAGUUGCUCUAC----UUGAAGUUGU  (SEQ ID NO: 74)
Sar  UCAAUUAGGAGGAAAUGUAUUUGAAGUU---CUAC----UUGAAGCUGU  (SEQ ID NO: 75)
```

C

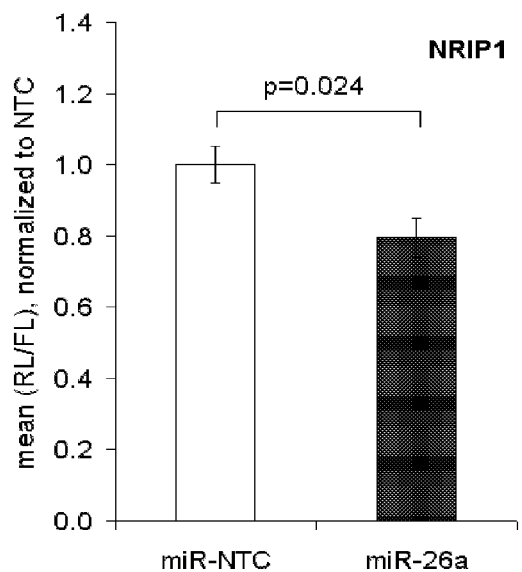

FIGS. 7A-B
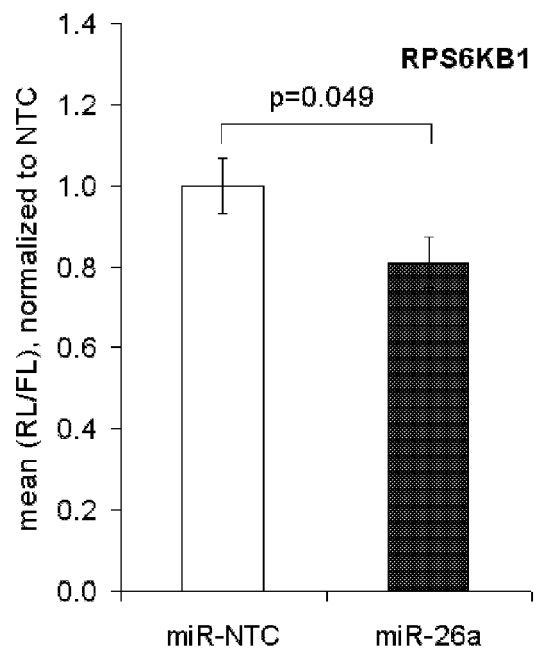

```
hsa-miR-26a      3'    UCGGAUAGGACCUAAUGAACUU    5'   (SEQ ID NO: 60)
hsa-miR-26b      3'     UGGAUAGGACUUAAUGAACUU    5'   (SEQ ID NO: 77)
hsa-miR-1297     3'         GUGGACUUAAUGAACUU    5'   (SEQ ID NO: 78)
```

UCP1 (THERMOGENIN)—INDUCING AGENTS FOR USE IN THE TREATMENT OF A DISORDER OF THE ENERGY HOMEOSTASIS

CROSS-REFERENCE TO RELATED APPLICATION

This application is a national phase application under 35 U.S.C. §371 of International Application No. PCT/EP2011/057361, filed on May 6, 2011 which claims priority to European Patent Application No. 10162363.5 filed on May 7, 2010 the entire contents and disclosures of which are specifically incorporated by reference herein without disclaimer.

The present invention relates to agents that are capable of inducing and/or up-regulating the expression of UCP1 ("uncoupling protein 1", also known as thermogenin) for use in treating or preventing a disorder of the energy homeostasis such as obesity, overweight, adiposity, metabolic syndrome, or diseases or disorders related to energy homeostasis disorders such as diabetes (e.g., diabetes type II), hypercholesterolemia or hypertension. The present invention also relates to a method of treating or preventing a disorder of the energy homeostasis such as obesity, overweight, adiposity, metabolic syndrome, or diseases or disorders related to energy homeostasis disorders such as diabetes (e.g., diabetes type II), hypercholesterolemia or hypertension in a subject comprising administrating a composition comprising a polynucleotide which induces or upregulates expression of UCP1.

Obesity has emerged as a global health problem with more than 1.1 billion adults to be classified as overweight or obese (Oh, Curr Top Med Chem (2009), 9: 466-481). Overweight and obesity are the consequence of a disproportionate fat mass relative to height. This situation then leads to various metabolic disturbances (such as insulin resistance, type 2 diabetes, high blood pressure, dyslipidemia and the like) and is now considered as a major health issue. Unfortunately, obesity treatment is so far not satisfactory.

Overall, fat accumulation in white adipose tissue (WAT) through hyperplasia and/or hypertrophy of white fat cells is the normal physiological response to an excess of energy intake over energy expenditure. Therefore, decreasing intake or increasing expenditure represents pharmacologically the ultimate goal. So far, all pharmacological approaches aimed at controlling energy intake by lowering either intestinal absorption of nutrients—mainly lipids—or increasing satiety via the central nervous system (Oh, Curr Top Med Chem (2009), 9: 466-481). Without change in energy intake, preventing the formation of white fat cells is a scientific nonsense as caloric excess is then recovered as triglycerides in liver (steatosis) and in skeletal muscles, leading in turn to insulin resistance and diabetes, as illustrated in mice and humans suffering from lipoatrophy (Moitra, Genes Dev (1998), 12: 3168-3181).

With respect to energy expenditure, the major types of energy utilization are physical activity and thermogenesis. The part devoted to physical activity is highly variable and depends entirely upon individual life style, being rather unimpressive at the population level. With respect to thermogenesis, most importantly, as a proof of principle, mild uncoupling of oxidative phosphorylation known to increase energy expenditure in humans, i.e. with 300 mg Dinitrophenol per day, led to body weight loss of 0.5-1 kg/week (Cutting, J Clin Invest (1934), 13: 547-552).

Therefore, owing to new data obtained in the last couple of years, increasing energy expenditure should now be reconsidered for two reasons: (i) brown adipose tissue (BAT) has been known in rodents to dissipate caloric excess through diet-induced thermogenesis, and (ii) in contrast to early contention, healthy adult individuals possess active BAT in small quantities localized in various sites (supraclavicular, neck, perivertebral) with a potential of metabolic significance. Its activity, measured by $^{18}$F-fluorodeoxyglucose uptake, appears inversely proportional to WAT mass (Nedergaard, Am J Physiol Endocrinol Metab (2007), 293: E444-E452; Zingaretti, FASEB J (2009), 23: 3113-3120; As-Yong, Diabetes (2009), 58: 2583-2587; Manieri, Nutr Metab Cardiovasc Dis (2009), PMID: 19692217; Saito, Diabetes (2009), 58: 1526-1531; Cypess, N Engl J Med (2009), 360: 1509-1517; van Marken, N Engl J Med (2009), 360: 1500-1508; Virtanen, N Engl J Med (2009), 360: 1518-1525). As the most recent data indicate that the absence of BAT-derived thermogenesis may be sufficient to cause obesity in mice and humans, this dramatic conceptual change has emphasized BAT as a new important candidate to control body weight through modulation of energy expenditure.

From a biological view point, the existence of a single precursor cell type giving rise to distinct pools of brown versus white preadipocytes remains unclear (Moulin, Biochem J (2001), 356: 659-664) as brown and white preadipocytes appear "committed" at that stage and only able to differentiate in vitro into brown and white adipocytes, respectively. On one hand, a myogenic signature of brown adipocytes and cell sorting of muscle and WAT progenitors favor a distinct origin from that of white adipocytes (Timmons, Proc Natl Acad Sci USA (2007), 104: 4401-4406; Crisan, Stem Cells (2008), 26: 2425-2433; Walden, J Cell Physiol (2009), 218: 444-449). On the other hand, brown adipocytes could emerge from different origins as BMP7 triggers commitment of murine mesenchymal progenitor cells to a brown adipocyte lineage in vitro and in vivo (Tseng, Nature (2008), 454: 1000-1004; Seale, Nature (2008), 454: 961-967) whereas white adipocytes can be converted to brown adipocytes through transgenesis (Tiraby, J Biol Chem (2003), 178: 33370-33376). However, in contrast to primary and clonal preadipocytes of BAT from various species, no primary or clonal precursor cells of human brown adipocytes have been obtained so far. If existing, such tool could be used to develop therapeutic drugs and to gain further insights into the molecular mechanisms of brown adipogenesis (Cannon, Meth Mol Biol (2001), 155: 213-224).

The Institute of Developmental Biology and Cancer (IDBC, Nice, France) has isolated mesenchymal stem cell populations from human adipose tissue (termed hMADS cells) which exhibit at a clonal level both normal karyotype and high self-renewal ability, and are not tumorigenic; they are able to differentiate into various lineages including white adipocytes and osteoblasts as well as to support in vivo regenerative processes (Rodriguez, Biochem Biophys Res Comm (2004), 315: 255-263; Rodriguez, J Exp Med (2005), 201: 1397-1405; Zaragosi, Stem Cells (2006), 24: 2412-2419; Elabd, Biochem Biophys Res Comm (2007), 361: 342-348; Fontaine, Stem Cells (2008), 26: 1037-1046). Once differentiated into adipocytes, hMADS cells exhibit the molecular and functional properties of human white fat cells that include potent release of adiponectin and leptin as well as responsiveness to insulin, to β-adrenergic receptor (ADRB) agonists and, specific of primates, to atrial natriuretic peptide (Rodriguez, Biochem Biophys Res Comm (2004), 315: 255-263). Thus, the hMADS cell model has represented a unique human cell model to examine whether, in response to appropriate stimuli, conversion to functional brown adipocytes could also take place. It was also shown that, upon chronic exposure to a specific peroxisome proliferator-activated receptor γ (PPARG) but not to a peroxisome proliferator-activated receptor β/δ (PPARB/D) or a peroxisome proliferator-activated receptor α (PPARA) agonist, hMADS cell-derived white adipocytes are able to switch to a functional brown adipocyte phenotype (Elabd, Stem Cells (2009) 27: 2753-2760). Once differentiated, these cells fulfill most key criteria of brown adipocytes by expressing genes encoding uncoupling protein 1 (UCP1), cell death-inducing DFFA-like effector a (CIDEA), peroxisome proliferator-activated receptor gamma, coactivator 1 α (PPARGC1A, PGC1A), peroxisome proliferator-activated receptor gamma, coactivator 1 β (PGC1B), and PR domain containing 16 (PRDM16) as well as key members of the peroxisome proliferator-activated receptor (PPAR) family. Elegant studies in mouse have recently shown both in vitro and in vivo that PRDM16 controls the determination of brown fat fate, i.e. inducing the expression of UCP1 and PGC1A genes, whereas ligand-activated PPARG appears necessary for the expression of CIDEA and mitochondrial components (Seale, Cell Metab (2007), 6: 38-54). However, expression of PRDM16 was not specific to the brown fat cell phenotype in humans (Elabd, Stem Cells (2009) 27: 2753-2760).

Importantly, hMADS cell derived brown adipocytes express UCP1 protein and are metabolically active as the acquisition of a brown fat cell phenotype is accompanied by a dramatic increase in respiratory activity and uncoupled respiration. When shifting from a white to a brown fat cell phenotype, this striking enhancement of uncoupling activity appears mainly, if not all, due to an increase in UCP1 expression whereas induction of uncoupling protein 2 (UCP2) is weak and no change in of uncoupling protein 3 (UCP3) expression is observed. The up-regulation of UCP1 expression both by isoproterenol (del Mar Gonzalez-Barroso, JBC (2000), 275: 31722-32; Cannon and Nedergaard, Physiol Rev (2004) 84: 277-359) and CL316 243 (Tocris Bioscience) (Yoshitomi, BBRC (1998), 253: 85-91) indicate that the adrenergic receptor signalling pathway, in particular through $β_3$-adrenergic receptor (ADRB3), is also functional in these cells. In light of the occurrence of functional BAT in adult individuals and of the insurmountable difficulty to obtain enough human BAT to perform biochemical studies on a routine basis, hMADS cells thus represent an invaluable human cell model to screen for drugs able to stimulate the formation and/or the energy-dissipating capacity of brown adipocytes (Elabd, Stem Cells (2009) 27: 2753-2760).

In addition to the expression of PRDM16, PGC and PGC and the expression of C-terminal-binding protein 1 (CTBP1) gene (Kajimura, Genes Dev (2008), 22: 1397-1409), it cannot be excluded that additional molecular event(s) are required for the acquisition of a complete brown fat cell phenotype. A new mechanism of gene regulation has been unravelled over the last decade that is mediated by a class of small non-coding RNAs known as microRNAs (miRNAs). miRNAs act through complementary target sites in mRNAs and prevent translation of transcripts and/or accelerate their decay. In mammals, more than 400 miRNAs well conserved among different species have been identified, among which some exhibit an expression pattern that depends on the developmental stage or on the cell type (Carthew, Cell (2009), 136: 642-655; Krützfeld, Cell Metab (2006), 4: 9-12; Brown, Nat Rev Genet (2009), 10: 578-585; Stenvang, Biochem Soc Trans (2008), 36: 1197-1200; Petri, Cancer Res (2009), 69: 393-395). Most importantly, miRNAs have been shown to modulate adipogenesis (Xie, Expert Opin Ther Targets (2009), 13: 1227-1238), to be expressed in human abdominal and subcutaneous WAT (Klöting, PLoS ONE (2009), 4: e4699), and to circulate in blood as stable compounds (Gilad, PLoS ONE (2008), 3: e3148). In addition, miRNAs can be differentially expressed between white and brown adipocytes, as shown for miR-455 in mouse (Walden, loc cit).

However, mechanisms involved in the formation and differentiation of adipocytes are still poorly understood. Without such knowledge, directed search for and identification of compounds influencing these mechanisms is hardly possible. Compounds leading to increased mass/activity of BAT would be of great interest for the treatment of diseases or disorders associated with adipocyte formation and differentiation.

This technical problem has been solved by the embodiments provided herein and the solutions provided in the claims.

Accordingly, the present invention provides for agents and compounds that are capable of inducing and/or up-regulating the expression and/or biological activity of UCP1 ("uncoupling protein 1", also known as thermogenin). Particularly useful in this context are agents, like the herein provided microRNAs, that are capable of negatively interfering with the expression of UCP1 suppressors and/or inhibitors (suppressors) of the UCP1-promoting insulin signalling pathway. In particular, composition is provided herein that comprises (a) polynucleotide(s) which induce(s) or upregulate(s) the biological function of UCP1 and/or is/are capable of inducing or upregulating the expression of UCP1. Said composition is useful in the medical intervention of disorders and diseases related to mal-controlling or malfunctioning of energy homeostasis, like in the treatment and/or the prevention of obesity, overweight, adiposity, metabolic syndrome, or diseases or disorders related to energy homeostasis disorders such as diabetes (e.g., diabetes type II), hypercholesterolemia or hypertension. As documented herein, particular useful agents in this respect are polynucleotides comprising or consisting of the nucleotide sequence of any one of SEQ ID NO: 1 (miR-26a), SEQ ID NO: 2 (miR-26b), SEQ ID NO: 3 (miR-1297), or SEQ ID NO: 6 (seed sequence of SEQ ID NOs. 1 to 3). In context of this invention, it could be shown that specific miRs/microRNAs are capable of inducing or up-regulating the expression or biological function of UCP1. These agents are of particular interest since they target more than one UCP1-suppressors as defined herein and, thus, these agents elevate UCP1 expression. It was surprisingly found and it is documented herein below and in the appended Examples and Figures that some of the herein disclosed miRNAs are capable of inhibiting the expression of at least two or even at least three UCP1 suppressors and/or suppressors of the UCP1-promoting insulin signalling pathway. This is for example illustrated for SEQ ID NO: 1 (miR-26a) which interferes with retinoblastoma 1 (RB1; NCBI Reference Sequence: NM_000321.2), nuclear receptor interacting protein 1 (NRIP1, also known as RIP140, NCBI Reference Sequence: NM_003489.3) and ribosomal protein S6 kinase, 70 kDa, polypeptide 1 (RPS6KB1, also known as S6K1, NCBI Reference Sequence: NM_003161.2). Therefore, SEQ ID NO: 1 (miR-26a), inter alia, and related polynucleotides target the corresponding mRNA of RB1, NR1P1 and RPS6KB1 as described herein. These targets are shown herein to be concomitantly and independently down-expressed by the agents described herein.

It was found that the agents provided herein are not only able to induce differentiation of adipocyte precursor cells into thermogenic adipocytes. Moreover, the compositions and agents of this invention are able to induce transdifferentiation from white (UCP1-negative) to thermogenic (UCP1-positive) adipocytes; exemplarily shown in Example 4 and FIG. 4. Without being bound by theory, transdifferentiation is a process by which a differentiated (non-stem) cell converts into another type of differentiated cell without being reprogrammed or de-differentiated into a stem cell, e.g., transdifferentiation from a white to a brown adipocyte (e.g., PMID: 20354155), from a muscle to brown adipocyte (e.g., PMID: 19641492), and from secretory epithelial cells to white adipocytes (e.g., PMID: 15556998). Accordingly, the agents (e.g., polynucleotides) described herein are capable of inducing transdifferentiation from white (UCP1-negative) to thermogenic (UCP1-positive) adipocytes. Such agents may be polynucleotides which comprise the common seed sequence of miR-26a, miR-26b and miR-1297 as represented in SEQ ID NO: 6 (cf. FIG. 8).

The present invention relates to a composition comprising an agent which induces or upregulates expression of UCP1 and which negatively interferes concomitantly and independently with at least two UCP1 suppressors and/or suppressors of the UCP1-promoting insulin signalling pathway for use in treating or preventing disorders of the energy homeostasis such as obesity, overweight, adiposity, metabolic syndrome, or diseases or disorders related to energy homeostasis disorders such as diabetes (e.g., diabetes type II), hypercholesterolemia or hypertension in a subject. Also provided is a method of treating or preventing disorders of the energy homeostasis such as obesity, overweight, adiposity, metabolic syndrome, or diseases or disorders related to energy homeostasis disorders such as diabetes (e.g., diabetes type II), hypercholesterolemia or hypertension in a subject, said method comprising administering an effective amount of a composition comprising an agent which induces or up-regulates expression of UCP1 and which negatively interferes concomitantly and independently with at least two UCP1 suppressors and/or suppressors of the UCP1-promoting insulin signalling pathway. Generally, as used herein, the term "concomitantly and independently" means that agents such as polynucleotides to be employed in context of the present invention may negatively interfere or interact with at least two, or at least three UCP1-suppressors and/or suppressors of the UCP1-promoting insulin signalling pathway at the same time and independently from each other in vivo.

The agents described herein may be capable of inducing transdifferentiation from white (UCP1-negative) to thermogenic (UCP1-positive) adipocytes, thus effectively transforming, in a subject administered the composition comprising the agent, existing energy storing adipose tissue (WAT) into thermogenic (UCP1-positive), energy dissipating adipose tissue (BAT). This treatment has advantages over a treatment which only induces de novo differentiation of precursor cells into thermogenic (UCP1-positive) adipocytes, but does not address pre-existing white (UCP1-negative) adipocytes.

In a preferred embodiment of the present invention, the agent to be used in the inventive composition and method is a polynucleotide. Said polynucleotide hybridizes preferably to the mRNA of a UCP1-suppressor and/or the mRNA of a suppressor of the UCP1-promoting insulin signalling pathway, thereby inducing degradation or preventing translation of said mRNAs and thereby inhibits the expression of at least two or even at least three UCP1 suppressors and/or suppressors of the UCP1-promoting insulin signalling pathway. Said polynucleotide may be a microRNA, a precursor of a microRNA, or a mimic microRNA or a precursor thereof.

Figure 2:
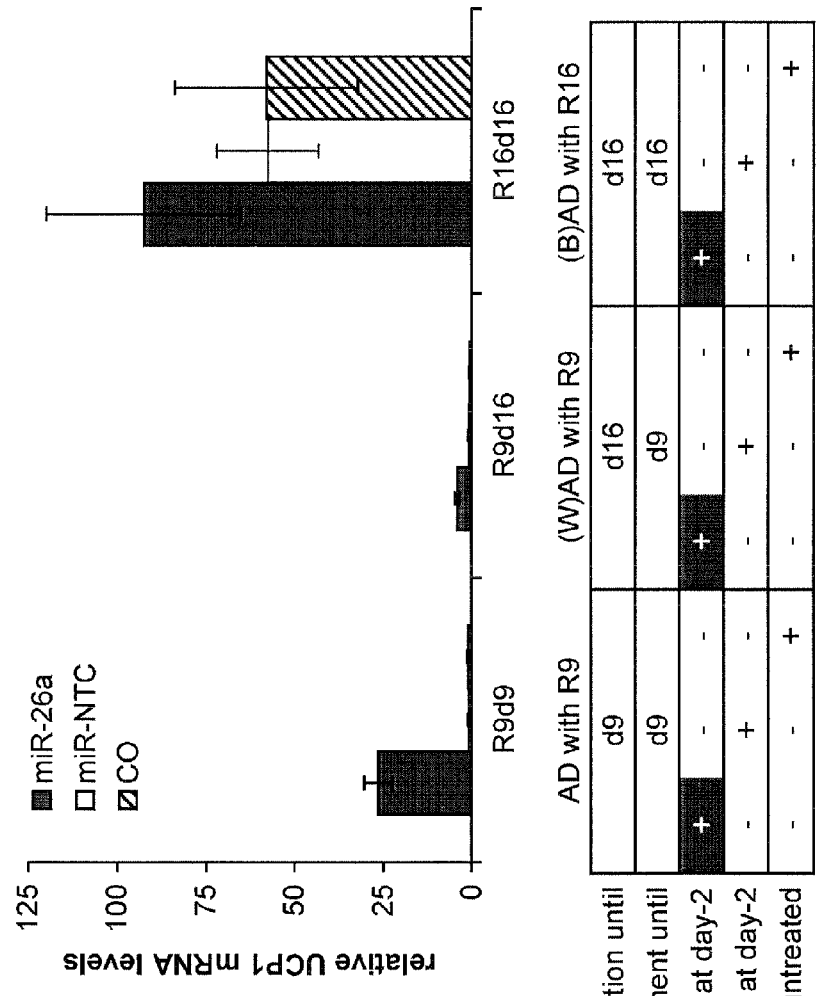
Figure 2:
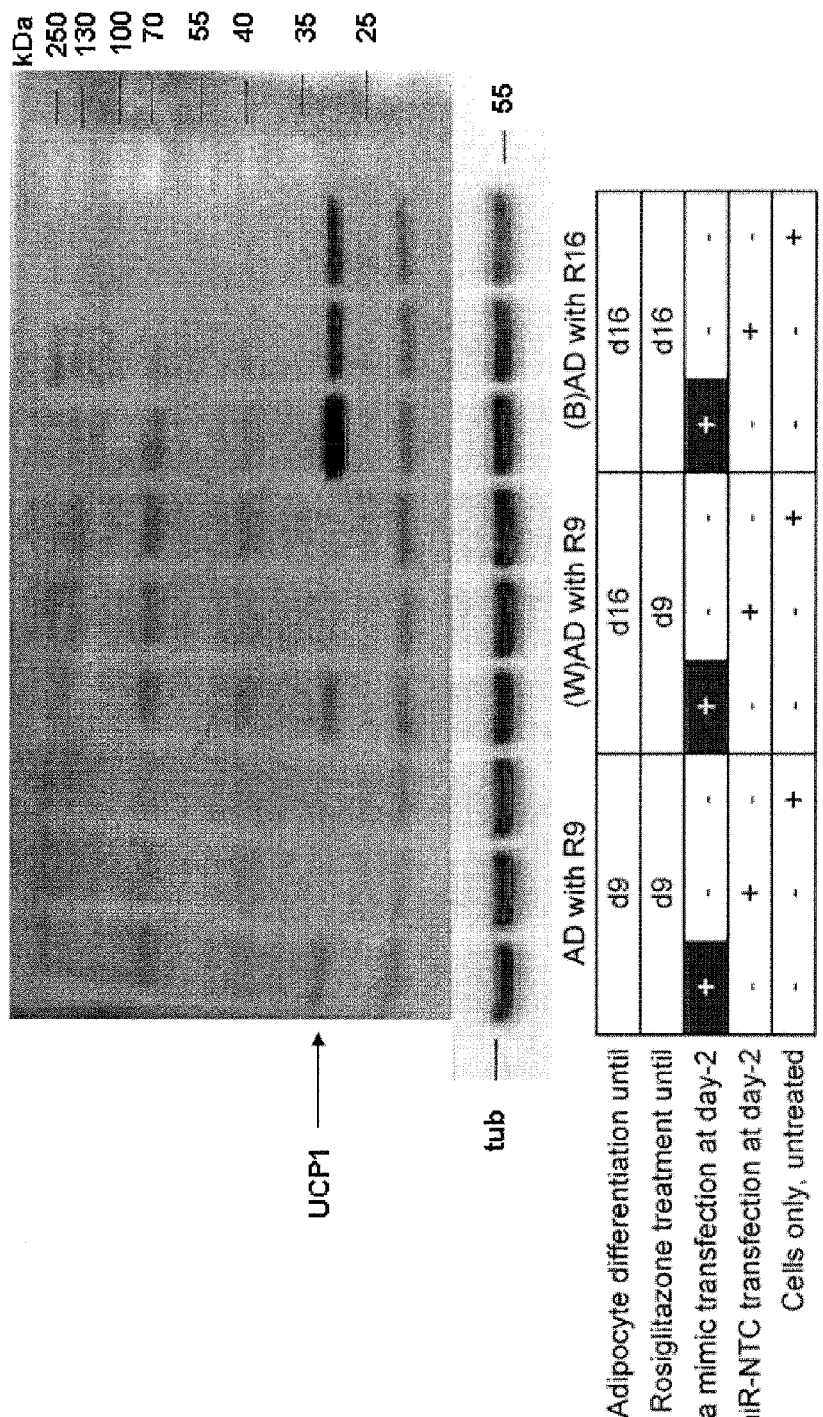
Figure 3:
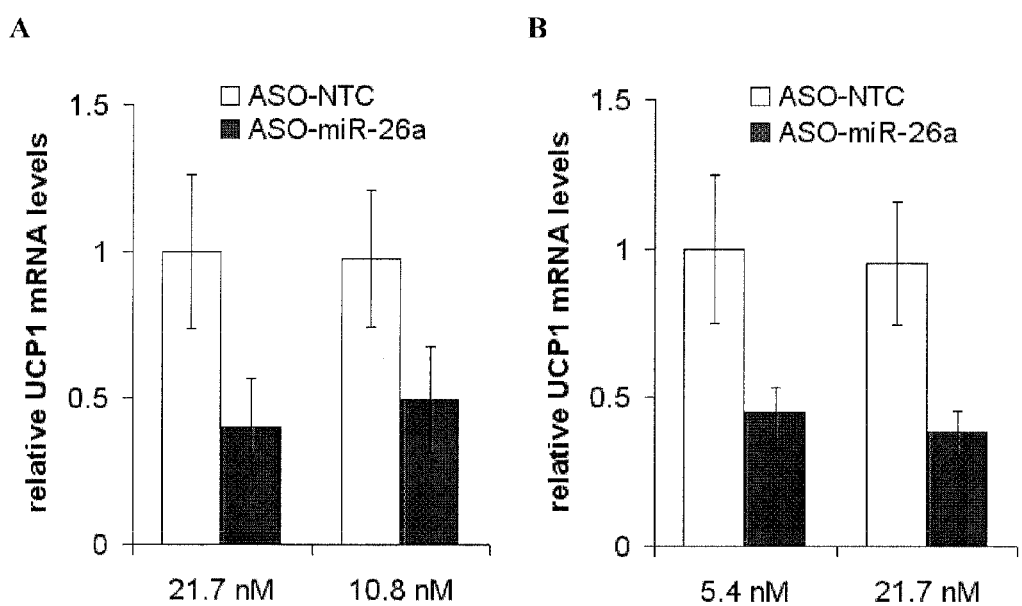
Figure 4:
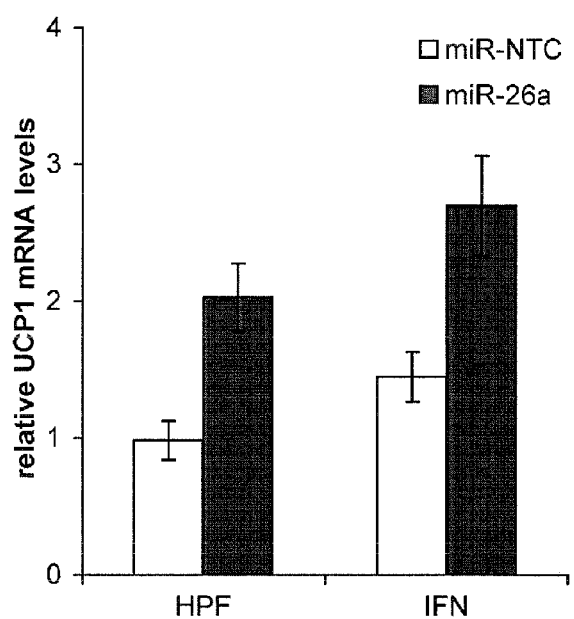

The present invention also provides for the identification and validation of modifying nucleic acid molecules/polynucleotides, in particular of microRNAs, mimic microRNAs or (a) precursor(s) of such nucleic acid molecules/polynucleotides in the process of brown adipocyte differentiation and conversion from white to brown adipocytes. Therefore, the present invention also provides for modifying nucleic acid molecules/polynucleotides, in particular microRNAs, mimic microRNAs or (a) precursor(s) of such nucleic acid molecules/polynucleotides that are capable of trans-differentiating white adipocytes to thermogenic adipocytes, which are named brown if localized in brown adipose tissue (BAT) or brite if localized in white adipose tissue (WAT). However, in context of the present invention, also other agents (that are specifically capable of up-regulating or inducing UCP1) are envisaged in the medical intervention of energy homestasis-disorders. Such agents may comprise, but are not limited to siRNAs, long non-coding RNAs, snRNAs (small/short hairpin RNAs), stRNAs (small temporal RNAs), fRNAs (functional RNAs), snRNAs (small nuclear RNAs), snoRNAs (small nucleolar RNAs), piRNAs (piwi-interacting RNAs), tasiRNAs (trans-acting small/short interfering RNAs), aRNAs (antisense RNAs) or (a) precursor(s) of such nucleic acid molecules/polynucleotides The compounds and agents of the present invention are, accordingly, useful in the process of brown adipocyte differentiation and conversion from white to brown adipocytes. The findings documented herein and the present invention are based on the following technical teaching:

Expression of an exemplified modifying nucleic acid molecule/polynucleotide (microRNA-26a; miR-26a) in murine brown adipose tissue is about 80% higher than in white adipose tissue as, e.g., measured by qRT-PCR; see also FIG. 1 appended hereto;

Switch from white to brown adipocyte differentiation is mediated by an exemplified modifying nucleic acid molecule/polynucleotide:

(a) miR-26a overexpression in undifferentiated hMADS cells followed by adipogenic stimulation to white adipocytes results in an important expression of UCP1 on mRNA level and on protein level which indicates a switch from white to brown adipogenesis into human mesenchymal stem cells; illustrated in appended FIG. 2;

(b) miR-26a inhibition in undifferentiated hMADS cells followed by adipogenic stimulation results in reduced UCP1 expression, further emphasizing that UCP1 is under the control of miR-26a; see appended FIG. 3;

Conversion from white to brown adipocytes is mediated by an exemplified modifying nucleic acid molecule/polynucleotide:

miR-26a overexpression in hMADS adipocytes increases the expression of UCP1 indicating a conversion from white to brown adipocytes; see appended FIG. 4.

Without being bound by theory, the mechanism by which the exemplified modifying agents, in particular nucleic acid molecules/polynucleotides (exemplified by miR-26a), mediate the desired. UCP1 induction may be illustrated by the following:

(a) RB1 (retinoblastoma protein, pRb, also known from Dali-Youcef, PNAS (2007), 104: 10703-10708) is a suppressor of mitochondrial biogenesis and UCP1 expression in white adipocytes by targeting the UCP1 activator PGC1A (Hansen, PNAS (2004), 101: 4112-4117). In context with the present invention, we have identified RB1 to be a direct target of miR-26a, and luciferase reporter assays demonstrated herein and in accordance with the present invention show that miR-26a indeed directly binds to the RB1 3'UTR and thereby represses RB1 expression; see appended FIG. 5;

(b) NRIP1 is also a known repressor of UCP1 expression in white adipocytes (Leonardsson, PNAS (2004), 101: 8437-8442). In context with the present invention, we have identified NRIP1 to be a direct target of miR-26a, and luciferase reporter assays demonstrated herein and in accordance with the present invention show that miR-26a indeed directly binds to the NRIP1 3'UTR and thereby represses NRIP1 expression; illustrated in appended. FIG. 6;

(c) RPS6KB1 is a mediator of obesity and insulin resistance. Furthermore, RPS6KB1 knockout mice show UCP1 expression in WAT (Um, Nature (2004), 431: 200-205). In context with the present invention, we have identified RPS6KB1 to be a direct target of miR-26a, and luciferase reporter assays demonstrated herein and in accordance with the present invention show that miR-26a indeed directly binds to the RPS6KB1 3'UTR and thereby represses RPS6KB1 expression; see appended FIG. 7.

Therefore, in accordance with this invention, it was surprisingly be found that certain compounds, like nucleic acid molecules/polynucleotides, in particular microRNAs, mimic microRNAs or (a) precursor(s) of such nucleic acid molecules/polynucleotides are capable of interfering with at least two UCP1 suppressors and/or inhibitors of the UCP1-promoting insulin signalling pathway and thereby efficiently induce and/or up-regulate the expression and biological function of UCP1. In particular embodiments of this invention, such compounds are even capable of interfering with at least three UCP1 suppressors and/or inhibitors/suppressors of the UCP1-promoting insulin signalling pathway, like RB1 (NCBI Reference Sequence: NM_000321.2), NRIP1 (NCBI Reference Sequence: NM_003489.3) and RPS6KB1 (NCBI Reference Sequence: NM_003161.2).

miR-26a (SEQ ID NO: 1), miR-26b (SEQ ID NO: 2), and miR-1297 (SEQ ID NO: 3) are examples of such interfering nucleic acid molecules and these sequences share the same seed sequence (as illustrated in appended FIG. 8 and SEQ ID NO: 6) and a high overall sequence homology. Therefore, the latter two are envisaged to bind to the same validated miR-26a binding sites in the 3'UTRs of RB1, NRIP1, and RPS6KB1, and thus can also be able to induce UCP1 expression. In a further embodiment, the interfering nucleic acid molecule for at least two UCP1 suppressors of the present invention is a molecule, like a miR/microRNA, that comprises the sequence as shown in SEQ ID NO: 6, i.e. the sequence UCAAGU. Particular examples of such sequences are miR-26a (SEQ ID NO: 1), miR-26b (SEQ ID NO: 2), and miR-1297 (SEQ ID NO: 3). However, and in accordance with this invention, also other interfering sequences that comprise the sequence UCAAGU (SEQ ID NO: 6) may by employed.

As documented herein below and in the appended examples, a set of miRNAs are differentially expressed between white and brown adipocytes of hMADS cells, thereby putative regulators of the conversion between white and brown adipocytes; see appended Table 1. Further miR-NAs which are expressed in brown adipocytes but not in white adipocytes are described in Xie, Expert Opin Ther Targets (2009), 13: 1227-1238. However, an miR/micro RNA that comprises the sequence UCAAGU (SEQ ID NO: 6), like miR-26a (SEQ ID NO: 1), miR-26b (SEQ ID NO: 2), and miR-1297 (SEQ ID NO: 3) appeared in gene expression studies using microarrays not to be differentially expressed between WAT and BAT as well as between white and brown human adipocyte differentiation, as documented in Table 1 below and in Xie, loc cit. Yet, in contrast thereto and only after further detailed analysis by qRT-PCR performed in context of the present invention, expression of, e.g., miR-26a was determined to be about 80% higher in mouse brown adipose tissue compared to mouse white adipose tissue as shown in appended FIG. 1 for exemplarily miR-26a. However, in miRNA profiling using microarrays, it was found that an miR/micro RNA that comprises the sequence UCAAGU (SEQ ID NO: 6), like miR-26a (SEQ ID NO: 1), appeared not to be differentially expressed between WAT and BAT. Furthermore, miR-26 has been described to be expressed to three cell lineages (adipocytes, chondrocytes and osteoblasts), thus not playing a role in cell fate determination and lineage differentiation (Xie, Diabetes (2009), 58: 1050-1057).

Yet, it was found in context of this invention that a polynucleotide molecule that comprises the sequence UCAAGU (SEQ ID NO: 6) like miR-26a (i) is expressed at higher levels in murine BAT compared to murine WAT (FIG. 1), (ii) is able to induce undifferentiated hMADS cells to differentiate into brown adipocytes as indicated by increased UCP1 expression when added to the differentiation medium for white adipocytes (FIGS. 2A and 2B), (iii) silencing leads to down-regulation of UCP1 expression (FIG. 3), (iv) is able to transdifferentiate/convert mature hMADS white adipocytes to a brown phenotype as indicated by increased UCP1 expression when transfected into mature hMADS white adipocytes (FIG. 4), (v) is documented herein to directly target and thereby inhibit the UCP1 suppressors such as RB1, NRIP1, and the inhibitor (suppressor) of the UCP1-promoting insulin signalling pathway RPS6KB1 (FIGS. 5A, 6A, and 7A). It could be shown in accordance with this invention that such an miRNA indeed directly binds to the 3'UTRs of RB1 and NRIP1, both known repressors of UCP1 expression, and RPS6KB1, a known inhibitor of the UCP1-promoting insulin signalling pathway (FIGS. 5C, 6C and 7B), and moreover, that it (vi) shares its seed sequence with miR-26b and miR-1297 (FIG. 8), thereby indicating that these miRNAs are also able to induce UCP1 expression via repressing RB1, NRIP1 and/or RPS6KB1. In addition, (vii) a number of miRNAs are differentially expressed between white and brown human adipocytes (Table 1) indicating a role in maintaining an energy utilizing "brown" phenotype. Hence, these miRNAs may also be able to regulate the expression of the key target UCP1 and thus to increase energy expenditure in order to combat disorders of energy homeostasis such as obesity, overweight, adiposity, metabolic syndrome, or diseases or disorders related to energy homeostasis disorders such as diabetes diabetes type II), hypercholesterolemia or hypertension. The appended Examples and Figures provide even more data on miR/microRNA that comprises the sequence as shown in SEQ ID NO: 6, i.e. the sequence UCAAGU, in particular the exemplified miR-26a (SEQ ID NO: 1). For example, as described and exemplified herein, expression of polynucleotides as described herein such as miR-26a and, consequently, of UCP1 increases in murine WAT upon cold exposure, while at the same time, expression of UCP1-suppressors and inhibitors (suppressors) of the UCP1-promoting insulin signalling pathway as described herein such as RB1, NRIP1 and RPS6KB1 decreases; see Examples 7 and 8 and FIGS. 9 and 10 herein. As has been further shown herein in context of the present invention, agents such as polynucleotides (exemplarily shown for miR-26a) as described herein are induced upon β₃-adrenergic stimulation, the signalling pathway that mediates cold stress to adipocytes; see Example 9 and FIG. 11 herein. Also, as exemplified using hPASC cells, the expression of UCP1 increases upon transfection with agents such as polynucleotides (exemplarily shown for miR-26a); see Example 11 and FIG. 13 herein. Vice versa, in context of the present invention, it could be shown that expression of UCP1 decreases upon neutralizing agents such as polynucleotides, e.g., as shown by transfection with LNA-based miR-26a antisense oligonucleotides in hMADS adipocytes; see Example 10 and FIG. 12 herein. In addition, elevated energy expenditure by agents such as polynucleotides (exemplarily shown for miR-26a) has been exemplarily demonstrated in hMADS adipocytes; see Example 12 and FIG. 14 herein. These findings demonstrate the suitability of agents (e.g., polynucleotides) which target UCP1-suppressors such as, e.g., RB1, NRIP1 and RPS6KB1 as described herein, for example polynucleotides comprising the sequence of SEQ ID NO: 6 (i.e. the seed sequence of e.g., miR-26a/SEQ ID NO: 1, miR-26b/SEQ ID NO: 2 and miR-1297/SEQ ID NO: 3) such as polynucleotides comprising or consisting of the sequence of SEQ ID NOs. 1 to 3, for treating or preventing a disorder of the energy homeostasis such as obesity, overweight, adiposity, metabolic syndrome, or diseases or disorders related to energy homeostasis disorders such as diabetes (e.g., diabetes type II), hypercholesterolemia or hypertension.

TABLE 1

Differentially expressed miRNAs between white and brown hMADS adipocytes. hMADS cells were treated with rosiglitazone until day 9 of differentiation for white adipogenesis and harvested at day 9 (R9d9) and day 17 (R9d17) and treated with rosiglitazone permanently for brown adipogenesis until day17 (R17d17). Indicated values are $\log_2$ ratios (NaN: not a number). Selected miRNAs are differentially expressed by $\log_2$ ratio > |0.378| between R9d17 and R17d17.

| Name | R9d9 | R9d17 | R17d17 |
|---|---|---|---|
| hsa-miR-106a | −0.02 | −0.41 | 0.15 |
| hsa-miR-125b-1* | −1.85 | −1.68 | −0.86 |
| hsa-miR-140-5p | −0.05 | −0.11 | 0.39 |
| hsa-miR-143 | 0.20 | 1.07 | 1.48 |
| hsa-miR-145* | −0.83 | −1.23 | −0.09 |
| hsa-miR-146b-5p | 0.67 | 1.09 | 0.62 |
| hsa-miR-17 | 0.01 | −0.38 | 0.12 |
| hsa-miR-185* | NaN | −0.82 | −0.16 |
| hsa-miR-186 | 0.66 | 0.36 | 0.83 |
| hsa-miR-18a | 0.68 | 0.07 | 1.02 |
| hsa-miR-18b | 0.60 | 0.24 | 0.99 |
| hsa-miR-20a | 0.25 | −0.19 | 0.26 |
| hsa-miR-222 | −2.21 | −2.32 | −2.71 |
| hsa-miR-222* | −2.57 | −1.85 | −1.45 |
| hsa-miR-301a | −0.03 | 0.52 | 0.91 |
| hsa-miR-32 | NaN | 1.38 | 2.21 |
| hsa-miR-335 | 2.17 | 2.93 | 3.41 |
| hsa-miR-424 | 0.53 | 1.30 | 0.81 |
| hsa-miR-452 | 0.57 | 0.59 | 0.20 |
| hsa-miR-455-3p | 0.27 | 1.08 | 1.63 |
| hsa-miR-455-5p | 0.32 | 1.22 | 1.85 |
| hsa-miR-496 | NaN | −0.99 | −0.38 |
| hsa-miR-744 | 0.08 | −0.10 | 0.49 |
| miRPlus_17896 | −0.34 | −0.42 | −2.30 |
| miRPlus_27560 | 0.87 | −0.10 | 0.31 |
| miRPlus_28454 | 1.75 | 2.73 | 3.26 |
| miRPlus_30317 | −0.74 | −0.41 | 0.69 |
| mmu-miR-322 | 0.47 | 1.36 | 0.60 |
| mmu-miR-452 | 0.24 | 0.41 | 1.19 |
| mmu-miR-697 | −0.91 | −0.67 | −0.22 |
| mmu-miR-708 | 0.20 | 1.47 | 2.01 |
| mmu-miR-715 | 1.28 | 1.04 | 0.40 |

RB1 is the founding member of the RB family which plays important roles in cell cycle control and cellular differentiation. Intriguingly, RB1 expression in vitro and in vivo leads to white adipocyte differentiation whereas RB1 deficiency triggers the switch from white to brown adipocytes (Hansen, Proc Natl Acad Sci USA (2004), 101: 4112-4117; Dali-Youcef, Proc Natl Acad Sci (2007), 104: 10703-10708). At the molecular level, it has been shown that RB1 acts as transcriptional repressor of PCG-1α (Scimè, Cell Metab (2005), 283-295), which is a potent co-activator of PPARγ and TRβ on the UCP1 promoter (Puigserver, Cell (1998), 92: 829-839). Hence, RB1 is a suppressor of mitochondrial biogenesis and UCP1 expression in white adipocytes (Tiraby, loc cit, Puigserver, loc cit, Wu, Cell (1999), 98: 115-124), and at least in mouse models examined so far, no adaptative thermogenesis can emanate from the activity of any protein or mechanism other than that of UCP1 in brown adipose tissue, thereby making UCP1 expression a key marker and target to increase energy expenditure and thus combat obesity (Feldmann, Cell Metab (2009), 9: 203-209).

NRIP1 is a ligand dependent nuclear receptor corepressor that plays a key role in the regulated transcription of genes involved in energy homeostasis (Hallberg, Mol Cell Biol (2008), 28: 6785-6795). NRIP1$^{-/-}$ mice are leaner than their control littermates, even when challenged by high-fat feeding (Leonardsson, loc cit). Interestingly, this phenotype is not linked to a defect in adipogenesis and the WAT of these animals expresses high levels of UCP1 (Leonardsson, Proc. Natl. Acad. Sci. USA (2004), 101: 8437-8442). This effect on UCP1 expression is due to a direct inhibition of the UCP1 promoter by NRIP1 (Christian, Mol Cell Biol (2005), 25: 9383-9391). In addition to repressing the uncoupling of respiration, NRIP1 inhibits other aspects of energy expenditure in the adipose tissue by repressing genes implicated in fatty acid oxidation, mitochondrial biogenesis and oxidative phosphorylation, resulting in increased mitochondrial density in adipocytes lacking NRIP1 (Powelka, J Clin Invest (2006), 116: 125-136). Given the high expression levels of this coregulator in WAT (Hallberg, loc cit), and its induction during adipogenesis (Nichol, J Biol Chem (2006), 281: 32140-32147), it seems reasonable to speculate that NR1P1 acts as an inhibitor of energy expenditure in WAT by blocking mitochondrial function in a tissue specialized in fat storage. Furthermore, NRIP1 also reduces glucose uptake in adipocytes, most probably explaining the enhanced glucose tolerance in NRIP1 knockout mice (Powelka, loc cit; Ho, Cell Metab (2009), 10: 516-523).

RPS6KB1 (S6K1) is activated by insulin through a canonical signal transduction pathway and is implicated in a negative feedback loop to suppress insulin signalling via inhibition of IRS1 (Um, Cell Metab (2006), 3: 393-402; Ho, loc cit; Harrington, J Cell Biol (2004), 166: 213-223). Beside its role as mediator of insulin-stimulated glucose uptake, IRS1 has been shown to promote UCP1 expression in brown adipocytes (Fasshauer, Mol Cell Biol (2001), 21: 319-329). In line with these findings, S6K1−/− mice maintained on a high-fat diet (HFD) remain insulin sensitive, are protected against diet-induced obesity, and express UCP1 in WAT (Um, Nature (2004), 431: 200-205).

In summary, in context with the present invention it has, in a particular embodiment, been found that miR-26a leads to induction of UCP1 expression in murine WAT tissue as well as in hMADS cells of undifferentiated or mature white adipocyte status. miR-26a acts via direct repression of RB1, thereby being able to derepress the expression of PGC1A, and NRIP1, which in turn activates UCP1, the responsible factor for brown fat thermogenesis (Scimè, loc cit; Hallberg, loc cit). Additionally, miR-26a-mediated repression of RPS6KB1 may activate IRS1, resulting in enhanced insulin sensitivity and stimulation of UCP1 expression. Congruently, silencing of miR-26a has the opposite effect leading to repression of UCP1 expression. Thus, the herein illustrated and exemplified miR-26a may trigger the regulatory cascade leading to brown adipogenesis at the front end. Moreover, other miRNAs, e.g., miR-26b and miR-1297 share a high degree of sequence homology at positions 1-10 and 12-15 including the miRNA seed (position 2-7), the core sequence for target mRNA identification (Bartel, Cell (2009), 136: 215-233). Thus, these miRNAs may directly target a very similar set of genes resulting in very similar regulatory functions. The capability of miRNAs to stimulate the development of undifferentiated hMADS cells into brown adipocytes via increased UCP1 expression is of general interest because approximately 10% of fat cells are estimated to be renewed annually in adults independently of body mass index (Spalding, Nature (2008), 453: 783-787). Hence, shifting de novo generation of adipocytes 'from white to brown' allows anti-obesity treatment by redirecting energy metabolism from storage to expenditure. Furthermore, the present invention demonstrates that white adipocytes can be converted to brown adipocytes by miR-26a, making the large population of white adipocytes a target for therapeutic intervention.

Without being bound by theory, the herein documented miR-26a mediated repression of NRIP1 and RPS6KB1, both known as negative regulators of glucose tolerance (Um, Nature (2004), 431: 200-205; Powelka, loc cit), may enhance insulin sensitivity by increasing insulin-stimulated glucose uptake and, thus, combat insulin resistance.

Moreover, therapeutic delivery of miR-26a which is present at low levels in tumours compared to control tissues has been shown to suppress tumorigenesis in a murine liver cancer model with no reported side effects (Kota, Cell (2009), 137: 1005-1017), demonstrating the feasibility of this technique for treatment. Hence, in vivo administration of miR-26a allows to recruit new brown fat cells, therefore to increase the oxidative capacity of the human body through controlled BAT expansion and thus to combat disorders of energy homeostasis such as obesity, overweight, adiposity, metabolic syndrome, or diseases or disorders related to energy homeostasis disorders such as diabetes (e.g., diabetes type II), hypercholesterolemia or hypertension.

Accordingly, the present invention relates to pharmaceutical compositions comprising an agent that induces or up-regulates the expression of UCP1, for example and in particular by inhibiting/negatively interfering with and/or suppressing the expression of UCP1 suppressors and/or inhibitors of the UCP1-promoting insulin signalling pathway. Herein exemplified and shown are polynucleotides that concomitantly and individually are able to negatively interfere with at least two UCP1 suppressors and/or inhibitors (suppressors) of the UCP1-promoting insulin signalling pathway. Such agents and polynucleotides are particularly useful in treating or preventing disorders of the energy homeostasis, like for example obesity, overweight, adiposity, metabolic syndrome, or diseases or disorders related to energy homeostasis disorders such as diabetes (e.g., diabetes type II), hypercholesterolemia or hypertension in a subject. Surprisingly found polynucleotides that are able to negatively interfere concomitantly and independently with at least two UCP1 suppressors and/or inhibitors (suppressors) of the UCP1-promoting insulin signalling pathway. Such polynucleotides may comprise miR/micro RNA that comprise or consist of the sequence UCAAGU (SEQ ID NO: 6), like miR-26a (SEQ ID NO: 1), miR-26b (SEQ ID NO: 2), and miR-1297 (SEQ ID NO: 3).

The present invention further relates to a method of treating or preventing disorders of energy homeostasis, like obesity, overweight, adiposity, metabolic syndrome, or diseases or disorders related to energy homeostasis disorders such as diabetes (e.g., diabetes type II), hypercholesterolemia or hypertension in a subject, said method comprising administering an effective amount of a composition comprising (a) polynucleotide(s) which induce(s) or upregulate(s) expression of UCP1. Such a method in accordance with the present invention may comprise the medical administration of an agent, like the herein disclosed polynucleotides, in particular a miRNA or a precursor or a mimic thereof, that is able to negatively interfere concomitantly and independently with at least two UCP-1 suppressors and/or inhibitors of the UCP1-promoting insulin signalling pathway. Such molecules are provided herein and comprise, inter alia, miR/micro RNA that comprises the sequence UCAAGU (SEQ ID NO: 6), like miR-26a (SEQ ID NO: 1), miR-26b (SEQ ID NO: 2), and miR-1297 (SEQ ID NO: 3). Also other useful polynucleotides, particularly microRNAs for the medical intervention of such disorders are provided herein.

The present invention further relates to compositions comprising (an) agent(s) which is/are capable of inducing transdifferentiation from white (UCP1-negative) to thermogenic (UCP1-positive) adipocytes. Such compositions may induce or upregulate expression of UCP1 and negatively interfere concomitantly and independently with at least two UCP1-suppressors and/or suppressors of the UCP1-promoting insulin signalling pathway. In context of the present invention, such compositions may be used in treating or preventing diseases or disorders of the energy homeostasis or related diseases or disorders in a subject.

The invention also provides a method of treating or preventing diseases or disorders of the energy homeostasis or related diseases or disorders in a subject, the method comprising administering to a subject in need thereof an effective amount of a composition comprising (an) agent(s) which is/are capable of inducing transdifferentiation from white (UCP1-negative) to thermogenic (UCP1-positive) adipocytes. Such compositions may induce or upregulate expression of UCP1 and negatively interfere concomitantly and independently with at least two UCP1-suppressors and/or suppressors of the UCP1-promoting insulin signalling pathway.

The disease or disorder of the energy homeostasis may be selected from the group consisting of obesity, overweight, hyperglycemia, adiposity and metabolic syndrome. Diseases or disorders related to homeostasis may be selected from the group consisting of diabetes (e.g., diabetes type II), hypercholesterolemia and hypertension. The agent may be a polynucleotide. The polynucleotide may hybridize to the mRNA of a UCP1-suppressor and/or a suppressor of the UCP1-promoting insulin signalling pathway, thereby inducing degradation or preventing translation of said mRNA. The polynucleotide may be a microRNA, a precursor of a microRNA, or a mimic microRNA or a precursor thereof. The polynucleotide may be about 15 to about 100 nucleotides in length.

In accordance with the present invention, a composition comprising an agent, like a polynucleotide which induces or upregulates expression of UCP1 may not only be used for the treatment of disorders of energy homeostasis such as obesity, overweight, adiposity, metabolic syndrome, or diseases or disorders related to energy homeostasis disorders such as diabetes (e.g., diabetes type II), hypercholesterolemia or hypertension. For example, with regard to diabetes, it has very recently been shown that also an association between BAT activity and glucose homeostasis exists (Skarulis, Endocrinol Metab (2010), 95: 256-262).

As could be demonstrated by the present inventors, the expression of UCP1 can be induced or upregulated by polynucleotides described herein, e.g., by hybridizing to the mRNA of UCP1-suppressors, thereby inducing degradation or preventing translation of said mRNA. Examples for such UCP1-suppressors are RB1, NRIP1, RPS6KB1, twist homolog 1 (*Drosophila*) (TWIST1), nuclear receptor coactivator 2 (NCOA2, TIF2), eukaryotic translation initiation factor 4E binding protein 1 (EIF4EBP1, 4E-BP1), similar to integrin, alpha M (complement component receptor 3, alpha; also known as CD11 b (p170), macrophage antigen alpha polypeptide) (*H. sapiens*) (p170), wingless-type MMTV integration site family, member 10B (WNT10B), CIDEA, nuclear receptor subfamily 2, group F, member 1 (NR2F1, COUP-TFI), nuclear receptor subfamily 2, group F, member 2 (NR2F2, COUP-TFII), and nuclear receptor subfamily 1, group H, member 3 (NR1H3, LXR) (Hansen and Kristiansen, Biochem J (2006), 398: 153-168). In accordance with the present invention, UCP1-suppressors as used herein, e.g., those which are negatively interfered with or whose degradation is induced or whose translation is prevented by the agents, compositions and polynucleotides described herein may either directly suppress UCP1 (e.g., transcription, translation, expression or activity of UCP1) by directly negatively interfering with UCP1 (e.g., UCP1-DNA, UCP1-RNA, UCP1-mRNA or UCP1-protein), or may indirectly suppress UCP1 (e.g., transcription, translation, expression or activity of UCP1) by indirectly negatively interfering with a UCP1-activator (e.g., DNA, RNA, mRNA or protein of said UCP1-activator). For example, as described above, RB1 is negatively interfering with the UCP1-activator PGC1A, Thus, RB1 is an indirect UCP-1-suppressor in context with the present invention. NRIP1 is an example of a direct UCP1-suppressor since it directly negatively interferes with UCP1. Also, in context of the present invention, UCP1-suppressors may be suppressors/inhibitors of the UCP1-promoting insulin signalling pathway. An example of such a suppressor/inhibitor of the UCP1-promoting insulin signalling pathway is RPS6KB1. Alternatively, in accordance with the present invention, the polynucleotides described herein may also hybridize to the mRNA of (a) UCP1-activator(s), thereby inducing stabilization or translation of said mRNA. Examples for UCP1-activators are PGC1A, PGC1B, PPARG, sirtuin 3 (SIRT3), cAMP responsive element binding protein 1 (CREB), mitogen-activated protein kinase 14 (MAPK14), protein arginine methyltransferase 1 (PRMT1) and insulin signalling (Hansen and Kristiansen, Biochem J (2006), 398: 153-168).

As could be demonstrated in context of the present invention, the prevention of autophagy in vitro and in vivo reveals brown-like characteristics in adipocytes (Singh, JCI (2009), 458(7242): 1131-1135; Zhang, PNAS (2009), 106(47): 19860-19865). Autophagy is an intracellular catabolic process involving the degradation of a cell's own components through the lysosomal machinery. Autophagy is mediated by an unique organelle called the autophagosome which engulfs the portion of the cytoplasm that should degraded. Autophagy can be subdivided in three main steps. When a metabolic stress is initiated, two main signals allow phagophore (precursor of the autophagosome) formation and nucleation. The first elicits the formation of a complex with ATG13 autophagy related 13 homolog (ATG13), unc-51-like kinase 1 (ULK1, ATG1), and RB1-inducible coiled-coil 1 (ATG11, RB1CC1, FIP200). The second one involves only for canonical autophagy used the pathway of beclin 1, autophagy related (BECN1, ATG6) and phosphoinositide-3-kinase, class 3 (PIK3C3, VPS34). ATG9 autophagy related 9 homolog A (ATG9A) and homolog B (ATG9B) and ATG11 are also necessary to stabilize the phagophore. The complex of ATG12 autophagy related 12 homolog (ATG12), ATG5 autophagy related 5 homolog (ATG5), and ATG16 autophagy related 16-like 1 (ATG16L) is involved in elongation of the phagophore. After, ATG4 autophagy related 4 homolog A, B, C, and D (ATG4A, ATG4B, ATG4C, ATG4D)- and ATG16L facilitate ATG3 autophagy related 3 homolog (ATG3)-dependent conjugation of phosphatidylethanolamine to microtubule-associated protein 1 light chain 3 alpha (MAP1LC3A, ATG8E, LC3) by forming a complex with ATG12 and ATG5. After completion of autophagosome formation, fusion with lysosomes (acidic vacuoles) is facilitated by lysosomal-associated membrane protein 2 (LAMP-2) protein and hydrolases, including cathepsins are discharged into the autophagosome to degrade its content to mediate macromolecules and amino acids efflux. (Puissant, Cell Cycle (2010), 9(17): 3470-8). In context of the present invention, 11 out of 21 autophagy-related genes (ATGs) were identified as targets for the miRNAs miR-106a (SEQ ID NO: 9), miR-17 (SEQ ID NO: 10), and miR-20a (SEQ ID NO: 11): ATG1, ATG2a, ATG2b, ATG5, ATG6, ATG10, ATG11, ATG12, ATG14, ATG15, and ATG16L1; cf. Table 2 herein. Accordingly, miR-106a (SEQ ID NO: 9), miR-17 (SEQ ID NO: 10) and miR-20a (SEQ ID NO: 11) as well as other polynucleotides comprising the seed sequences of these miRNAs (SEQ ID NO: 33) may be used for the medical purposes as described herein, i.e. particularly for the treatment of disorders of energy homeostasis such as obesity, overweight, adiposity, metabolic syndrome, or diseases or disorders related to energy homeostasis disorders such as diabetes (e.g., diabetes type II), hypercholesterolemia or hypertension.

Generally, for the case that that polynucleotide is a microRNA, there are several mechanisms known in the art by which such microRNA-mediated activation, i.e. inducing transcription, stabilization or translation of a mRNA, can work (Vasudevan, Science (2007), 318(5858): 1931-1934; Place, Proc Natl. Acad Sci USA (2008), 105: 1608-1613; Tsai, Biochem J (2009), 424(3): 411-418).

In one embodiment of the present invention, the polynucleotide which induces or upregulates expression of UCP1 to be employed in context of this invention is a microRNA (also abbreviated herein as miRNA or miR) or a precursor thereof, a mimic microRNA or a precursor thereof. However, it is also envisaged that other agents or molecules that target for example at least two at least two UCP1 suppressors and/or inhibitors of the UCP1-promoting insulin signalling pathway are employed in the medical intervention of disorders of the energy homeostasis like obesity, overweight, metabolic syndrome and the like or diseases or disorders related to energy homeostasis disorders such as diabetes (e.g., diabetes type II), hypercholesterolemia or hypertension. Such molecules may comprise an siRNA or a precursor thereof, a long non-coding RNA or a precursor thereof, an snRNA (small/short hairpin RNA) or a precursor thereof, an stRNA (small temporal RNA) or a precursor thereof, an fRNA (functional RNA) or a precursor thereof, an snRNA (small nuclear RNA) or a precursor thereof, a snoRNA (small nucleolar RNA) or a precursor thereof, a piRNA (piwi-interacting RNA) or a precursor thereof, a tasiRNA (trans-acting small/short interfering RNA) or a precursor thereof, an aRNA (antisense RNA) or a precursor thereof, or a small non-coding RNA or a precursor thereof. As used herein, "precursors" of the polynucleotides described in and to be employed in context with the present invention may be forms of the respective polynucleotides as they occur during maturation of the respective polynucleotides. For example, in context with the present invention, precursors of a microRNA or a mimic microRNA may be primary miRNAs (pri-miRNAs) or precursor miRNAs (pre-miRNAs) as occurring during maturation of miRNAs. Both are single transcripts (i.e. ssRNA) that fold into a characteristic intramolecular secondary structure, the so-called "hairpin loop", which contains a stretch of about 20 base pairs, which is often interrupted by mismatches. In context with the present invention, precursors of siRNAs may be long dsRNA molecules or shorter "hairpin loop" ssRNA molecules. Both types of these siRNA precursors may contain a stretch of base pairs without any mismatch. The current model for maturation of mammalian miRNAs is nuclear cleavage of the primary miRNA (pri-miRNA) which liberates a 60-70 nt stem loop intermediate, known as the miRNA precursor or pre-miRNA. The mature about 18-23 nt long miRNA is yielded from one arm of the stem loop precursor (Bartel, Cell (2004), 116: 281-297; Lee, EMBO J (2002), 21: 4663-4670; Zeng and Cullen, RNA (2003), 9: 112-123). In a preferred embodiment of the present invention, the polynucleotide is a microRNA or a precursor thereof or a mimic microRNA or a precursor thereof. The polynucleotides of the present invention may be of any length. However, the polynucleotide should be, in one embodiment, capable of interfering with at least two UCP1 suppressors in order to, for example induce the degradation of the corresponding mRNA encoding such UCP1 suppressors and/or prevent, for example the translation of such an mRNA encoding for these UCP1 suppressors. Accordingly, such a polynucleotide is preferably capable of negatively interfering concomitantly and independently with at least two UCP1 suppressors and/or inhibitors of the UCP1-promoting insulin signalling pathway. Preferably, the polynucleotide is about 15 to about 100 nucleotides in length, more preferably about 15 to about 30 nucleotides and most preferably about 15 to about 25 nucleotides, specifically, e.g., about 21 nucleotides. It is believed that about 21 nt long RNA oligonucleotides act as the only functional entities in RNA interference (RNAi), guiding the RNA-induced silencing complex (RISC) to target transcripts. However, it is conceivable that far longer polynucleotides with a length of several kilobases might be efficiently processed endogenously to yield functional about 21 nt oligonucleotides which, via the RNAi pathway, can ultimately repress target transcripts and modulate biological processes.

In one embodiment of this invention, medical useful microRNA molecules are provided. Such molecules are also provided in Table 2 herein below and are also identified in the appended sequence listing. Such microRNAs to be employed in the treatment and/or prevention may also comprise miR-106a (SEQ ID NO: 9), miR-17 (SEQ ID NO. 10), miR-20a (SEQ ID NO: 11) or a polynucleotide that comprises the common seed sequence of these three miRs, namely the sequence AAAGUG (SEQ ID NO: 33). Also envisaged in the medical intervention of such energy homeostasis disorders is miR452 (SEQ ID NO: 7, human, and SEQ ID NO: 8, murine) or a polynucleotide like an miR/microRNA that comprises the sequence SEQ ID NO: 34, namely UGUUUGCAGAG-GAAACUGA.

In a specific embodiment of the present invention, the polynucleotide to be employed in context of this invention (i.e. in the medical intervention of a diseased energy homeostasis, like obesity, overweight, adiposity, obesity, metabolic syndrome, or diseases or disorders related to energy homeostasis disorders such as diabetes (e.g., diabetes type II), hypercholesterolemia or hypertension) may be selected from the group consisting of:
  (i) a polynucleotide comprising the nucleotide sequence of SEQ ID NO: 1 (i.e. miR-26a);
  (ii) a polynucleotide comprising the nucleotide sequence of SEQ ID NO: 2 (i.e. miR-26b);
  (iii) a polynucleotide comprising the nucleotide sequence of SEQ ID NO: 3 (i.e. miR-1297);
  (iv) a polynucleotide which is at least 25%, 30%, 35%, 40%, 45%, 50%, 55%, 60%, 65%, 70%, 75%, 80%, 85%, 90%, 95%, 97%, 98% or 99% identical to any one of (i) to (iii); and
  (v) a polynucleotide according to (iv), which comprises the nucleotide sequence of SEQ ID NO: 6 (i.e. seed sequence of SEQ ID NOs. 1 to 3),
whereby said polynucleotide of (iv) and/or (v) is able to induce or upregulate expression of UCP1.

The medical uses described and provided herein may also be carried out with polynucleotides (e.g., miRNAs) as exemplarily shown in the group consisting of:
  (i) a polynucleotide comprising the nucleotide sequence of SEQ ID NO: 9 (i.e. miR-106a);
  (ii) a polynucleotide comprising the nucleotide sequence of SEQ ID NO: 10 (i.e. miR-17);
  (iii) a polynucleotide comprising the nucleotide sequence of SEQ ID NO: 11 (i.e. miR-20a);
  (iv) a polynucleotide which is at least 25%, 30%, 35%, 40%, 45%, 50%, 55%, 60%, 65%, 70%, 75%, 80%, 85%, 90%, 95%, 97%, 98% or 99% identical to any one of (i) to (iii); and
  (v) a polynucleotide according to (iv), which comprises the nucleotide sequence of SEQ ID NO: 33 (i.e. seed sequence of SEQ ID NOs. 9 to 11),
whereby said polynucleotide of (iv) and/or (v) is able to induce or upregulate expression of UCP1. Especially, without being bound by theory, the above polynucleotides, particularly those comprising SEQ ID NO: 9, 10, 11 or 33, are able to induce or upregulate mitochondrial function or are able to induce or upregulate energy expenditure.

Further examples of polynucleotides (e.g., miRNAs) which may be employed in the medical uses as described and provided herein are comprised in the group consisting of:
  (i) a polynucleotide comprising the nucleotide sequence of SEQ ID NO: 7 (i.e. miR-452, human);
  (ii) a polynucleotide comprising the nucleotide sequence of SEQ ID NO: 8 (i.e. miR-452, murine);
  (iii) a polynucleotide which is at least 25%, 30%, 35%, 40%, 45%, 50%, 55%, 60%, 65%, 70%, 75%, 80%, 85%, 90%, 95%, 97%, 98% or 99% identical to a (i) or (ii); and
  (iv) a polynucleotide according to (iii), which comprises the nucleotide sequence of SEQ ID NO: 34 (i.e. consensus sequence of SEQ ID NOs. 7 and 8),
whereby said polynucleotide of (iii) and/or (iv) is able to induce or upregulate expression of UCP1.

Generally, in context of the present invention, identity levels of nucleotide sequences may refer to the entire length of nucleotide sequence of the referred to SEQ ID NOs. and may be assessed pair-wise, wherein each gap may be counted as one mismatch.

For example, the term "identity" may be used herein in the context of a polynucleotide to be employed in context with the present invention which has a nucleic acid sequence with an identity of at least 25%, 30%, 35%, 40%, 45%, 50%, 55%, 60%, 65%, 70%, 75%, 80%, 85%, 90%, 95%, 97%, 98% or 99% to a polynucleotide comprising or consisting of the nucleotide sequence of any one of SEQ ID NO: 1 (miR-26a), SEQ ID NO: 2 (miR-26b), SEQ ID NO: 3 (miR-1297), SEQ ID NO: 4 (miR-222*), SEQ ID NO: 5 (miR-335), SEQ ID NO: 6 (seed sequence of SEQ ID NOs. 1 to 3), SEQ ID NO: 7 (miR-452 human), SEQ ID NO: 8 (miR-452 murine), SEQ ID NO: 9 (miR-106a), SEQ ID NO: 10 (miR-17), SEQ ID NO: 11 (miR-20a), SEQ ID NO: 33 (seed sequence of SEQ ID NOs. 9 to 11), SEQ ID NO: 34 (consensus sequence of SEQ ID NOs 7 and 8), or any other SEQ ID NO. or consensus or seed sequence as shown in Table 2 herein, respectively, for example over the entire length. As mentioned, envisaged for the medical intervention in context of the present invention are polynucleotides as provided with miR-106a (SEQ ID NO. 9), miR-17 (SEQ ID NO. 10), miR-20a (SEQ ID NO. 11) or a polynucleotide that comprises the common seed sequence of these three miRNAs, namely the sequence AAAGUG (SEQ ID NO: 33). Also envisaged in the medical intervention of such energy homeostasis disorders is miR-452 (SEQ ID NO. 7, human, and SEQ ID NO. 8, murine) or a polynucleotide like an miR/microRNA that comprises the sequence SEQ ID NO: 34, namely UGUUUGCAGAGGAAACUGA.

Furthermore, in context of the present invention, a polynucleotide to be employed in context with the present invention may also have a nucleic acid sequence with an identity of at least 25%, 30%, 35%, 40%, 45%, 50%, 55%, 60%, 65%, 70%, 75%, 80%, 85%, 90%, 95%, 97%, 98% or 99% to a polynucleotide comprising or consisting of the nucleotide sequence of any one of the consensus or seed sequences as shown in Table 2 including one or two nucleotide(s) of the corresponding mature sequence at the 5'-end and/or the 3'-end of the respective consensus or seed sequence. For example, in the context of the present invention, a polynucleotide to be employed in context with the present invention may have a nucleic acid sequence with an identity of at least 25%, 30%, 35%, 40%, 45%, 50%, 55%, 60%, 65%, 70%, 75%, 80%, 85%, 90%, 95%, 97%, 98% or 99% to a polynucleotide comprising or consisting of the nucleotide sequence U UCAAGU A (i.e. the seed sequence of SEQ ID NO: 1 plus one nucleotide of the corresponding mature sequence at the 5'-end and one nucleotide of the corresponding mature sequence at the 3'-end). If two nucleic acid sequences being compared by sequence comparisons differ in identity, then the term "identity" refers to the shorter sequence and to the part of the longer sequence that matches said shorter sequence. Therefore, when the sequences which are compared do not have the same length, the degree of identity preferably either refers to the percentage of nucleotide residues in the shorter sequence which are identical to consecutive nucleotide residues contained in the longer sequence or to the percentage of consecutive nucleotides contained in the longer sequence which are identical to the nucleotide sequence of the shorter sequence. Of course, as described above, a gap as "part of consecutive nucleotides" may be counted as a mismatch. In this context, the skilled person is readily in the position to determine that part of a longer sequence that "matches" the shorter sequence. Also, these definitions for sequence comparisons (e.g., establishment of "identity" values) are to be applied for all sequences described and disclosed herein.

TABLE 2 miRNAs, miRBase ID (miRBase: http://www.mirbase.org, Release 14 (September 2009), mature sequences (consensus sequences in bold; seed sequences underscored) and targets in accordance with algorithms (based on miRNA response elements (MREs) (also called miRNA binding sites (MBS)) in their 3'UTR). miRNAs are clustered according to their sequence similarity in seed sequence thereby with similarities in their predicted targets. miRNA* denotes the small RNA processed from the hairpin arm opposite of the mature miRNA.

| miRNA | miRBase ID | Sequence | SEQ ID NO. | target mRNA in accordance with algorithms* |
|---|---|---|---|---|
| hsa-miR-26a | MIMAT0000082 | UUCAAGUAAUCCAGGAUAGGCU | 1 | RB1, NRIP1, RPS6KB1 |
| hsa-miR-26b | MIMAT0000083 | UUCAAGUAAUUCAGGAUAGGU | 2 | RB1, NRIP1, RPS6KB1 |
| hsa-miR-1297 | MIMAT0005886 | UUCAAGUAAUUCAGGUG | 3 | RB1, NRIP1, RPS6KB1 |
| hsa-miR-106a | MIMAT0000103 | AAAAGUGCUUACAGUGCAGGUAG | 9 | RB1, NRIP1, RPS6KB1, ATG1, ATG2A, ATG2B, ATG5, ATG6, ATG10, ATG11, ATG12, ATG14, ATG15, ATG16L1 |
| hsa-miR-17 | MIMAT0000070 | CAAAGUGCUUACAGUGCAGGUAG | 10 | RB1, NRIP1, RPS6KB1, ATG1, ATG2A, ATG2B, ATG5, ATG6, ATG10, ATG11, ATG12, ATG14, ATG15, ATG16L1 |
| hsa-miR-20a | MIMAT0000075 | UAAAGUGCUUAUAGUGCAGGUAG | 11 | RB1, NRIP1, RPS6KB1, ATG1, ATG2A, ATG2B, ATG5, ATG6, ATG10, ATG11, ATG12, ATG14, ATG15, ATG16L1 |
| hsa-miR-452 | MIMAT0001635 | AACUGUUUGCAGAGGAAACUGA | 7 | RB1, NRIP1, RPS6KB1 |
| mmu-miR-452 | MIMAT0001637 | UGUUUGCAGAGGAAACUGAGAC | 8 | RB1, RPS6KB1 |
| hsa-miR-18a | MIMAT0000072 | UAAGGUGCAUCUAGUGCAGAUAG | 12 | |
| hsa-miR-18b | MIMAT0001412 | UAAGGUGCAUCUAGUGCAGUUAG | 13 | |
| hsa-miR-424 | MIMAT0001341 | CAGCAGCAAUUCAUGUUUUGAA | 17 | |
| mmu-miR-322 | MIMAT0000548 | CAGCAGCAAUUCAUGUUUUGAA | 18 | |
| hsa-miR-140-5p | MIMAT0000431 | CAGUGGUUUUACCCUAUGGUAG | 14 | PGC-1a |
| hsa-miR-301a | MIMAT0000688 | CAGUGCAAUAGUAUUGUCAAAGC | 15 | PGC-1a, V-type ATPase (neg. regulator of insulin-responsive GLUT4 vesicle biogenesis) |

TABLE 2-continued miRNAs, miRBase ID (miRBase: http://www.mirbase.org, Release 14 (September 2009), mature sequences (consensus sequences in bold; seed sequences underscored) and targets in accordance with algorithms (based on miRNA response elements (MREs) (also called miRNA binding sites (MBS)) in their 3'UTR). miRNAs are clustered according to their sequence similarity in seed sequence thereby with similarities in their predicted targets. miRNA* denotes the small RNA processed from the hairpin arm opposite of the mature miRNA.

| miRNA | miRBase ID | Sequence | SEQ ID NO. | target mRNA in accordance with algorithms* |
|---|---|---|---|---|
| hsa-miR-32 | MIMAT0000090 | UAUUGCACAUUACUAAGUUGCA | 16 | V-type ATPase (neg. regulator of insulin-responsive GLUT4 vesicle biogenesis) |
| hsa-miR-125b-1* | MIMAT0004592 | ACGGGUUAGGCUCUUGGGAGCU | 19 | |
| hsa-miR-222* | MIMAT0004569 | CUCAGUAGCCAGUGUAGAUCCU | 4 | |
| hsa-miR-335 | MIMAT0000765 | UCAAGAGCAAUAACGAAAAAUGU | 5 | |
| hsa-miR-143 | MIMAT0000435 | UGAGAUGAAGCACUGUAGCUC | 20 | |
| hsa-miR-145* | MIMAT0004601 | GGAUUCCUGGAAAUACUGUUCU | 21 | |
| hsa-miR-146b-5p | MIMAT0002809 | UGAGAACUGAAUUCCAUAGGCU | 22 | |
| hsa-miR-185* | MIMAT0004611 | AGGGGCUGGCUUUCCUCUGGUC | 23 | |
| hsa-miR-186 | MIMAT0000456 | CAAAGAAUUCUCCUUUUGGGCU | 24 | |
| hsa-miR-222 | MIMAT0000279 | AGCUACAUCUGGCUACUGGGU | 25 | |
| hsa-miR-455-3p | M1MAT0004784 | GCAGUCCAUGGGCAUAUACAC | 26 | |
| hsa-miR-455-5p | MIMAT0003150 | UAUGUGCCUUUGGACUACAUCG | 27 | |
| hsa-miR-496 | MIMAT0002818 | UGAGUAUUACAUGGCCAAUCUC | 28 | |
| hsa-miR-744 | MIMAT0004945 | UGCGGGGCUAGGGCUAACAGCA | 29 | |
| mmu-miR-697 | MIMAT0003487 | AACAUCCUGGUCCUGUGGAGA | 30 | |
| mmu-miR-708 | MIMAT0004828 | AAGGAGCUUACAAUCUAGCUGGG | 31 | |
| mmu-miR-715 | MIMAT0003506 | CUCCGUGCACACCCCCGCGUG | 32 | |

*The following ten publicly available target algorithms were used: (A) miRBase Targets (Griffiths-Jones, Nucleic Acids Res (2008), 36: D154-D158; URL: http://microrna.sanger.ac.uk), (B) miRanda (Betel, Nucleic Acids Res (2008), 36: D149-D153; URL: http://www.microrna.org), (C) PITA (Kertesz, Nat Genet (2007), 39: 1278-1284; URL: http://genie.weizmann.ac.il/pubs/mir07/mir07_data.html), (D) PicTar (two algorithms; Grün, PLoS Comput Biol (2005), 1: e13; Krek, Nat Gen (2005), 37: 495-500; URL: http://pictar.mdc-berlin.de), (E) TargetScan (two algorithms; Friedman, Genome Res (2008), 19: 92-105; URL: http://targetscan.org), (F) DIANA-microT (Hatzigeorgiou, Nucleic Acids Res (2009), 37(suppl 2): W273-W276.; URL: http://diana.cslab.ece.ntua.gr/microT), (G) ElMMo (Gaidatzis, BMC Bioinformatics (2007), 8: 69; URL: http://www.mirz.unibas.ch/ElMMo2) (H) rna22 (Miranda Cell (2006), 126: 1203-1217; URL: http://cbcsrv.watson.ibm.com/rna22.html). Individual miRNA-target interactions are in accordance with the following algorithms: miR-26a/RB1: B, C, E, G; miR-26a/NRIP1: B, C, D, E, G; miR-26a/RPS6KB1: B, C; miR-26b/RB1: B, C, E, G; miR-26b/NRIP1: B, C, E, G; miR-26b/RPS6KB1: B, C; miR-1297/RB1: B, C; miR-1297/NRIP1: B, C; miR-1297/RPS6KB1: B, C; miR-106a/RB1: B, C, E, G; miR-106a/NRIP1: C, G; miR-106a/RPS6KB1: C; miR-106a/ATG1: C, E, G; miR-106a/ATG2A: C, E; miR-106a/ATG2B: B, C, E, G; miR-106a/ATG5: B, C, E, G; miR-106a/ATG6: C, E; miR-106a/ATG10: A, C, E, H; miR-106a/ATG11: B, C, D, G; miR-106a/ATG12: C, E, H; miR-106a/ATG14: C, E, G, H; miR-106a/ATG15: C, E; miR-106a/ATG16L1: C, E, G; miR-17/RB1: B, C, G; miR-17/NRIP1: C; miR-17/RPS6KB1: C; miR-17/ATG1: C, G; miR-17/ATG2A: C, G; miR-17/ATG2B: B, C, G; miR-17/ATG5: B, C; miR-17/ATG6: C; miR-17/ATG10: A, C; miR-17/ATG11: B, C, G; miR-17/ATG12: A, C; miR-17/ATG14: C, G; miR-17/ATG15: C; miR-17/ATG16L1: C, G; miR-20a/RB1: B, C, D, E, G; miR-20a/NRIP1: A, B, C; miR-20a/RPS6KB1: B, C; miR-20a/ATG1: C, D, E, G; miR-20a/ATG2A: C, E, G; miR-20a/ATG2B: B, C, E, G; miR-20a/ATG5: B, C, E; miR-20a/ATG6: C, E, G; miR-20a/ATG10: A, C, E, H; miR-20a/ATG11: B, C, D, G; miR-20a/ATG12: C, E, H; miR-20a/ATG14: C, E, G, H; miR-20a/ATG15: C, E; miR-20a/ATG16L1: C, D, E, G; hsa-miR-452/RB1: B; hsa-miR-452/NRIP1: B, C, E; hsa-miR-452/RPS6KB1: C, E; mmu-miR-452/RB1: C; mmu-miR-452/RPS6KB1: B, C, E Identity, moreover, means that there is preferably a functional and/or structural equivalence between the corresponding nucleotide sequences. Nucleic acid sequences having the given identity levels to the particular nucleic acid sequences of the polynucleotides of the present invention may represent derivatives/variants of these sequences which, preferably, have the same biological function. In context with the present invention, the biological function of a polynucleotide described herein to be employed in context with the present invention is the ability to induce or upregulate expression of UCP1, e.g., by hybridizing to the mRNA of a UCP1-suppressor, thereby inducing degradation or preventing translation of the UCP1-suppressor mRNA, or, e.g., by hybridizing to the promoter or mRNA of a UCP1-activator or of UCP1 itself, thereby inducing stabilization or translation of the UCP1-activator mRNA or UCP1 mRNA itself. Whether the expression of UCP1 has been induced or upregulated can be easily tested by methods well known in the art and as also described herein. Examples of such methods suitable to determine whether the expression of UCP1 protein is induced or upregulated are polyacrylamide gel electrophoresis and related blotting techniques such as Western Blot paired with chromogenic dye-based protein detection techniques (such as silver or coomassie blue staining) or with fluorescence- and luminescence-based detection methods for proteins in solutions and on gels, blots and microarrays, such as immunostaining, as well as immunoprecipitation, ELISA, microarrays, and mass spectrometry. To determine whether a polynucleotide hybridizes to the mRNA of a UCP1-suppressor or to the promoter or mRNA of a UCP1-activator can also be tested by methods well known in the art and as also described herein. Examples of such methods suitable to determine whether a polynucleotide hybridizes to another nucleic acid are reporter gene assays in which commonly used reporter genes are fluorescent proteins such as Green Fluorescent Protein (GFP), enhanced GFP (eGFP), Yellow Fluorescent Protein (YFP), enhanced YFP (eYFP), Blue Fluorescent Protein (BFP), enhanced BFP (eBFP), luminescent proteins such as the enzymes *Renilla* or firefly luciferase, and (3-galactosidase encoded by the lacZ gene (Inui, Nat Rev Mol Cell Biol (2010), 11: 252-63). Whether the mRNA of a UCP1-suppressor is degraded or its translation is prevented can also be tested by methods known in the art and as also described herein. Examples for methods suitable to determine whether an mRNA is degraded are qPCR, RT-PCR, qRT-PCR, RT-qPCR, Light Cycler®, TaqMan® Platform and Assays, Northern blot, dot blot, microarrays, next generation sequencing (VanGuilder, Biotechniques (2008), 44(5): 619-26; Elvidge, Pharmacogenomics (2006), 7: 123-134; Metzker, Nat Rev Genet (2010), 11: 31-46; Kafatos, NAR (1979), 7: 1541-1552). The polynucleotides to be employed in context with the present invention may be either naturally occurring variations, for instance sequences from other varieties, species, etc., or mutations, and said mutations may have formed naturally or may have been produced by deliberate mutagenesis. Furthermore, the variations may be synthetically produced sequences. The allelic variants may be naturally occurring variants or synthetically produced variants or variants produced by recombinant DNA, RNA, PNA, GNA, TNA or LNA techniques known in the art. Deviations from the above-described nucleic acid sequences may have been produced, e.g., by deletion, substitution, addition, insertion of nucleotides and/or by recombination. The term "addition" refers to adding at least one nucleic acid residue to one or both ends of the given sequence, whereas "insertion" refers to inserting at least one nucleic acid residue within a given nucleotide sequence. The term "deletion" refers to deleting or removal of at least one nucleic acid residue in a given nucleotide sequence. The term "substitution" refers to the replacement of at least one nucleic acid residue in a given nucleotide sequence. These definitions as used here apply mutatis mutandis for all sequences provided and described in the present invention.

The polynucleotides described in and to be employed in context with the present invention (i.e. a polynucleotide which induces or upregulates expression of UCP1 for use in treating or preventing disorders of energy homeostasis such as obesity, overweight, adiposity, metabolic syndrome, or diseases or disorders related to energy homeostasis disorders such as diabetes (e.g., diabetes type II), hypercholesterolemia or hypertension) may be nucleic acid analogues such as DNA molecules, RNA molecules, oligonucleotide thiophosphates, substituted ribo-oligonucleotides, LNA molecules, PNA molecules, GNA (glycol nucleic acid) molecules, TNA (threose nucleic acid) molecules, morpholino polynucleotides, or antagomir (cholesterol-conjugated) polynucleotides. Furthermore, the term "polynucleotide" is to be construed equivalently with the term "nucleic acid molecule" in context with the present invention and may refer to DNA, RNA, PNA or LNA or hybrids thereof or any modification thereof that is known in the art (see, e.g., U.S. Pat. No. 5,525,711, U.S. Pat. No. 4,711,955, U.S. Pat. No. 5,792,608 or EP 302175 for examples of modifications). Nucleic acid residues comprised by the polynucleotides described in and to be employed in context with the present invention may be naturally occurring nucleic acid residues or artificially produced nucleic acid residues. Examples for nucleic acid residues are adenine (A), guanine (G), cytosine (C), thymine (T), uracil (U), xanthine (X), and hypoxanthine (HX). In context with the present invention, thymine (T) and uracil (U) may be used interchangeably depending on the respective type of polynucleotide. For example, as the skilled person is aware of, a thymine (T) as part of a DNA corresponds to an uracil (U) as part of the corresponding transcribed mRNA. The polynucleotides to be employed in context with the present invention may be single- or double-stranded, linear or circular, natural or synthetic, and without any size limitation. For instance, the polynucleotide sequence may be a microRNA (miRNA) or a precursor thereof, a mimic microRNA or a precursor thereof, an siRNA or a precursor thereof, a long non-coding RNA or a precursor thereof, an snRNA (small/short hairpin RNA) or a precursor thereof, an stRNA (small temporal RNA) or a precursor thereof, an fRNA (functional RNA) or a precursor thereof, an snRNA (small nuclear RNA) or a precursor thereof, a snoRNA (small nucleolar RNA) or a precursor thereof, a piRNA (piwi-interacting RNA) or a precursor thereof, a tasiRNA (trans-acting small/short interfering RNA) or a precursor thereof, an aRNA (antisense RNA) or a precursor thereof, or a small non-coding RNA or a precursor thereof, genomic DNA, cDNA, mRNA, ribozymal or a DNA encoding the before mentioned RNAs or chimeroplasts (Gamper, Nucleic Acids Research, 2000, 28, 4332-4339). As already described, as used herein, "precursors" of the polynucleotides described in and to be employed in context with the present invention may be forms of the respective polynucleotides as they occur during maturation of the respective polynucleotides. For example, in context with the present invention, precursors of a microRNA or a mimic microRNA may be primary miRNAs (pri-miRNAs) or precursor miRNAs (pre-miRNAs) as occurring during maturation of miRNAs. Both are single transcripts (i.e. ssRNA) that fold into a characteristic intramolecular secondary structure, the so-called "hairpin loop", which contains a stretch of about 20 base pairs, which is often interrupted by mismatches. In context with the present invention, precursors of siRNAs may be long dsRNA molecules or shorter "hairpin loop" ssRNA molecules. Both types of these siRNA precursors may contain a stretch of base pairs without any mismatch. The current model for maturation of mammalian miRNAs is nuclear cleavage of the primary miRNA (pri-miRNA) which liberates a 60-70 nt stem loop intermediate, known as the miRNA precursor or pre-miRNA. The mature about 18-23 nt long miRNA is yielded from one arm of the stem loop precursor (Bartel, Cell (2004), 116: 281-297; Lee, EMBO J (2002), 21: 4663-4670; Zeng and Cullen, RNA (2003), 9: 112-123). Said polynucleotides may be in the form of a plasmid or of viral DNA or RNA. Preferably, the polynucleotide described in and to be employed in context with the present invention is a microRNA or a mimic microRNA.

The present invention also relates to a polynucleotide which induces or upregulates expression of UCP1 to be employed in context with the present invention, wherein the polynucleotide comprises or consists of the nucleotide sequence of any one of SEQ ID NO: 1 (miR-26a), SEQ ID NO: 2 (miR-26b), SEQ ID NO: 3 (miR-1297), SEQ ID NO: 4 (miR-222*,), SEQ ID NO: 5 (miR-335), SEQ ID NO: 6 (seed sequence of SEQ ID NOs. 1 to 3), SEQ ID NO: 7 (miR-452 human), SEQ ID NO: 8 (miR-452 murine), SEQ ID NO: 9 (miR-106a), SEQ ID NO: 10 (miR-17), SEQ ID NO: 11 (miR-20a), SEQ ID NO: 33 (seed sequence of SEQ ID NOs. 9 to 11), SEQ ID NO: 34 (consensus sequence of SEQ ID NOs. 7 and 8), or any other SEQ ID NO. or consensus or seed sequence as shown in Table 2 herein. Furthermore, in the context of the present invention, a polynucleotide to be employed in context with the present invention may also have a nucleic acid sequence comprising or consisting of the nucleotide sequence of any one of the consensus or seed sequences as shown in Table 2 including one or two nucleotide(s) of the corresponding mature sequence at the 5'-end and/or the 3'-end of the respective consensus or seed sequence. For example, in the context of the present invention, a polynucleotide to be employed in context with the present invention may have a nucleic acid sequence comprising or consisting of the nucleotide sequence AC UGUUUGCAGAGGAAACUGA (i.e. the consensus sequence of SEQ ID NO: 7 plus two nucleotides of the corresponding mature sequence at the 5'-end) or U UCAAGU A (i.e. the seed sequence of SEQ ID NO: 1 plus one nucleotide of the corresponding mature sequence at the 5'-end and one nucleotide of the corresponding mature sequence at the 3'-end). The present invention also describes polynucleotides to be employed in context with the present invention (i.e. polynucleotides which induces or upregulates expression of UCP1 for use in treating or preventing disorders of energy homeostasis such as obesity, overweight, adiposity, metabolic syndrome, or diseases or disorders related to energy homeostasis disorders such as diabetes (e.g., diabetes type II), hypercholesterolemia or hypertension) which comprise or consist of the nucleotide sequence shown in any one of SEQ ID NO: 1 (miR-26a), SEQ ID NO: 2 (miR-26b), SEQ ID NO: 3 (miR-1297), SEQ ID NO: 4 (miR-222*), SEQ ID NO: 5 (miR-335), SEQ ID NO: 6 (seed sequence of SEQ ID NOs. 1 to 3), SEQ ID NO: 7 (miR-452 human), SEQ ID NO: 8 (miR-452 murine), SEQ ID NO: 9 (miR-106a), SEQ ID NO: 10 (miR-17), SEQ ID NO: 11 (miR-20a), SEQ ID NO: 33 (seed sequence of SEQ ID NOs. 9 to 11), SEQ ID NO: 34 (consensus sequence of SEQ ID NOs. 7 and 8), or any other SEQ ID NO. or consensus or seed sequence as shown in Table 2 herein, respectively, wherein one, two, three, four, five or more nucleotides are added, deleted or substituted. Furthermore, in the context of the present invention, a polynucleotide to be employed in context with the present invention may also have a nucleic acid sequence comprising or consisting of the nucleotide sequence of any one of the consensus or seed sequences as shown in Table 2 including one or two nucleotide(s) of the corresponding mature sequence at the 5'-end and/or the 3'-end of the respective consensus or seed sequence, wherein one, two, three, four, five or more nucleotides are added, deleted or substituted. For example, in the context of the present invention, a polynucleotide to be employed in context with the present invention may have a nucleic acid sequence comprising or consisting of the nucleotide sequence U UCAAGU T (i.e. the consensus sequence of SEQ ID NO: 1 plus one nucleotide of the corresponding mature sequence at the 5'-end and one nucleotide of the corresponding mature sequence at the 3'-end, wherein the nucleotide at the 3'-end has been substituted by T). Preferably, in context with the present invention, the addition, deletion or substitution of one, two, three, four, five or more nucleotides is not effected within the seed sequence of a polynucleotide as shown in Table 2 herein. More preferably, in context with the present invention, the addition, deletion or substitution of one, two, three, four, five or more nucleotides is not effected within the consensus sequence of a polynucleotide as shown in Table 2 herein. Also, the polynucleotide described in and to be employed in context with the present invention may comprise or consist of a polynucleotide being at least 25%, 30%, 35%, 40%, 45%, 50%, 55%, 60%, 65%, 70%, 75%, 80%, 85%, 90%, 95%, 97%, 98% or 99% identical to a polynucleotide comprising or consisting of the nucleotide sequence of any one of SEQ ID NO: 1 (miR-26a), SEQ ID NO: 2 (miR-26b), SEQ ID NO: 3 (miR-1297), SEQ ID NO: 4 (miR-222*), SEQ ID NO: 5 (miR-335), SEQ ID NO: 6 (seed sequence of SEQ ID NOs. 1 to 3), SEQ ID NO: 7 (miR-452 human), SEQ ID NO: 8 (miR-452 murine), SEQ ID NO: 9 (miR-106a), SEQ ID NO: 10 (miR-17), SEQ ID NO: 11 (miR-20a), SEQ ID NO: 33 (seed sequence of SEQ ID NOs. 9 to 11), SEQ ID NO: 34 (consensus sequence of SEQ ID NOs. 7 and 8), or any other SEQ ID NO. or consensus or seed sequence as shown in Table 2 herein. Furthermore, in the context of the present invention, a polynucleotide to be employed in context with the present invention may also have a nucleic acid sequence with an identity of at least 25%, 30%, 35%, 40%, 45%, 50%, 55%, 60%, 65%, 70%, 75%, 80%, 85%, 90%, 95%, 97%, 98% or 99% to a polynucleotide comprising or consisting of the nucleotide sequence of any one of the consensus or seed sequences as shown in Table 2 including one or two nucleotide(s) of the corresponding mature sequence at the 5'-end and/or the 3'-end of the respective consensus or seed sequence. For example, in the context of the present invention, a polynucleotide to be employed in context with the present invention may have a nucleic acid sequence with an identity of at least 25%, 30%, 35%, 40%, 45%, 50%, 55%, 60%, 65%, 70%, 75%, 80%, 85%, 90%, 95%, 97%, 98% or 99% to a polynucleotide comprising or consisting of the nucleotide sequence U UCAAGU A (i.e. the seed sequence of SEQ ID NO: 1 plus one nucleotide of the corresponding mature sequence at the 5'-end and one nucleotide of the corresponding mature sequence at the 3'-end).

It is of note that the present invention also provides for other miRs/microRNAs that are useful in the medical intervention of problematic energy homeostasis/obesity etc. as described herein like miR-106a (SEQ ID NO: 9), miR-17 (SEQ ID NO: 10), miR-20a (SEQ ID NO: 11) or a polynucleotide that comprises the common seed sequence of these three miRs, namely the sequence AAAGUG (SEQ ID NO: 33). Also envisaged in the medical intervention of such energy homeostasis disorders is miR452 (SEQ ID NO: 7, human, and SEQ ID NO: 8, murine) or a polynucleotide, like an miR/microRNA that comprises the sequence SEQ ID NO: 34, namely UGUUUGCAGAGGAAACUGA.

Generally, as used herein, a polynucleotide comprising the nucleic acid sequence of a respective SEQ ID NO. may also be a polynucleotide consisting of the nucleic acid sequence of a respective SEQ ID NO.

In context with the determination whether a polynucleotide described in and to be employed in context with the present invention hybridizes to an mRNA of a UCP1-suppressor, to the mRNA of a UCP1-activator, to the promoter of UCP1, or to the promoter of a UCP1-activator, the hybridization may occur and be detected under physiological or artificial conditions, under stringent or non-stringent conditions. Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. In accordance to the invention described herein, low stringent hybridization conditions for the detection of homologous or not exactly complementary sequences may, for example, be set at 6×SSC, 1% SDS at 65° C. As is well known, the length of the probe and the composition of the nucleic acid to be determined constitute further parameters of the hybridization conditions. Polynucleotides to be employed in context with the present invention which hybridize to the mRNA of a UCP1-suppressor or to the mRNA of a UCP1-activator also comprise fragments of the above described polynucleotides which are to be employed in context with the present invention. Such fragments preferably are polynucleotides which are able to induce or upregulate expression of UCP1 and can be used in treating or preventing disorders of the energy homeostasis, like, inter alia, obesity, overweight, adiposity, metabolic syndrome, or diseases or disorders related to energy homeostasis disorders such as diabetes (e.g., diabetes type II), hypercholesterolemia or hypertension as described herein. It is preferred that the agents to be employed in accordance with this invention are capable to negatively interfere concomitantly and independently with at least two UCP1-suppressors and/or inhibitors (suppressors) of the UCP1-promoting insulin signalling pathway. Furthermore, a hybridization complex refers to a complex between two nucleic acid sequences by virtue of the formation of hydrogen bonds between complementary G and C bases and between complementary A and T (or U, respectively) bases; these hydrogen bonds may be further stabilized by base stacking interactions. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T (or U, respectively)" binds to the complementary sequence "T (or U, respectively)-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands.

In order to determine whether a polynucleotide hybridizes to the mRNA of a UCP1-suppressor or UCP1-activator as described hereinabove, thereby inducing degradation or preventing translation of said mRNA of the UCP1-suppressor or inducing transcription, stabilization or translation of said mRNA of the UCP1-activator or inducing transcription, stabilization or translation of mRNA of UCP1 itself, respectively, various tests known in the art and also described herein may be applied. In this context, the hybridization may occur and be tested under physiological conditions or under artificial conditions as known in the art and also described herein. For example, a test to determine hybridization between a miRNA and an mRNA may be a Luciferase Assay as also described in technical bulletins by Promega (C8021 (psiCHECK-2 Vector), E1960 (Dual-Luciferase® Reporter Assay System)). In context with the present invention, general examples of methods suitable to determine whether a polynucleotide hybridizes to another nucleic acid are reporter gene assays in which common reporter genes are used such as fluorescent proteins (e.g., GFP, eGFP, YFP, eYFP, BFP, or eBFP), or luminescent proteins (e.g., *Renilla* or firefly luciferase, or β-galactosidase encoded by the lacZ gene). Furthermore, degradation of mRNA or the level of the respective translation product (to test whether the translation of the mRNA was prevented) can easily be examined by methods known in the art. Examples for methods suitable to examine degradation or stabilization of mRNA are qPCR, RT-PCR, qRT-PCR, RT-qPCR, Light Cycler®, TaqMan® Platform and Assays, Northern blot, dot blot, microarrays, next generation sequencing (VanGuilder, Biotechniques (2008), 44: 619-26; Elvidge, Pharmacogenomics (2006), 7: 123-134; Metzker, Nat Rev Genet (2010), 11: 31-46). Examples for methods suitable to examine whether the translation of a mRNA has been prevented or induced are polyacrylamide gel electrophoresis and related blotting techniques such as Western. Blot paired with chromogenic dye-based protein detection techniques (such as silver or coomassie blue staining) or with fluorescence- and luminescence-based detection methods for proteins in solutions and on gels, blots and microarrays, such as immunostaining, as well as immunoprecipitation, ELISA, microarrays, and mass spectrometry (Western Blot (Burnette, Anal Biochem (1981) 112: 195-203) or ELISA (Crowther, J A. The ELISA Guidebook. Humana Press; Totowa, N.J.: 2001).

In accordance with the present invention, in order to determine whether a polynucleotide induces or upregulates expression of UCP1 (e.g., by hybridizing to the mRNA of a UCP1-suppressor and thereby inducing degradation or preventing translation of UCP1-suppressor mRNA), the level of expressed UCP1 can be easily detected. Without being limited to the following protocol, an agent (for example a polynucleotide, like a microRNA) may be assessed for its capability of inducing or upregulating the expression or biological function of UCP1 when the detected level of expressed UCP1 in a test sample which was contacted with an agent (or example, a polynucleotide like a microRNA) to be tested is at least 1.5 fold, preferably at least 1.75 fold, more preferably at least 2.0 fold, and most preferably at least 2.5 fold higher than the UCP1 expression level of a control sample which was not contacted with said agent. For example, a Western blot analysis may be performed for UCP1 protein detection. For this purpose, whole cell extracts can, inter alia, be prepared as follows: hMADS cells are washed with PBS (pre-cooled to 4° C.) and subsequently harvested using a buffer (pre-cooled to 4° C.) consisting of 25 mM TRIS-HCl (pH 7.4), 100 mM NaCl, 1 mM EDTA, 0.5% Triton X-100, 0.5% NP40, 20 µl/ml PIC (Protease Inhibitor Cocktail from Roche), 0.5 mM Na-orthovanadate, 10 mM NaF and 10 mM β-glycerophosphate. Cell lysates are then homogenized on ice by a 3×10 sec ultrasound treatment at 4° C., followed by centrifugation for 10 min at 4° C. and 16000×g. The pellet and fat cake (if adipocytes) are removed and, subsequently, cell lysates are aliquoted and stored at −20° C. Protein concentrations are determined by the Bradford method (Bio-Rad, France). Subsequently, an SDS-PAGE can be performed as follows: Equal volumes of protein extract consisting of 50-100 µg protein are separated by electrophoresis on 12% polyacrylamide-SDS gels including prestained molecular weight standards in one or more gel lanes (Fermentas, Prestained Protein Ladder). Afterwards a Western blot is carried out. For this purpose, proteins are transferred in 25 mM Tris, 192 mM glycine and 20% ethanol onto PVDF membrane. Blots are blocked for 30 min with TBS (10 mM Tris-HCl pH 7.5 and 150 mM NaCl) plus 0.1% Tween 20 (TBST buffer) containing 5% dried milk powder (blocking buffer). For analysis, the blots are hybridized in the same buffer with specific primary antibodies: rabbit anti-human UCP1 (Calbiochem, dilution 1/1000) at 4° C. overnight and anti-TATA-binding protein (TBP) (Santa-Cruz, 0.2 µg/ml) at room temperature for 2 hrs. The blots are then washed twice with TBST for 5 min each at room temperature and incubated for 1 hr at room temperature in blocking buffer using the appropriate secondary horseradish peroxidase-conjugated antibody (Promega, dilution 1/4000). After 4 washes in TBST for 5 min at room temperature, immunoreactive proteins are visualized using the Enhanced ChemiLuminescence's (ECL) detection kit (Millipore) according to the manufacturer's instructions.

Furthermore, the polynucleotide(s) described in and to be employed in context with the present invention may hybridize to the 3'UTR of the mRNA of a UCP1-suppressor described herein. Examples for such UCP1-suppressors are RB1, NRIP1, RPS6KB1, TWIST1, NCOA2 (TIF2), EIF4EBP1 (4E-BP1), p170, WNT10B, CIDEA, NR2F1 (COUP-TFI), NR2F2 (COUP-TFII), and NR1H3 (LXR) (Hansen and Kristiansen, Biochem J (2006), 398: 153-168). As mentioned, an example of a UCP1-suppressor which suppresses/inhibits the UCP1-promoting insulin signalling pathway is RPS6KB1, while RB1 is an indirect UCP1-suppressor and NRIP1 is a direct UCP1-suppressor in the context of the present invention. In a preferred embodiment, the polynucleotide molecule to be employed in context of this invention inhibits or interferes with at least two UCP1 suppressors and/or an inhibitor/suppressor of the UCP1-promoting insulin signalling pathway. In an even more preferred embodiment, said agent inhibits or interferes with at least three UCP1-suppressors. These "UCP1-suppressors" and/or "suppressors of the UCP1-promoting insulin signalling pathway", in one embodiment, may be selected from the group consisting of RB1, NRIP1, RPS6KB1, TWIST1, NCOA2 (TIF2), EIF4EBP1 (4E-BP1), p170, WNT10B, CIDEA, NR2F1 (COUP-TFI), NR2F2 (COUP-TFII), and NR1H3 (LXR). More preferably, said "UCP1-suppressors" which should be interfered with the agents of the present invention are selected from the group consisting of RB1, NRIP1 and RPS6KB1. Examples of such interfering agents are miRNAs, like the herein described SEQ ID NO: 1 (miR-26a), SEQ ID NO: 2 (miR-26b), SEQ ID NO: 3 (miR-1297) or a miRNA comprising the consensus or seed sequence as shown in SEQ ID NO: 6 (UCAAGU).

As discussed and as illustrated in Table 2 herein, also other agents (e.g. polynucleotides like miRNAs) may be employed in context of this invention in order to treat and/or prevent disorders relating to malfunctioning energy homeostasis like obesity, etc. as described herein. Such molecules have been found in accordance with the present invention to either interfere with the expression and biological function of UCP1-suppressors or suppressors of the UCP-1-promoting insulin signalling pathway (like RB1, NR1PI and/or RPS6KB6) and/or they interfere with the expression and biological function of autophagy-related genes which drive a intracellular catabolic process involving the degradation of a cell's own components through the lysosomal machinery. The polynucleotide(s) described in and to be employed in context with the present invention may hybridize to the 3'UTR of the mRNA of an autophagy related gene (ATG) described herein. Examples for such ATGs are ATG1, ATG2a, ATG2b, ATG5, ATG6, ATG10, ATG11, ATG12, ATG14, ATG15, and ATG16L1. As mentioned above, in context of the present invention, these 11 autophagy-related genes (ATGs) were identified as targets for the miRNAs miR-106a (SEQ ID NO: 9), miR-17 (SEQ ID NO: 10), and miR-20a (SEQ ID NO: 11); cf. also Table 2 herein.

In accordance with the findings of Table 2 herein, other useful agents that interfere with the undesired molecules, i.e. polynucleotides that hybridize to the 3'UTR of a corresponding mRNA may be miR-106a (SEQ ID NO: 9), miR-17 (SEQ ID NO: 10), miR-20a (SEQ ID NO: 11) or a polynucleotide that comprises the common seed sequence of these three miRNAs, namely the sequence AAAGUG (SEQ ID NO: 33).

As also shown in Table 2 as provided herein, also further microRNAs can be employed that target at least two, preferably at least three UCP1-suppressors. An example of such an miR/micro RNA is provided with miR-452, as shown in its human form in SEQ ID NO: 7 and in its murine form in SEQ ID NO: 8.

As mentioned herein, it is also within the gist of the present invention that also microRNAs are used to treat negative effects of energy homeostasis, like, e.g., obesity, which are capable of stabilizing UCP1 activators as mentioned above.

Hybridization between a polynucleotide described in and to be employed in context with the present invention and the 3'UTR of the mRNA of (a) UCP1-suppressor(s)/(an) inhibitor(s) of the UCP1-promoting insulin signalling pathway or of an ATG as described herein can easily be tested as described herein above. However, also other test systems may be employed.

Furthermore, in accordance with the present invention, the polynucleotide(s)/nucleic acid molecule(s) described in and to be employed in context with the present invention may be cloned into a vector. The term "vector" as used herein particularly refers to plasmids, cosmids, viruses, bacteriophages and other vectors commonly used in genetic engineering. In a preferred embodiment, these vectors are suitable for the transformation of cells, like fungal cells, cells of microorganisms such as yeast or prokaryotic cells. In a particularly preferred embodiment such vectors are suitable for stable transformation of bacterial cells, for example to express the polynucleotide of the present invention.

Accordingly, in one aspect of the invention, the vector as provided is an expression vector. Generally, expression vectors have been widely described in the literature. As a rule, they may not only contain a selection marker gene and a replication-origin ensuring replication in the host selected, but also a promoter, and in most cases a termination signal for transcription. Between the promoter and the termination signal there is preferably at least one restriction site or a polylinker which enables the insertion of a nucleic acid sequence/molecule desired to be expressed.

It is to be understood that when the vector provided herein is generated by taking advantage of an expression vector known in the prior art that already comprises a promoter suitable to be employed in context of this invention, for example expression of a polynucleotide as described hereinabove, the nucleic acid construct is inserted into that vector in a manner the resulting vector comprises only one promoter suitable to be employed in context of this invention. The skilled person knows how such insertion can be put into practice. For example, the promoter can be excised either from the nucleic acid construct or from the expression vector prior to ligation.

As a non-limiting example, the vector into which a polynucleotide described herein and to be employed in context with the present invention (i.e. which induces or upregulates UCP1-expression for use in treating or preventing disorders of energy homeostasis such as obesity, overweight, adiposity, metabolic syndrome, or diseases or disorders related to energy homeostasis disorders such as diabetes (e.g., diabetes type II), hypercholesterolemia or hypertension in a subject) is cloned are adenoviral, adeno-associated viral (AAV), lentiviral, HIV-based lentiviral, or nonviral minicircle-vectors. Further examples of vectors suitable to comprise the polynucleotide described in and to be employed in context with the present invention to form the vector described herein are known in the art and are, for example, other vectors for bacterial and eukaryotic expression systems such as pBABE vectors (Addgene Plasmid Repository), or pMSCV (Clontech), or Lenti-miR (SBI System Biosciences).

In an additional embodiment, the agent, in a particular the polynucleotides described in and to employed in context with the present invention and/or the vector into which the polynucleotide described herein is cloned may be transduced, transformed or transfected or otherwise introduced into a host cell. For example, the host cell is a prokaryotic cell, for example, a bacterial cell. As a non-limiting example, the host cell is preferably a mammalian cell: The host cell described herein is intended to be particularly useful for generating the polynucleotide described in and to be employed in context with the present invention.

Generally, the host cell described hereinabove may be a prokaryotic or eukaryotic cell, comprising the polynucleotide described in and to be employed in context with the present invention or the vector described herein or a cell derived from such a cell and containing the nucleic acid construct or the vector described herein. In a preferred embodiment, the host cell comprises, i.e. is genetically modified with the polynucleotide described in and to be employed in context with the present invention or the vector described herein in such a way that it contains the polynucleotide described in and to be employed in context with the present invention integrated into the genome. For example, such host cell described herein may be a bacterial, yeast, or fungus cell. In one particular aspect, the host cell is capable to express or expresses a polynucleotide which induces or upregulates expression of UCP1 in context with the present invention. An overview of examples of different corresponding expression systems to be used for generating the host cell described herein is for instance contained in Methods in Enzymology 153 (1987), 385-516, in Bitter (Methods in Enzymology 153 (1987), 516-544), in Sawers (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), and in Griffiths, (Methods in Molecular Biology 75 (1997), 427-440). The transformation or genetically engineering of the host cell with a polynucleotide described in and to be employed in context with the present invention or vector described herein can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990.

As already mentioned, the present invention also relates to a composition comprising (a) polynucleotide(s) as described herein, i.e. which induce(s)/upregulate(s) expression of UCP1 for use in treating or preventing disorders of the energy homeostasis like obesity, overweight, adiposity, metabolic syndrome, or diseases or disorders related to energy homeostasis disorders such as diabetes (e.g., diabetes type II), hypercholesterolemia or hypertension in a subject.

The composition comprising UCP1-promoting agent like the herein provided polynucleotide(s)/nucleic acid molecule(s) may be administered to a subject in need of medical intervention in an amount of about 1 ng/kg body weight to about 100 mg/kg body weight. Such a subject may be a human who is in need to be treated or in which disorders of energy homeostasis such as obesity, overweight, adiposity, metabolic syndrome, or diseases or disorders related to energy homeostasis disorders such as diabetes (e.g., diabetes type II), hypercholesterolemia or hypertension are to be prevented. In a preferred embodiment of the present invention, the composition comprises the UCP1 up-regulating agent/compound (like the herein described polynucleotides) in an amount of about 1 µg/kg body weight to about 20 mg/kg body weight, more preferably 1 mg/kg body weight to about 10 mg/kg body weight.

The composition comprising agent like (a) polynucleotide(s)/nucleic acid molecule(s) described in and to be employed in context with the present invention, may further comprise a pharmaceutically acceptable carrier. Accordingly, the present invention also relates to a pharmaceutical composition comprising a polynucleotide described in and to be employed in context with the present invention and further comprising a pharmaceutically acceptable carrier, excipient and/or diluent. Generally, examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose, i.e. about 1 ng/kg body weight to about 100 mg/kg body weight of the subject which is to be treated or in which homeostasis disorders such as obesity, overweight, adiposity, metabolic syndrome, or diseases or disorders related to energy homeostasis disorders such as diabetes (e.g., diabetes type II), hypercholesterolemia or hypertension are to be prevented. In a preferred embodiment of the present invention, the composition comprising a polynucleotide described in and to be employed in context with the present invention comprises the polynucleotide in an amount of about 1 µg/kg body weight to about 20 mg/kg body weight, more preferably 1 mg/kg body weight to about 10 mg/kg body weight. Administration of the compositions comprising a polynucleotide described in and to be employed in context with the present invention may be effected or administered by different ways, e.g., enterally, orally (e.g., pill, tablet (buccal, sublingual, orally, disintegrating, capsule, thin film, liquid solution or suspension, powder, solid crystals or liquid), rectally (e.g., suppository, enema), via injection (e.g., intravenously, subcutaneously, intramuscularly, intraperitoneally, intradermally) via inhalation (e.g., intrabronchially), topically, vaginally, epicutaneously, or intranasally. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The compositions comprising a polynucleotide described in and to be employed in context with the present invention may be administered locally or systemically. Administration will preferably be parenterally, e.g., intravenously. The compositions comprising a polynucleotide described in and to be employed in context with the present invention may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, also doses below or above of the exemplary ranges described hereinabove are envisioned, especially considering the aforementioned factors.

The skilled person knows that the effective amount of pharmaceutical composition administered to an individual will, inter alia, depend on the nature of the compound. For example, if said compound is a polynucleotide molecule as described herein, the total pharmaceutically effective amount of pharmaceutical composition administered parenterally per dose will be in the range of about 1 μg/kg/day to 100 mg/kg/day of patient body weight, although, as noted above, this will be subject to therapeutic discretion. More preferably, this dose is at least 0.01 mg/kg/day, and most preferably for humans between about 0.01 and 1 mg/kg/day. The presently recommended dose for polynucleotide molecules lies in a range of between 8 and 80 mg/kg/day. However, this dose may be further decreased subject to therapeutic discretion, in particular if concomitantly certain lipids are applied or if the polynucleotide molecule is subject to certain chemical modifications. If given continuously, the pharmaceutical composition is typically administered at a dose rate of about 1 μg/kg/hour to about 40 μg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect. The particular amounts may be determined by conventional tests which are well known to the person skilled in the art.

Also envisaged herein is the application of the herein described agents (e.g., polynucleotide molecules) using stents. A preferred application form is a drug eluting stent system. This system may be a polymer based drug delivering system or a polymer coated drug delivering system. It is to be understood that the agents such as polynucleotide molecules as described herein are applied to the drug delivering system in combination with (a) polymer(s). Therefore, the drug component (the active ingredient) is embedded in a non-erodible polymer carrier (base coat formulation) which is surrounded by a suitable topcoat layer to control the release of the embedded drug. A possible application form would be a system containing parylene C and the following two non-erodible polymers: polyethylene-co-vinyl acetate (PEVA) and poly n-butyl methacrylate (PBMA). A combination of the two polymers (67%/33%) mixed with polynucleotide molecules makes up the basecoat formulation which is applied to a parylene C treated stent. A drug-free topcoat of PBMA polymer is applied to the stent surface to control the release kinetics of the nucleic acid molecule. Alternatively, a single layer polymer, e.g. a Translute® polymer carrier, might be used as drug delivering matrix. The drug/polymer coating is preferably adhered to the entire surface (i.e. luminal and abluminal) of the stent.

As mentioned, pharmaceutical compositions of the invention may be administered parenterally, orally, rectally, intracisternally, intravaginally, intraperitoneally, topically (as by powders, ointments, drops or transdermal patch), bucally, or as an oral or nasal spray. Preferably, the pharmaceutical compositions of the invention are administered parenterally. The term "parenteral" as used herein refers to modes of administration which include inter alia intravenous, intramuscular, intraperitoneal, intrasternal, subcutaneous and intraarticular injection and infusion. For parenteral administration, the pharmaceutical composition may be formulated generally by mixing it at the desired degree of purity, in a unit dosage injectable form (solution, suspension, or emulsion), with a pharmaceutically acceptable carrier, i.e. one that is non-toxic to recipients at the dosages and concentrations employed and is compatible with other ingredients of the formulation.

The pharmaceutical composition described and provided herein may be also suitably administered by sustained release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP-A1 58481), copolymers of L-glutamic acid and gamma-ethyl-L-glutamate (Sidman, Biopolymers (1983), 22: 547-556), poly(2-hydroxyethyl methacrylate) (Langer, J Biomed Mater Res (1981), 15: 167-277; Langer, Chem Tech (1982), 12: 98-105), ethylene vinyl acetate (Langer, loc. cit.) or poly-D-(–)-3-hydroxybutyric acid (EP-A1 133988). Sustained release pharmaceutical compositions may also include liposomally entrapped compounds. Liposomes containing the pharmaceutical composition may be prepared by methods known in the art, such as described in DE 3218121; Epstein, Proc Natl Acad Sci USA (1985), 82: 3688-3692; Hwang, Proc Natl Acad Sci USA 77: 4030-4034 (1980); EP-A1 52322; EP-A1 36676; EP-A1 88046; EP-A1 143949; EP-A1 142641; Japanese Pat. Appl. 83-118008; U.S. Pat. Nos. 4,485,045 and 4,544,545; and EP-A1 102324. Ordinarily, the liposomes may be of the small (about 200-800 Å (Angstroms)) unilamellar type in which the lipid content is greater than about 30 mol percent cholesterol, the selected proportion being adjusted for the optimal therapy.

Generally, in context of the present invention, the formulations described herein may be prepared by contacting the components of the pharmaceutical composition uniformly and intimately with liquid carriers or finely divided solid carriers or both. Then, if necessary, the product may be shaped into the desired formulation. Preferably, the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate may also be useful herein, as well as liposomes as described herein. The carrier may suitably contain minor amounts of additives such as substances that enhance isotonicity and chemical stability. Such materials are preferably non-toxic to recipients at the dosages and concentrations employed, and may include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

In context of the present invention, the components of the pharmaceutical composition to be used for therapeutic administration are preferably sterile. Sterility may readily be accomplished by, e.g., filtration through sterile filtration membranes (e.g., 0.2 micron membranes). Therapeutic components of the pharmaceutical composition may be placed into a container having a sterile access port, for example, an intravenous solution bag or vial having a stopper pierceable by a hypodermic injection needle. The components of the pharmaceutical composition ordinarily may be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

In context of the present invention, the polynucleotide molecules may for example be delivered as follows: the polynucleotide molecules may be injected directly into a cell, such as by microinjection. Alternatively, the molecules may be contacted with a cell, preferably aided by a delivery system. Useful delivery systems include, for example, liposomes and charged lipids. Liposomes typically encapsulate oligonucleotide molecules within their aqueous center. Charged lipids generally form lipid-oligonucleotide molecule complexes as a result of opposing charges. These liposomes-oligonucleotide molecule complexes or lipid-oligonucleotide molecule complexes are usually internalized in cells by endocytosis. The liposomes or charged lipids may comprise helper lipids which disrupt the endosomal membrane and release the oligonucleotide molecules.

Generally, for administration of polynucleotides, e.g. miRNAs as described herein, techniques as employed and known for other polynucleotides used in silencing target gene expression such as siRNA may be carried out. Such techniques comprise, e.g., chemically modified siRNA, viral siRNA vectors and nonviral siRNA carriers. For example, various molecular positions in siRNA may be chemically replaced or modified, mainly to resist enzymatic hydrolysis, e.g. phosphodiester ($PO_4$) linkages were replaced with phosphothioate (PS) at the 3'-end, introducing O-methyl (2'-O-Me), fluoro (2'-F) group or methoxyethyl (2'-O-MOE) group greatly prolonged half-lives in plasma and enhanced RNAi efficiency in cultured cells. In addition, efficiency enhancer molecules, e.g., cholesterol, were conjugated to either the 5'- or 3'-end of the sense strand, without affecting the activity of the antisense strand. Nonviral carriers comprise polymers, peptides, and liposome-based nanoparticles. Liposome-based nanoparticles may be of special interest as they are produced by natural phospholipids which diminish toxic effects, they encapsulate the polynucleotide to be delivered, thereby protecting the polynucleotide from degradation, and they have already been shown to deliver antibiotics and chemotherapeutics. Based on a large variety of phospholipids, the properties of liposome-based nanoparticles (size, shape, charge, structure) may be individually adapted as known by the person of skill in the art. Moreover, the surface may be modified and functionalized and polymer wrapping of the liposomes can stabilize the nanoparticles and can make them biocompatible. In addition, signalling molecules (optical markers, radionuclides, paramagnetic substances) may be coupled to the nanoparticle. Thus, liposome-based delivery systems may fulfill several functions such as delivery, targeting, and imaging of polynucleotides (e.g., miRNAs) as described herein (Shim, FEBS J. (2010), 277: 4818-4827; Samad, Curr Drug Deliv (2007)m 4: 297-305; Baker, Nature (2010), 464: 1225-1228). As mentioned, in context of the present invention, the techniques described herein may also be employed for administration of the polynucleotides (e.g., miRNAs) as described herein. Enhanced specificity and efficiency of miRNAs in vivo via selective accumulations in desired tissues, specific binding to target cells and facilitated intracellular trafficking may also be achieved by utilizing targeting moieties, cell-penetrating peptides, fusogenic peptides or stimuli-responsive polymers.

Other methods for introducing polynucleotide molecules as described herein and to be employed in context with the present invention into a cell may include use of delivery vehicles, such as dendrimers, biodegradable polymers, polymers of amino acids, polymers of sugars, and oligonucleotide-binding- and/or liposome-based nanoparticles as described herein. In addition, pluoronic gel as a depot reservoir may be used to deliver the anti-microRNA oligonucleotide molecules over a prolonged period. The above methods are generally known in the art and are exemplarily described in, inter alia, Hughes, Drug Discovery Today (2001), 6: 303-315; Liang, Eur J Biochem (2002), 269: 5753-5758; Becker, In Antisense Technology in the Central Nervous System (Leslie, R. A., Hunter, A. J. & Robertson, H. A., eds), pp. 147-157, Oxford University Press. Targeting of polynucleotide molecules to a particular cell may be performed by any method known to those skilled in the art. For example, polynucleotide molecules can be conjugated to an antibody or ligand specifically recognized by receptors on the cell. For example, the ligand can be DDR2 (discoid domain receptor 2) expressed on fibrotic cells. Alternatively, an antibody to DDR2 (discoid domain receptor 2) may be employed.

As already mentioned, the compositions described herein comprising an agent like the herein described polynucleotide(s) which induce(s) or upregulate(s) expression of UCP1 can be used to treat or prevent disorders of energy homeostasis like obesity, overweight, adiposity, metabolic syndrome, or related diseases or disorders related to energy homeostasis disorders such as diabetes (e.g., diabetes type II), hypercholesterolemia or hypertension in a subject. Generally, in context of the present invention, the composition may comprise two, three or more agents, e.g., polynucleotides described herein and to be employed in context of this invention.

Generally, in context of the present invention, obesity is not only and merely to be considered as a single disorder but can also be see as a heterogeneous group of conditions with (potential) multiple causes. Therefore, obesity is also characterized by elevated fasting plasma insulin and an exaggerated insulin response to oral glucose intake (Kolterman, J Clin Invest (1980), 65: 1272-1284). Yet, clear relationship and dependence of obesity with and towards secondary disorders, i.e. related diseases and disorders, have been established, like for example for diabetes mellitus type II (Kopelman, Nature (2000), 404: 634-643; Colditz, Arch Int Med (1995), 122: 481-486). Rare (genetic) obesity diseases are also to be treated in accordance with this invention, for example disorders linked to so-called "obesity mutations" such as in the "ob-gene" (leptin), "fat-gene" (carboxypeptidase E) or "tubby-gene" (tubby protein).

Further clinical symptoms or disorders may be treated with the means and methods of the present invention, like Prader-Willi, Cohen, Alstrom, Bardet-Biedl or Borjeson-Forssman-Lehman, The "human obesity gene map" comprises entries for more than 40 genes and 15 chromosomal regions in which published studies indicate a possible relationship to adiposity or a related phenotype (Barsh, Nature (2000), 404: 644-650; Perusse, Obes Res (1999), 7: 111-129).

The epidemic of obesity is largely responsible for the high prevalence of the metabolic syndrome in the industrialized world. Since 2001, with the development of the metabolic syndrome classification, simple pragmatic criteria have been available that can be applied in primary care across all continents to diagnose the syndrome (Table 3). The metabolic syndrome, also known as syndrome X or insulin resistance syndrome, is characterized by a cluster of related biochemical and anthropometric features that include central obesity, glucose intolerance or diabetes, hypertension and dyslipidaemia (Strazzullo, Metabolism (2008), 57: 355-61). It is now clear that the metabolic syndrome represents a condition of insulin resistance and ectopic fat accumulation. It is sometimes associated with other conditions such as nonalcoholic fatty liver disease (Tamura, J Clin Invest (2005), 115: 1139-1142; Vanni, Dig Liver Dis (2010), 42: 320-330). Moreover, the widespread use of highly active antiretroviral therapy has led to a serious clinical problem combining peripheral lipoatrophy, central adiposity, insulin resistance, and dyslipidemia, in which adipose tissue is very likely a key factor that contributes to several clinical aspects reminiscent of the metabolic syndrome (Domingo, Clin Infect Dis (2010), 50: 1033-40). Regarding the Cushing's disease, which derives from an exaggeration of the physiological actions of cortisol, it is characterized among various disturbances by central obesity, arterial hypertension, diabetes and hyperlipidemia which are also reminiscent of the metabolic syndrome (Iwasaki, Mol Cell Endocrinol (2008), 285: 10-18). Accordingly, the methods and the compositions comprising a polynucleotide as described in and to be employed in context with the present invention can inter alia be used to treat, prevent or ameliorate the characteristic manifestations of the metabolic syndrome which includes obesity, fat tissue redistribution as observed in Cushing's disease and during highly active anti-retroviral therapy of HIV patients, insulin resistance, type 2 diabetes, hypertension and dyslipidemia.

TABLE 3

NCEP ATPIII, National Cholesterol Education Program, third Adult Treatment Panel (2004); WHO, World Health Organization (1999); IDF, International Diabetes Federation (2005)

| Criteria | NCEP ATPIII | WHO | IDF |
|---|---|---|---|
| Central obesity (waist circumference or hip:waist-ratio) | >102 cm (men); >88 cm (women) | waist:hip-ratio: >0.9 (men); >0.85 (women); and/or BMI >30 kg/m² | ≥94 cm (men); ≥80 cm (women) |

TABLE 3-continued

NCEP ATPIII, National Cholesterol Education Program, third Adult Treatment Panel (2004); WHO, World Health Organization (1999); IDF, International Diabetes Federation (2005)

| Criteria | NCEP ATPIII | WHO | IDF |
|---|---|---|---|
| Fasting plasma glucose concentration (mmol/l) | >5.6 mmol/l (>110 mg/dl) | ≥6.1 mmol/l (≥120 mg/dl) or ≥7.8 mmol/l (2 hour plasma glucose or previously diagnosed type 2 diabetes) | ≥5.6 mmol/l or previously diagnosed type 2 diabetes |
| Blood pressure (mm Hg) | >130/85 | ≥140/90 | ≥130/85 |
| Fasting triglyceride concentration (mmol/l) | ≥1.7 mmol/l (150 mg/dl) | ≥1.7 mmol/l | ≥1.7 mmol/l |
| HDL cholesterol concentration (mmol/l) | <1.0 mmol/l (men) (<45 mg/dl); <1.3 mmol/l (women) (<50 mg/dl) | ≤0.9 mmol/l (men) (35 mg/dl); ≤1.0 mmol/l (women) (39 mg/dl) | <1.03 mmol/l (men); <1.29 mmol/l (women) |

The polynucleotides (e.g., miRNAs) described herein to be employed in the medical uses described and provided herein may be administered by different routes and in dosages as described herein above.

The Figures show:

FIG. 1: miR-26a expression in murine white (WAT) and brown (BAT) adipose tissue. miR-26a levels of white and brown adipose tissue (pooled from 6 mice) were measured by qRT-PCR using the TaqMan miRNA Assay (ABI) with snoRNA-202 as housekeeping reference. miR-26a expression is around 80% higher in BAT compared to WAT. WAT: white adipose tissue; BAT: brown adipose tissue.

FIG. 2: A. UCP1 mRNA level in hMADS-3 cells during adipocyte differentiation. miR-26a mimics were transfected two days before induction of adipogenic differentiation as described in Example 1 (final concentration: 5 nM), and UCP1 mRNA (NCBI Reference Sequence: NM_021833.4) levels were determined by qRT-PCR as described in Example 1, using TBP mRNA (NCBI Reference Sequence: NM_003194.4) as internal reference, and are presented normalized to the non-targeting control (miR-NTC) at brown adipocyte differentiation ((B)AD) with 16 days of rosiglitazone treatment. Primer sequences used for qRT-PCR are provided in Table 4 (primer names: hUCP1, hTBP). miR-26a overexpression significantly increased UCP1 expression at day 9 and 16 of white adipocyte differentiation ((W)AD: rosiglitazone treatment until day 9). 16 days of rosiglitazone treatment strikingly induced UCP1 mRNA levels, and on top of that, miR-26a mimic transfection 2 days before induction of differentiation increased UCP1 mRNA levels additionally by ~60% (notably 18 days after miR-26a transfection). R9/R16: rosiglitazone treatment until day 9/16 of differentiation; d9/d16: cell harvesting at day 9/16; NTC: non-targeting control; CO: untreated cells ('cells only'); AD: adipocyte differentiation; (W)AD: white adipocyte differentiation; (B)AD: brown adipocyte differentiation.

B. UCP1 protein levels in hMADS-3 cells during adipocyte differentiation. miR-26a mimic transfection 2 days before differentiation (as described in FIG. 2A and Example 1) induced UCP1 mRNA and protein expression at day 9 and 16 of adipocyte differentiation. As shown previously, Rosiglitazone treatment until day 16 strongly induced UCP1 mRNA and protein expression (Elabd, Stem Cells (2009), 27: 2753-2760), but interestingly, miR-26a overexpression even enforced that already strong UCP1 protein expression. Thus, the inducing effect of miR-26a (in combination with continuous rosiglitazone treatment) on UCP1 is similar on mRNA and protein level. R9/R16: rosiglitazone treatment until day 9/16 of differentiation; d9/d16: cell harvesting at day 9/16; NTC: non-targeting control; CO: untreated cells ('cells only'); AD: adipocyte differentiation; Rosi: rosiglitazone; (W)AD: white adipocyte differentiation; (B)AD: brown adipocyte differentiation.

FIG. 3: UCP1 mRNA levels at day 9 (A) and 11 (B) of adipogenic differentiation upon miR-26a silencing. hMADS-3 cells were transfected at day-2 with various concentrations of miR-26a ASO (final concentration between 5 and 25 nM), followed by induction of adipogenic differentiation at day 0, and cells were harvested for RNA extraction at day 9 and 11. Relative UCP1 mRNA (NCBI Reference Sequence: NM_021833.4) levels were measured by qRT-PCR using TBP gene as housekeeping reference. Primer sequences used for qRT-PCR are provided in Table 4 (primer names: hUCP1, hTBP). All procedures were performed as described in Example 1. ASO: antisense oligonucleotide; NTC: non-targeting control.

FIG. 4: Induction of UCP1 RNA levels in mature human adipocytes. hMADS-3 cells were differentiated to the adipogenic lineage with rosiglitazone treatment until day 9 followed by miR-NTC/26a transfection (final concentration: 5 nM) at day 12 with two different transfection systems (HPF: HiPerFect, IFN: Interferin) as described in Example 1. 5 days after transfection (day 17 of differentiation), adipocytes were harvested to isolate total RNA for analysis of UCP1 mRNA (NCBI Reference Sequence: NM_021833.4) by qRT-PCR as described in Example 1, using TBP mRNA (NCBI Reference Sequence: NM_003194.4) as internal reference. miR-26a was able to increase UCP1 mRNA expression. Primer sequences used for qRT-PCR are provided in Table 4 (primer names: hUCP1, hTBP).

FIG. 5: Direct miR-26a binding to the 3'UTR of RB1.
A. Predicted binding site for miR-26a in the 3'UTR of RB1 (TargetScanHuman 5.1; seed match in bold);
B. Conservation of the miR-26a binding region in the RB1 3'UTR among different species (TargetScanHuman 5.1; seed match in bold);
C. The psiCHECK-2 vector construct containing the RB1 3'UTR was generated and co-transfected into HEK293 cells with 50 nM miR-NTC or miR-26a mimic as described in Example 1. *Renilla* luciferase activity was normalized to firefly luciferase. Data shown as mean value±SEM are derived from three independent experiments and are presented relative to transfection with miR-NTC.

FIG. 6: Direct miR-26a binding to the 3'UTR of NRIP1.
A. Predicted binding site for miR-26a in the 3 VTR of NRIP1 (TargetScanHuman 5.1; seed match in bold);
B. Conservation of the miR-26a binding region in the NRIP1 3'UTR among different species (TargetScanHuman 5.1; seed match in bold);
C. The psiCHECK-2 vector construct containing the NRIP1 3' UTR was generated and co-transfected into HEK293 cells with 50 nM miR-NTC or miR-26a mimic as described in Example 1. *Renilla* luciferase activity was normalized to firefly luciferase. Data shown as mean value±SEM are derived from three independent experiments and are presented relative to transfection with miR-NTC.

FIG. 7: Direct miR-26a binding to the 3'UTR of RPS6KB1.
A. Predicted binding site for miR-26a in the 3'UTR of RPS6KB1 (http://www.microrna.org; seed match in bold);

B. The psiCHECK-2 vector construct containing the RPS6KB1 3'UTR was generated and co-transfected into HEK293 cells with 50 nM miR-NTC or miR-26a mimic as described in Example 1. *Renilla* luciferase activity was normalized to firefly luciferase. Data shown as mean value±SEM are derived from three independent experiments and are presented relative to transfection with miR-NTC.

Figures 8, 9:
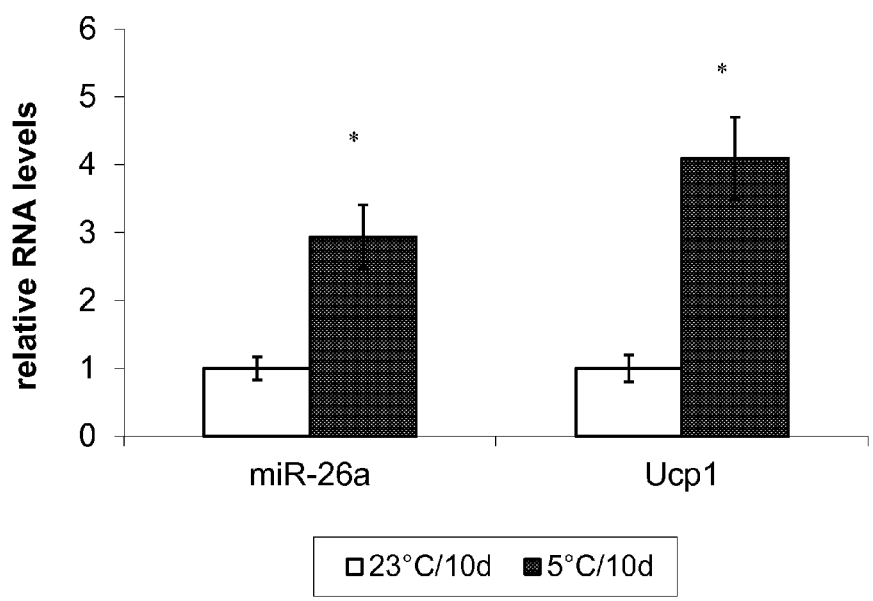

FIG. 8: Consensus sequence for miR-26a, miR-26b, and miR-1297. miR-26a, miR-26b, and miR-1297 share a consensus sequence at nucleotide positions 1-10 and 12-15 (in bold) including the miRNA seed (position 2-7, underscored), the core sequence for target mRNA identification.

FIG. 9: miR-26a and UCP1 levels in vivo in murine WAT upon cold exposure. Female NMRI mice (age 8-12 weeks, n=7) were housed at 23° C. or 5° C. After 10 days, mice were sacrificed to isolate total RNA from intra-abdominal white adipose tissue (WAT) depots as described in Example 1. miR-26a levels were quantified by qRT-PCR relative to U5G small nuclear RNA (RNU5G, NCBI Reference Sequence: NR_002852.2) as reference RNA using the miRCURY LNA Universal RT microRNA System (Exiqon) as described in Example 1. UCP1 mRNA (NCBI Reference Sequence: NM_009463.3) levels were quantified relative to ubiquitously expressed transcript (Uxt, NCBI Reference Sequence: NM_013840.3) as reference RNA by qRT-PCR as described in Example 1, using self-designed primers (primer names: mUcp1, mUxt; see Table 4). Data is presented as means±SEM and relative to mice at 23° C. Differences in means between mice at 23° C. and 5° C. were analyzed by Student's t-test; p<0.01; *p<0.001. miR-26a levels were significantly elevated in vivo in murine WAT upon cold exposure, in parallel to UCP1 as positive control confirming the physiological response of murine WAT to cold stress.

Figure 10:
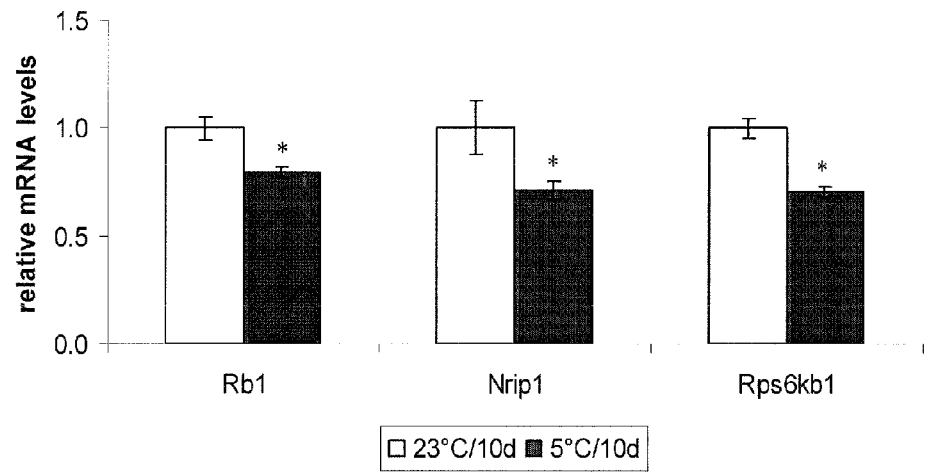

FIG. 10: Diminished gene expression levels of direct miR-26a targets RB1, NRIP1, RPS6LB1 in murine WAT upon cold exposure. Female NMRI mice (age 8-12 weeks, n=7) were housed at 23° C. or exposed to 5° C. After 10 days, mice were sacrificed to isolate total RNA from intra-abdominal white adipose tissue (WAT) depots as described in Example 1. Rb1 (NCBI Reference Sequence: NM_009029.2), Nrip1 (NCBI Reference Sequence: NM_173440.2), and Rps6kb1 (NCBI Reference Sequence: NM_028259.4) mRNA levels were quantified relative to ubiquitously expressed transcript (Uxt, NCBI Reference Sequence: NM_013840.3) as reference RNA by qRT-PCR as described in Example 1, using self-designed primers (primer names: mRb1, mNrip1, mRps6kb1, mUxt; see Table 4). Data is presented as means±SEM and relative to mice at 23° C. Differences in means between mice at 23° C. and 5° C. were analyzed by Student's t-test; *p<0.05; p<0.01; *p<0.001. Cold exposure evoked diminished expression levels of three direct miR-26a targets in murine WAT, RB1, NRIP1, RPS6KB1, all three known UCP1-suppressors as described herein.

Figure 11:
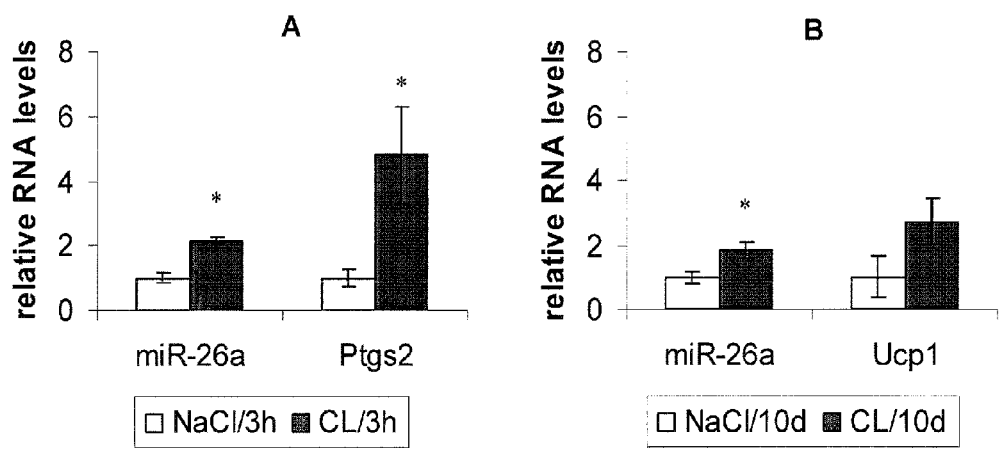

FIG. 11: Elevated in vivo miR-26a levels in murine WAT upon β3-adrenergic stimulation. Female NMRI mice (age 8-12 weeks, n=5) were subjected (A) to a single intraperitoneal injection of the β3-adrenoceptor agonist CL316243 (1 mg/kg; Tocris Bioscience) or vehicle (NaCl) and sacrificed 3 h later, or (B) to a daily intraperitoneal injection of CL316243 (1 mg/kg) or NaCl and sacrificed after 10 days. Total RNA was isolated from intra-abdominal WAT depots as described in Example 1. miR-26a levels were quantified by qRT-PCR relative to U5G small nuclear RNA (RNU5G, NCBI Reference Sequence: NR_002852.2) as reference RNA using the miRCURY LNA Universal RT microRNA System (Exiqon) as described in Example 1. UCP1 (NCBI Reference Sequence: NM_009463.3) and Ptgs2 (NCBI Reference Sequence: NM_011198.3) mRNA levels were quantified relative to ubiquitously expressed transcript (Uxt, NCBI Reference Sequence: NM_013840.3) as reference RNA by qRT-PCR as described in Example 1, using self-designed primers (primer names: mUcp1, mPtgs2, mUxt; see Table 4). Data is presented as means±SEM and relative to vehicle-treated mice. Differences in means between mice treated with CL316243 or NaCl were analyzed by Student's t-test; *p<0.05; p<0.01; *p<0.001. CL:CL316243. Short- and long-term beta3-adrenergic stimulation of mice in vivo elevated miR-26a levels in murine WAT.

Figure 12:
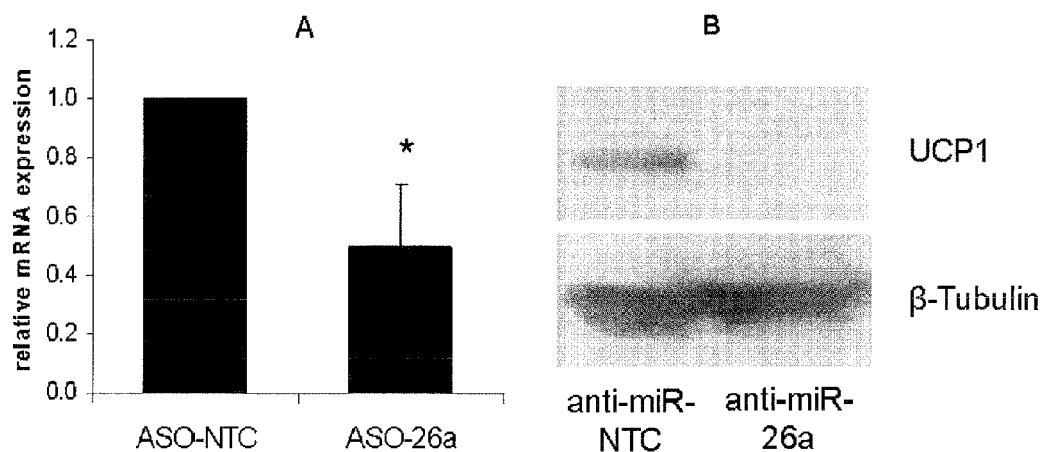

FIG. 12: Repressed mRNA levels and depleted protein levels of UCP1 in hMADS adipocytes upon miR-26a inhibition. hMADS-2 cells were transfected at confluence with 25 nM LNA-based miR-26a antisense oligonucleotide (ASO-26a) or control oligonucleotide (ASO-NTC) as described in Example 1. Brown adipocyte differentiation (with continuous rosiglitazone treatment) was induced 2 days later as described in Example 1. (A) At day 16, total RNA was isolated and UCP1 mRNA (NCBI Reference Sequence: NM_021833.4) levels were quantified relative to TBP mRNA (NCBI Reference Sequence: NM_003194.4) as reference RNA by qRT-PCR as described in Example 1, using self-designed primers (primer names: hUCP1, hTBP; see Table 4). Data is presented as means±SEM and relative to ASO-NTC transfected cells. (B) At day 16, protein expression of UCP1 and β-Tubulin as loading control were assayed via. Western Blot. miR-26a inhibition diminished UCP1 mRNA induction and abolished UCP1 protein induction, thereby showing that rosiglitazone mediated UCP1 induction is dependent on miR-26a.

Figure 13:
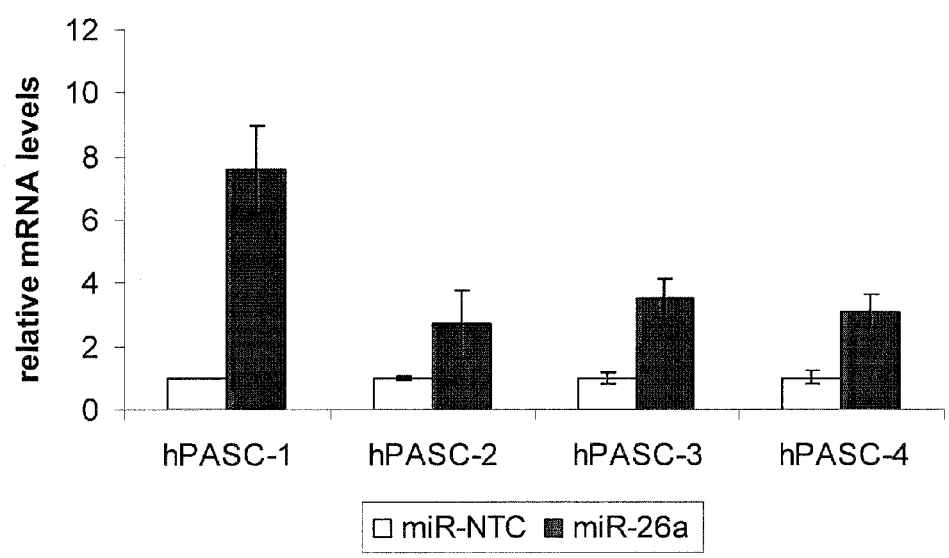

FIG. 13: Increased UCP1 mRNA levels in hPASCs of adult donors upon miR-26a overexpression. Human primary adipose derived stromal cells (hPASCs) were isolated from the stromal vascular fraction (SVF) of human subcutaneous white adipose tissue (WAT) as described in Example 1. Four independent hPASC isolations from different donors (hPASC-1-hPASC-4, donor age between 31 and 47 years) were prepared at different days. At confluence, hPASCs were transfected with 5 nM miR-26a mimic or a non-targeting control (miR-NTC), and adipocyte differentiation was induced two days later as described in Example 1. After 16 days, cells were harvested to isolate total RNA as described in Example 1. UCP1 mRNA (NCBI Reference Sequence: NM_021833.4) levels were quantified relative to TBP mRNA (NCBI Reference Sequence: NM_003194.4) as reference RNA by qRT-PCR as described in Example 1, using self-designed primers (primer names: hUCP1, hTBP; see Table 4). Data is presented as means±SEM and relative to miR-NTC transfected cells. miR-26a increased the expression of UCP1 mRNA levels in hPASCs of adult, middle-aged donors.

Figure 14:
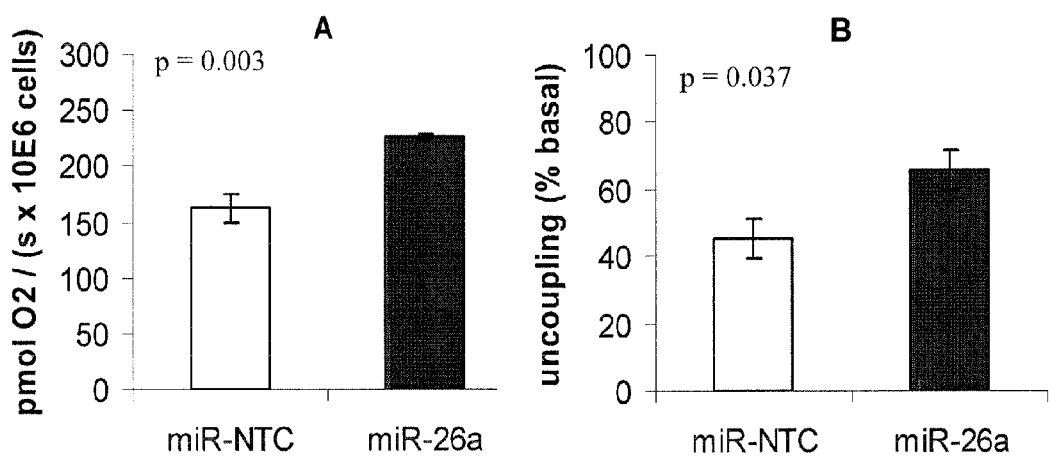

FIG. 14: Increased basal and uncoupled respiration of hMADS adipocytes upon miR-26a overexpression. hMADS-2 cells were transfected at confluence with 5 nM miR-26a mimic or non-targeting control (miR-NTC) as described in Example 1. Brown adipocyte differentiation (with continuous rosiglitazone treatment) was induced 2 days later. At day 16, respiration of adipocytes ($5 \times 10^5$ cells per measurement) was determined using a luminescent oxygen microsensor as described in Example 1. (A) Basal respiration was defined as antimycin A-sensitive respiration. (B) Uncoupled respiration was measured after addition of oligomycin and is expressed relative to basal respiration. Data is presented as mean±SEM of 4-5 independent experiments (where each experiment consisted of 3 independent measurements of each miR-26a and miR-NTC transfected cells). Differences in means between miR-26a and miR-NTC transfected cells were analyzed by Student's t-test. miR-26a overexpression resulted in increased basal and uncoupled respiration of hMADS adipocytes in order to augment energy expenditure.

THE EXAMPLES ILLUSTRATE THE INVENTION

Example 1

Methods

Cell Culture.

Human multipotent adipose-derived stem (hMADS) cells were isolated from the stromal-vascular fraction of white adipose tissue of young donors (Rodriguez, Biochem Biophys Res Comm (2004), 315: 255-263). Two cell populations, termed hMADS-2 and hMADS-3 cells respectively, were used for cell culture experiments which were proliferated in 100 mm cell culture dishes (Greiner Bio-One, Cat. no. 664160). Cells were cultivated in proliferation medium (PM), consisting of Dulbecco's modified Eagle's medium (Lonza, Cat. no. BE12-707F), 10 mM HEPES (Invitrogen, Cat. no. 15630-122), 2 mM L-Glutamine (Invitrogen, Cat. no. 25030024), 10% Fetal Bovine Serum (FBS, Pan Biotech, Cat. no. P30-3300 (lot no. P250330)), 2.5 ng/ml human Fibroblast Growth Factor (hFGF2, Sigma, Cat. no. F0291), and 100 µg/ml Normocin (Invivogen, Cat. no. ant-nr-2). For experiments, cells were seeded in 6-well and 12-well plates (greiner bio-one, Cat. nos. 657160 and 665180) and PM was exchanged every other day. For some experiments. 24-well Multiwell Plates (Corning, Cat. no. 3524) or 96-well Multiwell Plates (Corning, Cat. no. 3596) were used. When cells reached confluence, hFGF2 was omitted from PM. Two days post confluence, adipogenic differentiation was induced by cultivation of cells in differentiation medium (DM), consisting of DMEM/Ham's F12 (Lonza, Cat. no. BE12-615F), 5 mM HEPES, 2 mM L-Glutamine, 100 µg/ml Normocin, 5 µg/ml human Insulin (Sigma, Cat. no. 19278), 10 µg/ml apo-Transferrin (Sigma, Cat. no. T2252), 0.2 nM triiodothyronine (T3, Sigma, Cat. no. T0281), 100 isobutyl-methylxanthine (IBMX, VWR, Cat. no. CALB410957-1), 1 µM Dexamethasone (Sigma, Cat. no. D4902), and 100 nM Rosiglitazone (Cayman Chemicals, Cat. no. 71740). After three days, medium was changed to DM lacking IBMX and Dexamethasone. Subsequently, medium was changed every other day, and differentiation was directed towards white or brown adipogenesis, either by omitting Rosiglitazone from DM at day 9, or continuing Rosiglitazone treatment, respectively.

HEK293 cells were cultivated in DMEM supplemented with 4 mM L-Glutamine, 10% FBS and Normocin. During transfection experiments, Normocin was omitted from the medium.

miRNA Microarray Analysis.

MiRNA microarrays were produced by spotting the miR-CURY™ LNA microRNA Array ready-to-spot probe set 208010-A (Exiqon) on epoxy-coated glass slides (Nexterion, Schott, ordered by Peqlab, #39-1125813) with eight replicate spots for each sequence using the microarrayer MicroGrid II (Zinsser Analytic). Microarray production was performed according to the supplier's instruction manual and recommendations provided by Exiqon. RNA was isolated with TRIzol reagent from hMADS cells that were differentiated to white or brown adipocytes (see below for RNA isolation procedure). 5 µg total RNA from undifferentiated, proliferating hMADS cells as reference and from white and brown adipocyte samples (day 9 and day 17 of differentiation) were tagged for labeling with Hy3 and Hy5 dyes, respectively, by using the miRCURY™ LNA microRNA Hy3/Hy5 Power labeling kit (Exiqon, Cat. no. 208032) according to manufacturer's instructions. All hybridizations were performed according to manufacturer's (Exiqon) instructions and repeated with reversed dye assignment (dye-swap). Hybridized slides were scanned with GenePix 4000B microarray scanner (Axon Instruments) at 10 µm resolution. The resulting TIFF images for each of the two fluorophores were analyzed with GenePix Pro 4.1 (Axon Instruments). After image acquisition and filtering the data for low intensity, inhomogeneity and satured spots, the results files were normalized with the in-house developed software ArrayNorm (Pieler, Bioinformatics (2004), 20: 1971-1973). After background correction, the data sets were normalized by global-mean and dye-swap pair normalization. The obtained result files were used for cluster analyses using the Genesis software tool (Sturn, Bioinformatics (2002), 18: 207-208). As cut-off for differential expression, we chose 1.3 fold ($\log_2$ ratio>|0.378|) as previously described to be able to reliably identify differentially expressed transcripts (Wurmbach, Methods (2003), 31: 306-316). For comparisons, data were expressed as $\log_2$ ratios. miRNA microarray experiments were carried out at the Microarray Facility, Institute for Genomics and Bioinformatics, Graz University of Technology, Graz, Austria.

Transfection.

hMADS cells were transfected with miRIDIAN microRNA mimics (hsa-miR-26a, Cat. no. C-300499-05-0005, or Negative Control #1, Cat. no. CN-001000-01-20; Dharmacon) or miRIDIAN microRNA Hairpin Inhibitors (hsa-miR-26a, Cat. no. IH-300499-06, or Negative Control #2, Cat. no. IH-300000-05; Dharmacon), or LNA antisense oligonucleotides (anti-hsa-miR-26a Exiqon, Cat. no. 138463-00, control oligonucleotide, Cat. no. EQ 866923, Exiqon) using HiPerFect Transfection Reagent (QIAGEN, Cat. no. 301707) or Interferin (Polyplus, Cat. no. 409-01) based on manufacturer's instructions. Briefly, medium was changed one hour before transfection. Subsequently, 20 µM oligonucleotide stock solutions were diluted with RNase-free water to reach the desired concentrations, and for each well (12-well plate), 3 µl oligonucleotide solution was mixed with 97 µl DMEM (without FBS and antibiotics) and 6 µl HiPerFect or Interferin. After incubation at room temperature for 10 min, transfection mixture was added dropwise on the cells. Transfection mixture was removed after 2 days by regular medium changes.

qRT-PCR.

Total RNA was prepared using TRIzol reagent (Invitrogen, Cat. no. 15596018) following manufacturer's instructions. For RNA harvest from cells, medium was aspirated, cells were washed once with Phosphate buffered saline (PBS, Invitrogen Cat. no. 10010015), and 400 µL TRIzol Reagent were added to each well of a 12-well-plate (3 ml per 100 mm cell culture dish). For RNA harvest from murine WAT samples, tissue was placed in 15 mL PP centrifuge tubes and immediately frozen in liquid N2. Subsequently, 2 mL TRIzol Reagent per g tissue were pipetted onto the frozen samples, followed by homogenization with the Ultra-TURRAX T25 (IKA). Samples were usually stored at −80° C. between harvest and RNA isolation and therefore thawed at room temperature for 35 min. After addition of 0.2 mL chloroform (Sigma, Cat. no. C2432) per mL TRIzol Reagent, samples were shaked vigorously for 2 min, incubated for 3 min at room temperature, and centrifuged for 17 min at 4° C. and $1.2 \times 10^4$ g using a Microcentrifuge 5415R (Eppendorf). Subsequently, the upper (aqueous) phase was pipetted into new 1.5 mL Safe-Lock tubes (Eppendorf, Cat. no. 0030 123.328), and 0.5 mL 2-propanol (Roth, Cat. no. 7343.1) per mL TRIzol Reagent were added. Samples were mixed and incubated for 10 min at room temperature before centrifugation for 20 min at 4° C. and $1.2 \times 10^4$ g. The supernatant was decanted and 1 mL 75% Ethanol (AustrAlco, Cat. no. UN1770, diluted with DEPC-treated H2O) per mL TRIzol reagent were added to the RNA pellet. After centrifugation for 8 min at 4° C. and 7600 g, the supernatant was decanted and the tubes were incubated for 10 min with open caps to allow evaporation of residual Ethanol. Finally, RNA was dissolved in 10-25 µL DEPC-treated $H_2O$ (depending on pellet size) and incubated at 55° C. for 10 min. RNA concentration and purity were determined by spectrophotometry using the NanoDrop ND-1000 (Thermo Scientific). RNA was stored at −80° C. 0.5-1 µg of RNA were DNase digested with RQ1 RNase-free DNase (Promega, Cat. no. M6101). Briefly, total RNA was brought to a volume of 6.2 µL with DEPC-treated H2O, and 0.8 µL 10× reaction buffer and 1 µL (=1 U) of DNase enzyme were added before incubation at 37° C. for 30 min. The reaction was terminated by addition of 1 µL Stop Buffer and incubation at 65° C. for 10 min. cDNA synthesis was performed with random hexamer primers (Invitrogen, Cat. no. 48190011) using SuperScript II Reverse Transcriptase (Invitrogen, Cat. no. 18064014) according to the manufacturer's protocol. The qRT-PCR volume was 18 µl, consisting of 4.5 ng reverse transcribed RNA in water, 200 nM forward and reverse primer (synthesized by Invitrogen) and Platinum SYBR Green qPCR SuperMix-UDG with ROX (Invitrogen, Cat. no. 11744500). The TATA box binding protein (TBP, NCBI Reference Sequence: NM_003194.4) gene was used as endogenous control for human samples, while the Ubiquitously expressed transcript (Uxt, NCBI Reference Sequence: NM_013840.3) gene was used as endogenous control for mouse samples. Primer sequences are listed in Table 4. Assays were run in MicroAmp Optical 96-Well Reaction Plates (Applied Biosystems, Cat. no. N801-0560) on an ABI Prism 7000 Sequence Detection System (Applied Biosystems) with 2 min at 50° C., 10 min at 95° C., and 40 cycles of 15 s at 95° C. and 1 min at 60° C. Data evaluation was performed using AnalyzerMiner Cq and efficiency calculation methods provided by the QPCR online application (Pabinger, Bioinformatics (2009), 10: 268).

miRNA qRT-PCR.

miRNA expression levels were analyzed using TaqMan microRNA Assays (Applied Biosystems) for menu-miR-26a (Cat. no. 000405) and small nucleolar RNA 202 (snoRNA202, Cat. no. 4380914), which served as endogenous control in combination with the TaqMan MicroRNA Reverse Transcription (RT) Kit. For each sample, two RT reactions were performed by combining 10 ng total RNA (in a volume of 5 µL ddH2O) with 3 µL 5×RT primer solution (hsa-miR-26a or snoRNA202) and 7 µL of an RT MasterMix (Applied Biosystems, Cat. no. 4366596) which consisted of 0.15 µL dNTP mix (100 mm), 1 µL (=50 U) MultiScribe™ Reverse Transcriptase, 1.5 µL 10×RT buffer, 0.19 µL (=3.8 U) RNase Inhibitor and 4.16 µL nuclease-free H2O. RT reactions were placed into the PTC-225 PCR cycler (MS Research) and incubated at 16° C. for 30 min, at 42° C. for 30 min and at 85° C. for 5 min. Subsequent qRT-PCR reactions were pipetted into MicroAmp Optical 96-well Reaction Plates (Applied Biosystems, Cat. no. N801-0560) and consisted of 9 µL 2× TaqMan Gene Expression Master Mix (Applied Biosystems, Cat. no. 4364341), 6.9 µL DEPC-treated $H_2O$, 0.9 µL 20× TaqMan Assay (hsa-miR-26a or snoRNA202) and 1.2 µL of the respective reverse transcribed sample. The setup of qRT-PCR runs was identical as for the conventional SYBR Green method described above. miRNA expression levels were also analyzed using the miRCURY LNA Universal RT microRNA PCR system (Exiqon) as described by the manufacturer. Therefore, 20 ng total RNA of each sample were brought to a volume of 14 µL with nuclease-free $H_2O$, and after addition of 4 µL 5× reaction buffer and 2 µL of Enzyme Mix (Exiqon, Cat. no. 203300), the reactions were incubated in the PTC-225 PCR cycler (MS Research) at 42° C. for 60 min, followed by heat inactivation at 95° C. for 5 min. These RT reactions were then diluted 1:80 with a solution containing 381 nM ROX reference dye (Roche, Cat. no. 04673549001) in nuclease-free $H_2O$. Primer pairs for detection of miR-26a (Exiqon, Cat. no. 204724) and 5S rRNA (Exiqon, Cat. no. 203906, serving as internal reference) were dissolved in 220 µL nuclease-free $H_2O$. Subsequently, qRT-PCR reactions were pipetted into MicroAmp Optical 96-well Reaction Plates (Applied Biosystems, Cat. no. N801-0560). These reactions consisted of 9 µL SYBR Green Master Mix, Universal RT (Exiqon, Cat. no. 203400), 1.8 µL PCR primer mix and 7.2 µL diluted cDNA sample (with ROX). The setup of qRT-PCR runs was identical as for the conventional SYBR Green method described above. Relative quantification of miRNA expression levels was quantified using the ddCq method.

Western Blot Analysis.

hMADS cells were harvested using a buffer consisting of 25 mM TRIS (Roth, Cat. no. Roth/5429.3)-HCl (Roth, Cat. no. K025.1) (pH 7.4), 100 mM NaCl Roth, Cat. no. 3957.2), 1 mM EDTA (Roth, Cat. no. R80431), 0.5% Triton X-100 (Roth, Cat. no 3051.2), 0.5% NP40 (Roche, Cat. no. 13269300), 0.5 mM Na-orthovanadate (Sigma, Cat. no. S6508), 10 mM NaF (Merck, Cat. no. 27860.231) and 10 mM β-glycerophosphate (Sigma, Cat. no. G9891). Cell lysates were homogenized on ice by a 10 sec ultrasound treatment (Sonopuls UW2070, Bandelin), followed by centrifugation for 10 min at 4° C. and 16000×g. Subsequently, cell lysates were aliquoted and stored at −80° C. until SDS-PAGE and Western blot analysis. Additionally, the protein concentration of each sample was determined (in duplicates) using the BCA Protein Assay Kit (Thermo Scientific, Cat. no. 23227). Therefore, a dilution series of 2 mg/mL BSA standard (in 0.9% NaCl) was prepared. 2 µL of each sample were combined with 10 µL of 0.9% NaCl, and 10 µL of BSA standard solutions were combined with 2 µL of lysis buffer in the wells of a 96-well multiwell plate. A BCA Protein Assay reagent was prepared by diluting Reagent B 1:50 with Reagent A, and reactions were initiated by addition of 200 µL BCA Protein Assay Reagent to each well containing sample or standard solution. Subsequently, the 96-well plate was incubated at 37° C. for 30 min before absorbance at 562 nm was recorded on a SPECTRAmax PLUS384 absorbance microplate reader (Molecular Devices). For polyacrylamide gel electrophoresis, 50 µg of protein sample or 10 µL of Plus2 Pre-Stained Standard (Invitrogen, Cat. no. LC5925) were prepared in 1× NuPAGE LDS Sample Buffer (Invitrogen, Cat. no. NP0007) and 0:5 M DTE to reach a final volume of 40 µL. After incubation at 70° C. for 10 min, samples were loaded on 10% Bis-Tris gels which were placed in 1×MOPS SDS Running Buffer (Invitrogen, Cat. no. NP0001) supplemented with 833 µL of antioxidant solution per 1000 mL of buffer. Subsequently, electrophoresis was run for 1 h at 175V using a Mini Trans-Blot Electrophoretic Transfer Cell (BioRad). For transfer of proteins, nitrocellulose membranes (Pall, Cat. no. 66485) were activated by incubation in $ddH_2O$ for 5 min, followed by assembly of a transfer sandwich that was placed in transfer buffer consisting of Tris-Glycine-SDS buffer (25 mM Tris (Roth, Cat. no. 54291), 192 mM glycine (Sigma, Cat. no. G7126), 0.1% SDS (Merck, Cat. no. APPCA2263), pH 8.3) and 20% methanol (Roth, Cat. no. 83885). Transfer was performed at 4° C., 120 V and 0.5 A for 90 min using the Mini Trans-Blot Electrophoretic Transfer Cell (BioRad). Efficiency of transfer was controlled by staining of membranes and the polyacrylamide gels with PonceauS (Fluka, Cat. no. 09276) and SimplyBlue SafeStain (Invitrogen, Cat. no. LC6060), respectively. After transfer, membranes were blocked in TBS-T buffer (10 mm Tris, 150 mm NaCl, 0:1% Tween-20 (Merck, Cat. no. 655204), pH 7.5) supplemented with 5% BSA (PAA, Cat. no. K45-001). Primary antibodies (UCP1: Merck, Cat. no. 662045; βTubulin: Sigma, Cat. no. T5201) were diluted in TBS-T buffer with 1% BSA (1:750 and 1:2000 for anti-UCP1 and anti-βTubulin antibody, respectively), and incubation of membranes with primary antibodies was carried out at 4° C. over night. Subsequently, membranes were washed thrice with TBS-T buffer, and incubated with secondary antibody solution (swine anti-mouse (DakoCytomation, Cat. no. P0399) for UCP1, goat anti-mouse (DakoCytomation, Cat. no. P0447) for βTubulin, 1:2000 dilution in TBS-T with 1% BSA) for 2 h at room temperature. Finally, membranes were again washed three times in TBS-T and SuperSignal enhanced chemiluminescence (ECL) substrate (Pierce, Cat. no. 34077) was applied to detect the chemiluminescent signal on an ECL film (GE Healthcare, Cat. no. 28-9068-36). Stripping of blots was performed by incubation of membranes at room temperature for 15 min, followed by re-blocking as described above.

Luciferase Reporter Assay.

The 3'UTRs of homo sapiens retinoblastoma 1 mRNA (RB1, NCBI Reference Sequence: NM_000321.2), nuclear receptor interacting protein 1 (NRIP1, NCBI Reference Sequence: NM_003489.3) and ribosomal protein S6 kinase (RPS6KB1, NCBI Reference Sequence: NM_003161.2) were amplified from human genomic DNA by PCR (primers synthesized by Invitrogen, primer names: RB1-Luc, NRIP1-Luc, and RPS6KB1-Luc; see Table 4). PCR was performed using High Fidelity PCR Enzyme Mix (Fermentas, Cat. no. K0192) according to the manufacturer's instructions. Each reaction consisted of 5 µL High Fidelity PCR Buffer (5×), 1 µL 10 mm dNTP mix, 2 µL of a mix containing 12.5 µM of the respective forward and reverse primer in DEPC-treated $H_2O$ and 200 ng of genomic DNA (isolated from hMADS cells). The PCR conditions for amplification of the RB1 3'UTR fragment were as follows: 5 min/94° C.; 10 cycles of 30 s/94° C.—30 s/58° C.—1 min 50 s/72° C. (where the temperature of the second step was reduced by 0.5° C. with every cycle); 20 cycles of 30 s/94° C.—30 s/53° C.—1 min 50 s/72° C.; 10 min/72° C. The PCR conditions for amplification of the NRIP1 3'UTR fragment were as follows: 5 min/94° C.; 35 cycles of 30 s/94° C.—30 s/55° C.—2 min 40 s/72° C.; 10 min/72° C. The PCR conditions for amplification of the RPS6KB1 3'UTR fragment were as follows: 5 min/94° C.; 10 cycles of 30 s/94° C.—30 s/52° C.—4 min/68° C.; 10 min/72° C.; 25 cycles of 30 s/94° C.—30 s/52° C.—4 min 10 s/68° C. (where the length of the second step was increased by 10 s with every cycle); 10 min/68° C. All PCRs were performed using the PTC-225 PCR cycler (MS Research). After PCR, reactions were mixed with 10 µL 6× loading dye (Fermentas, Cat. no. R0611) and agarose gel electrophoresis was performed on 1% agarose gels containing Ethidium bromide (Lactan, Cat. no. 2218.1) for DNA visualization. Electrophoresis was performed at 105 V with a run time of 60 min. Amplification of desired 3'UTR regions was checked under UV light by comparison of sample DNA bands with bands of a GeneRuler™ 1 kb DNA Ladder (Fermentas, Cat. no. SM0311), and DNA bands of interest were cut with a scalpel and transferred to 1.5 mL microcentrifuge tubes (Sarstedt, Cat. no. 72.690.001). PCR products were then isolated using the PureLink Quick Gel Extraction Kit (Invitrogen, Cat. no. K2100-12). Briefly, 300 µL per 100 mg of agarose gel were added and tubes were incubated at 50° C. for 15 min. Reactions were applied to a spin column (placed on a collection tube) and centrifuged at $1.3 \times 10^4$ g for 1 min. Flowthrough was discarded and 700 µL wash buffer were added to each column. Reactions were incubated at room temperature for 5 min, then centrifuged as above and the flowthrough was discarded. After another centrifugation step as above, columns were placed onto a clean 1.5 mL microcentrifuge tube, 20 µL ddH2O were added, reactions were incubated at room temperature for 1 min and then centrifuged at $1.3 \times 10^4$ g for 2 min. The flowthrough was once again pipetted onto the column and incubation and centrifugation were performed as before to yield the purified DNA fragments. Digestion of DNA fragments with XhoI and NotI restriction enzymes (Promega, Cat. nos. R6165 and R6435) was performed in reactions of 20 µL, consisting of 150-500 ng purified DNA, 2 µL 10× Buffer D (Promega, Cat. no. R9921), 0.2 µL acetylated BSA (Promega, Cat. no. R3961), 0.5 µL XhoI and 0.5 µL NotI restriction enzymes (=5 U), and ddH$_2$O. Reactions were incubated at 37° C. for 1 h and subsequently purified using the QIAquick PCR Purification Kit (QIAGEN, Cat. no. 28106). Briefly, samples were mixed with 100 µL Buffer PBI and pipetted onto a QIAquick spin column (placed in a collection tube) for centrifugation at $1.3 \times 10^4$ g for 1 min. The flowthrough was discarded, 750 µL Buffer PE were added to each sample and columns were centrifuged as before. After discarding of flowthrough and another centrifugation at $1.3 \times 10^4$ g for 1 min, each column was placed onto a clean 1.5 mL microcentrifuge tube, 20 µL ddH$_2$O were added and samples were incubated for 1 min before centrifugation as above. The flowthrough was once again pipetted onto the column and incubation and centrifugation were performed as before to yield the XhoI and NotI digested DNA fragments. Digestions of psiCHECK-2 vector (Promega, Cat. no. C8021) with XhoI and NotI restriction enzymes were performed similar to digestions of PCR-amplified 3'UTR DNA fragments with 1 µg of plasmid DNA as input. After digestion, the solutions were applied to a 1% agarose gel, electrophoresis was carried out as described above and bands containing the double-digested DNA backbone were cut under UV light. Subsequently, plasmid DNA was purified with the PureLink Quick Gel Extraction Kit as described above.

The purified amplicons obtained from the 3'UTRs of RB1, NRIP1, and RPS6KB1 (1836 bp, 2518 bp and 3605 bp, respectively) were inserted into the XhoI and NotI restriction sites of the psiCHECK-2 vector (Promega, Cat. no. C8021) by ligation using T4 Ligase (Invitrogen, Cat. no. 15224017). Therefore, the respective insert DNA was combined with backbone DNA at a molar ratio of 3:1 to yield 100 ng total DNA in a volume of 15 µL ddH$_2$O. After addition of 4 µL 5× reaction buffer and 1 µL (=1 U) T4 DNA Ligase, reactions were incubated at 26° C. for 1 h, and at 16° C. for 72 h. Subsequently, transformation of DH5α *E. coli* cells (Invitrogen, Cat. no. 18265-017) was carried out. Therefore, 10 µL of ligation reaction were mixed with 50 µL of DH5α solution (thawed on ice), mixed carefully and incubated on ice for 30 min. Subsequently, reactions were transferred to 42° C. for 20 s and back to ice. 2 min later, 300 µL S.O.C. Medium (Invitrogen, Cat. no. 15544034; prewarmed to 37° C.) were added and reactions were incubated at 37° C. with shaking at 225 rpm for 60 min. Finally, reactions were plated onto Luria-Bertani(LB)-Agar-plates (1% peptone (Roth, Cat. no. 8986.1), 1% NaCl (Roth, Cat. no. 3957.2), 0.5% yeast extract (Sigma, Cat. no. Y1625) and 1.5% agar (Sigma, Cat. no. A5054) in ddH$_2$O) containing 100 µg/mL Ampicillin (Sigma, Cat. no. A9518) and incubated at 37° C. for 14-18 h.

To analyze cloning of 3'UTR DNA fragments into the psiCHECK-2 vector, colony PCRs were performed using Taq polymerase (Fermentas, Cat. no. EP0402) and a primer pair homologous to 2 regions up- and downstream of the psiCHECK-2 multiple cloning site (primer name: psiCHECK-2_seq; see Table 4 for sequences). The reactions consisted of 2 µL 10× Taq Buffer, 1.2 µL 25 mM MgCl2, 0.4 µL 10 mm dNTP mix, 0.16 µL of a primer mix containing 12.5 µm forward and reverse sequencing primer, 0.2 µL (=1 U) Taq Polymerase and ddH$_2$O up to 20 µL. For inoculation, colonies on the LB-Agar-plates were touched with a sterile 200 µL pipette tip which was then dipped into the PCR reactions. Conditions for subsequent PCR were as follows: 94° C./2 min; 30 cycles of 94° C./30 s, 50° C./30 s and 72° C./1 min, followed by a final elongation step of 10 min at 72° C. PCR was performed using the PTC-225 PCR cycler (MS Research). Reactions were then applied to a 1% agarose gel and electrophoresis was performed as described above. Colonies corresponding to reactions that yielded the expected DNA fragment were used for inoculation of 5 mL LB Medium (prepared as LB Agar plates described above, except that no Agar was added) containing 100 µg/mL Ampicillin, which was subsequently incubated at 37° C. with shaking at 225 rpm for 14 h. Afterwards, plasmid purification was performed using the QIAprep Spin Miniprep Kit (QIAGEN, Cat. no. 21706) as described by the manufacturer. Briefly, suspensions were centrifuged at 4500 g and 4° C. for 10 min, the supernatant was decanted and the bacterial pellet was resuspended in 250 µL Buffer P1 and transferred into a 1.5 mL microcentrifuge tube. 250 µL Buffer P2 were added, the reactions were mixed by inverting the tube several times, and 350 µL Buffer N3 were added. Samples were mixed again and centrifuged at $1.6 \times 10^4$ g for 10 min. Subsequently, the supernatants were applied to QIAprep spin columns (placed onto collection tubes), centrifuged at $1.6 \times 10^4$ g for 1 min and the flowthrough was discarded. 500 µL Buffer PB were applied on each column, reactions were again centrifuged at $1.6 \times 10^4$ g for 1 min and flowthrough was again discarded. Next, 750 µL Buffer PE were pipetted on each column and reactions were centrifuged as in the last step, followed by discarding of the flowthrough. To dry the columns, reactions were once again centrifuged as before. Subsequently, columns were placed onto clean 1.5 mL microcentrifuge tubes, 40 µL ddH2O were added, reactions were incubated at room temperature for 1 min and then centrifuged at $1.4 \times 10^4$ g for 1 min. The flowthrough was once again pipetted onto the column and reactions were again incubated and centrifuged as in the last step to yield purified psiCHECK-2 vectors. Correct insertion of the desired 3'UTR fragments was validated by sequencing (performed by Agowa) using the "psiCHECK-2_seq" primer pair (see Table 4 for sequences).

For transfections, HEK293 cells were seeded in 96-well plates at a density of $2 \times 10^4$ cells per well. After 20 h, transfections were performed using 0.2 µL. DharmaFECT Duo (Dharmacon, Cat. no. T-2010), 100 ng vector, and either 50 nM of Negative Control #1 (NTC) or miR-26a microRNA mimic (Dharmacon) in a final volume of 100 µL (80 µL HEK medium+20 µL transfection mix according to the recommendations by Dharmacon) per well. Cells were assayed 48 h after transfection and assayed for *Renilla* and firefly luciferase activities using the Dual Luciferase Reporter Assay System (Promega, Cat. no. E1980) and the luminometer Orion II (Bertold). Therefore, medium was carefully removed from HEK293 cells, and cells were washed with 30 µL PBS per well. Lysis was performed by addition of 30 µL Passive Lysis Buffer (PLB, Promega, Cat. no. E1941, diluted 1:5 with ddH$_2$O from 5× stock) and incubation at room temperature with shaking (100 rpm) for 25 min. Subsequently, lysates were frozen at −20° C. and thawed for luciferase assays. Prior to measurements, the two-channel liquid system of the ORION II microplate luminometer was cleaned with 70% Ethanol and ddH$_2$O, followed by priming with LARII and Stop&Glo reagents (diluted 1:50 with Stop&Glo R Buffer), respectively. 6 µL of samples were pipetted into wells of a 96-well flat bottom assay plate (Costar, Cat. no. 3912, each sample assayed in duplicate), and the measurement was started. First, firefly luciferase (FL) activity was measured by addition of 25 µL LARII reagent per well, with 2 s pre-measurement delay and a subsequent photon flux integration time of 10 s. Next, 25 µL Stop&Glo reagent per well were added and *Renilla* luciferase (RL) activity was recorded with identical settings as before. For every well, RL activities were normalized to FL activities, followed by averaging of technical replicates and comparison between different samples. The statistical significance of differences in *Renilla* normalized to firefly luciferase activity was assessed using an unpaired t-test ($p<0.05$).

Isolation, Cultivation, and Transfection of Human Primary Adipose-Derived Stromal Cells.

Adipose tissue biopsies obtained from surgeries of varicose veins or inguinal herniae were used to isolate human primary adipose derived stromal cells (hPASCs) by a method adapted from Hauner, Methods Mol Biol (2001), 155:239-47. Biopsies were transported to the lab on ice in "Medium A", consisting of DMEM/Ham's F12 (50:50), 15 mm HEPES, 50 µg/mL Penicillin/Streptomycin and 100 µg/mL Normocin (see above for reagent suppliers and Cat. nos.). Tissues were repeatedly rinsed in PBS to decrease the number of attached red blood cells. Using sterile scissors and tweezers, adipose tissue was cut into small pieces. Pieces were then transferred to "Medium B" (3 mL per g tissue), consisting of 200 U/mL Collagenase Type I (Worthington, Cat. no. CLS 1) and 20 mg/mL fatty acid-free Bovine Serum Albumin (BSA, PAA, Cat. no. K31-002) in Medium A, and incubated for 45 min at 37° C. with mild agitation. Collagenase digested suspensions were diluted 1:5 with "Medium C", consisting of Medium A with 8% FBS, and filtered through a 250 µm mesh (VWR, Cat. no. 510-9526). The filtrate was centrifuged for 5 min at 600× g. Subsequently, the supernatant was filtered through a 100 µm (BD Falcon, Cat. no. 952360) and a 40 µm BD Falcon, Cat. no. 352340) mesh and centrifuged as above. The cell pellets obtained from both centrifugation steps were then resuspended in 10 mL Medium C, combined, filtered through a 100 µm mesh and again centrifuged as above. The cell pellet was resuspended in 1 mL red blood cell lysis buffer (Sigma, Cat. no. R7757) and incubated for 1 min before addition of 20 mL "Medium D", consisting of Medium A with 2 mM L-Glutamine and 10% FBS (see above for reagent suppliers and Cat. nos.). After centrifugation as above, the cell pellet was resuspended in Medium D, cell concentration was determined and cells were seeded at 2-3×10$^4$ cells/cm$^2$ in 24-well plates. Medium was removed after 16 h and hPASCs were washed thrice with PBS to remove residual contaminating red blood cells. Subsequently, hPASCs were grown to confluence in Medium D, followed by transfection as described above (transfection volumes were scaled by a factor of 0.5). Two days later, adipocyte differentiation was induced by changing the medium to DMEM/Ham's F12 (50:50), 2 mM L-Glutamine, 10 mM HEPES, 100 µg/mL Nonnocin, 860 µM (=5 µg/mL) Insulin, 10 µg/mL apo-Transferrin, 0.2 nM T3, 100 nM Rosiglitazone, 100 µM IBMX and 1 µM Dexamethasone (see above for reagent suppliers and Cat. nos.). IBMX was omitted from day 3 on, and medium was changed every two to three days. Experiments were analyzed at day 16 of adipocyte differentiation.

Oxygen Consumption Measurements.

hMADS-2 cells were transfected with 5 nM miR-26a mimic, or a non-targeting control mimic, and adipocyte differentiation was performed as described above. Rosiglitazone was added to the differentiation medium until day 16, when cellular respiration was assayed as described below. Oxygen consumption was recorded using a luminescent nanosensor-based detection system consisting of an oxygen microsensor and a transmitter device (connected to a computer). Calibration of sensors was carried out prior to measurements of cellular respiration using two aqueous solutions tempered to 37° C.: (i) ddH$_2$O saturated with O2 (corresponding to 100% O2 oxygen saturation, or 207 µM O$_2$), and (ii) a glucose solution to which glucose oxidase (Fluka, Cat. no. 49178) was added immediately before measurement (leading to deprivation of O$_2$ from the aqueous solution, corresponding to 0% oxygen saturation). Adipocytes from a 100 mm cell culture plate were used for a single measurement. Medium was transferred to a 15 mL tube and centrifuged for 7 min at 600×g. Meanwhile adipocytes were washed once with PBS and incubated with 700 trypsin (1×, Invitrogen, Cat. no. 15400054) for 5 min at 37° C. Subsequently, 600 µL of a "2× measurement medium" (2×DMEM/Ham's F12, 20% FBS, 20 mm HEPES, 4 mm L-Gln, 2× Normocin, see above for reagent suppliers and Cat. nos.) were added and the cell suspension was carefully mixed by pipetting. After centrifugation of medium, the supernatant was discarded and the pelleted cells were carefully resuspended in 100 µL 2× measurement medium before being added back to the cell suspension containing detached adipocytes. Subsequently, cell concentration and viability were determined to calculate the volume of cell suspension corresponding to 5×10$^5$ living cells, which was carefully pipetted into a 1.8 mL chromatography vial (Knauer, Cat. no. A0637) containing a magnetic stirrer bar. The remaining volume of the vial was filled with 1× measurement medium (a 1:2 dilution of 2× measurement medium with ddH$_2$O), and a screw cap with septum was used to close the measurement chamber. Finally, a needle containing the oxygen microsensor (PreSens, Cat. no. 200000045) was inserted through the septum into the cell suspension and the vial was placed in 37° C.-tempered H$_2$O above a magnetic stirrer set to 500 rpm. Measurement was performed on a Microx TX 3 Micro Fiber Optic Oxygen Transmitter (PreSens) by recording the phase shift Φ of the light pulse, which is dependent on O$_2$ concentration (see below), in intervals of 1 sec, with dynamic averaging of signals within an interval of 4 measurement points. Usually, a linear oxygen consumption could be observed after 5 min. After recording respiration of adipocytes in 1× measurement medium (without any additives), oligomycin (Sigma, Cat. no. O4876, 100 µg/mL stock solution in ethanol) was added through the septum with a Hamilton syringe (Hamilton, Cat. no. 80300) to reach a final concentration of 0.5 µg/mL. After several minutes, antimycin A (Sigma, Cat. no. A8674, 200 µg/mL stock solution in ethanol) was added with a Hamilton syringe to reach a final concentration of 1 µg/mL, and antimycin A-insensitive respiration was recorded before the measurement was terminated. Usually, adipocytes from three cell culture dishes were measured serially as technical replicates. For transformation of recorded phase shifts into O$_2$ concentration, luminescence decay time was calculated according to the equation $$\tau = \frac{\tan\phi}{2*\pi*f}$$

where $\Phi$ is the phase shift and f is the frequency of modulation (i.e., 4520 Hz for the used device). Subsequently, the $O_2$ concentration was calculated according to the Stern-Volmer equation $$[O_2] = \frac{\frac{\tau_0}{\tau} - 1}{K_{SV}}$$

where $\tau_0$ is the luminescence decay time in a solution without $O_2$, $\tau$ is the actual luminescence decay time in the solution, and KSV is the Stern-Volmer constant, which is calculated from luminescence decay times of the two calibration solutions and the known molar concentrations of $O_2$ in dd$H_2O$ at 100% and 0% oxygen saturation (i.e. 207 μm and 0 μm at 37° C.) according to the formula:

$$K_{SV} = \frac{\tau_{100} - \tau_0}{207 - 0}$$

Finally, $O_2$ consumption rates were calculated by fitting a linear regression function over time intervals of 30 sec to 2 min. Basal respiration was defined as antimycin A-sensitive respiration. Likewise, respiration rates after addition of oligomycin were corrected for antimycin A-insensitive oxygen consumption rates to quantify uncoupled respiration.

Example 2

Differential Expression of miR-26a Between Murine White and Brown Adipose Tissue Quantification of miR-26a was performed using the TaqMan microRNA Assay System as described in Example 1; miR-26a levels were normalized to small nucleolar RNA 202 (snRNA202) as internal reference. Expression profiling for miR-26a in mouse tissues revealed miR-26a as differentially expressed between white (WAT) and brown adipose tissue (BAT). miR-26a expression increased by 80% from white to brown adipose tissue (FIG. 1). In contrast, miRNA profiling using microarrays revealed no differential expression for miR-26a, miR-26b, miR-1297, which is in line with no observed differential expression in hMADS cells differentiated to brown adipocytes by continuous rosiglitazone treatment, as shown in Table 1. Moreover, also miR-106a, miR-17, miR-20a, as well as hsa-miR-452 and mmu-miR-452 did not demonstrate any differential expression between WAT and BAT.

Despite these results, data provided herein document that polynucleotides (e.g., miRNAs) as described herein allow adipocyte differentiation to the brown phenotype.

Example 3 miR-26a Mediated Switch from White to Brown Adipocyte Differentiation

Therefore, undifferentiated WADS cells of two donors (hMADS-2 and hMADS-3) were transiently transfected with 5 nM miR-26a mimics or non-targeting control before adipogenic differentiation and treated the cells with rosiglitazone for 9 or 16 days as described in Example 1. As control and reference, rosiglitazone treatment for only the first 9 days of differentiation led to white hMADS adipocytes whereas continuous rosiglitazone treatment until day 16 (final harvesting) led to the conversion from white to brown hMADS adipocytes, as previously published (Elabd, Stem cells (2009), 27: 2753-2760).

miR-26a overexpression in undifferentiated hMADS-3 cells followed by adipogenic stimulation to white adipocytes yielded strongly increased UCP1 expression at mRNA and protein level at day 9 and 16 of differentiation (FIGS. 2A and 2B, determined by qRT-PCR and Western blot as described in Example 1). Whereas rosiglitazone treatment until day 9 of differentiation did not induce UCP1 expression at day 9 and 16 of differentiation (light grey bar in the left and mid panel), miR-26a overexpression yielded strongly increased UCP1 expression (dark grey bar in the left and mid panel). Rosiglitazone treatment until day 16 significantly induced UCP1 mRNA and protein expression (light grey bar in right panel) while additional miR-26a overexpression (dark grey bar in right panel) increased UCP1 expression by ~60% on top of rosiglitazone treatment. hMADS-2 cells treated in the same manner yielded similar and comparable results. These results indicate a switch from white to brown adipocyte differentiation of human mesenchymal stem cells.

Given that miR-26a overexpression leads to increased UCP1 expression, it was evaluated whether this regulation also works in the opposite direction meaning decreased UCP1 expression upon miR-26a inhibition. Therefore, antisense oligonucleotides (ASOs) against miR-26a were transfected before adipocyte differentiation as described in Example 1, and UCP1 mRNA levels were measured at day 9 and 11 of differentiation. hMADS-3 cells showed repressed UCP1 mRNA levels upon miR-26a silencing (FIG. 3). These results indicate that miR-26a inhibition can also repress UCP1 expression, thereby suggesting consistently in both directions that UCP1 is under the control of miR-26a.

Example 4 miR-26a Mediated Conversion from White to Brown Adipocytes

Furthermore, it was tested whether miR-26a is also able to induce a conversion from white to brown adipocytes. Therefore, hMADS-3 cells were first differentiated to white adipocytes, transfected with miR-26a mimics or non-targeting control (NTC) at day 12 using two different transfection reagents (i.e. HiPerFect and Interferin), harvested at day 17 and analyzed for UCP1 expression levels by qRT-PCR. All procedures were performed as described in Example 1. As was revealed, miR-26a overexpression was able to double UCP1 expression on mRNA level indicating that miR-26a promotes the conversion of white adipocytes to the brown phenotype (FIG. 4).

Example 5

Putative Mechanism of miR-26a Mediated UCP1 Induction

'Retinoblastoma 1' (RB1, NCBI Reference Sequence: NM_000321.2), a repressor of mitochondrial biogenesis and UCP1 expression in white adipocytes (Tiraby, J Biol Chem (2003), 278: 33370-33376; Puigserver, Cell (1998), 92: 829-839; Wu, Cell (1999), 98: 115-124), 'nuclear receptor interacting protein 1' (NRIP1, NCBI Reference Sequence: NM_003489.3), another key player in the regulation of energy homeostasis also known as repressor of UCP1 expression (Powelka, J Clin Invest (2006), 116: 125-136; Parker, Biochem Soc Trans (2006), 34: 1103-1106; Kiskinis, EMBO J (2007), 26: 4831-4840; Christian, Mol Cell Biol (2005), 25: 9383-9391), and 'ribosomal protein S6 kinase' (RPS6KB1, NCBI Reference Sequence: NM_003161.2), a mediator of obesity and insulin resistance, which, if knocked out, leads to UCP1 expression in mouse WAT (Um, Nature (2004), 431: 200-205; Zhang, J Biol Chem (2008), 283: 35375-35382; Um, Cell Metab (2006), 3: 393-402; Adochio, Endocrinol (2009), 150: 1165-1173), have been found to be responsive to miR-26a modulation in hMADS cells (data not shown). Due to the fact that the function of a miRNA is mediated and thereby tightly bound to its direct target mRNAs, it was tested whether this is a direct or indirect miR-26a effect. Therefore, a predicted miR-26a target site was found in the 3'UTR of RB1, NRIP1, and RPS6KB1 (FIGS. 5A, 6A, 7A). At least those for RB1 and NRIP1 are highly conserved among mammals (FIGS. 5B, 6B). To examine whether miR-26a directly interacts with the predicted miR-26a response element in the 3'UTR of RB1, NRIP1, and RPS6KB1 respectively, luciferase reporter gene assays were performed as described in Example 1. Therefore, a fragment of the 3'UTR of each candidate was cloned into the psiCHECK-2 vector downstream the *Renilla* luciferase coding sequence and cotransfected either with 50 nM miR-NTC or miR-26a mimic into HEK293 cells as described in Example 1. Indeed, *Renilla* luciferase activity significantly decreased by 35% for the RB1 (FIG. 5C), 20% for the NRIP1 (FIG. 6C), and 19% for the RPS6KB1 (FIG. 7B) assay compared with non-targeting control transfected cells.

These results demonstrate that miR-26a indeed directly binds to the 3'UTR of RB1, NRIP1, and RPS6KB1 and inhibits these genes which in turn allows (i) expression of UCP1, a key marker and target to increase energy expenditure as well as allows (ii) elevated insulin sensitivity, thus combat obesity and the metabolic syndrome (Feldmann, Cell Metab (2009), 9: 203-209; Soliman, Curr Opin Lipidol (2005), 16: 317-323).

Moreover, miR-26a, miR-26b and miR-1297 share the same miRNA seed sequence (nucleotide position 2-8) (FIG. 8) and a high overall sequence homology. Therefore, these miRNAs are also all predicted to bind to the miR-26a binding sites in the 3'UTR of RB1, NRIP1, and RPS6KB1 suggesting that they are able to induce UCP1 expression.

Example 6

Differentially Expressed miRNAs Between White and Brown hMADS Adipocytes

Based on data describing the conversion of white to brown hMADS adipocytes by continuous treatment with rosiglitazone (Elabd, Stem Cells (2009), 27: 2753-2760), the miRNA signature between white and brown human hMADS-derived adipocytes was analyzed using miRNA microarrays (Table 1) as described in Example 1.

The identification of differentially expressed microRNAs was based on a cut-off for differential expression of 1.3 fold ($\log_2$ ratio>|0.378|) as previously described to be able to reliably identify differentially expressed transcripts (Wurmbach, Methods (2003), 31: 306-316). In addition, miR-455-5p served as positive control because it has already been described in mouse to be expressed at higher levels in brown compared to white adipocytes (Walden, J Cell Physiol (2009), 218: 444-449). In total, we identified 23 human miRNAs, 5 murine miRNAs, and 4 miRPlus which are not included in miRBase. The identified human miR-452 has a sequence overlap for the last 19 nucleotides with the murine miR-452, and the murine miR-322 has been identified so far only in mouse without excluding its existence in human (Table 2).

Example 7

Cold Exposure Elevated miR-26a Levels In Vivo in Murine WAT

Cold exposure is known to be the natural and environmental inducer of UCP1, hence of the brown adipocyte phenotype and of the thermogenic program. Therefore, to investigate whether miR-26a levels are regulated via cold exposure, miR-26a levels were quantified in WAT of cold (5° C.) exposed mice compared to mice housed at 23° C. using the miRCURY LNA Universal RT microRNA PCR system (Exiqon) as described in Example 1. Indeed, it was found herein that miR-26a levels were approximately 3-fold higher in WAT upon cold exposure. To ensure that mice reacted to cold stress as expected, UCP1 mRNA levels were monitored as positive control by qRT-PCR as described in Example 1. Indeed, UCP1 mRNA levels were elevated approximately 4-fold upon cold exposure compared to mice at ambient temperature, confirming the physiological response of murine WAT to cold stress (FIG. 9). Thus, since cold exposure, a known inducer of UCP1 expression, also elevated the level of polynucleotides described herein such as miR-26a levels in WAT in vivo, these results indicate that UCP1 induction in WAT via cold exposure is mediated by increased levels of agents such as polynucleotides described herein, e.g., miR-26a.

Example 8

Cold Exposure Evoked Diminished Expression Levels of Three Direct miR-26a Target Genes in Murine WAT To verify that cold exposure not only affects expression of miR-26a, but also represses (via miR-26a) its identified and validated direct targets RB1, NRIP1, and RPS6KB1, all three known to be repressors of UCP1 as described herein, RB1, NRIP1, and RPS6KB1 mRNA levels were quantified in murine WAT of cold (5° C.) exposed mice compared to WAT of mice housed at 23° C. by qRT-PCR as described in Example 1. Indeed, the mRNA levels of all three targets were significantly repressed (20-30%) upon cold exposure (FIG. 10). This correlates with the upregulation of miR-26a in WAT upon cold stress (FIG. 9) and indicates that cold exposure induces UCP1 expression via upregulation of agents described herein (e.g., polynucleotides comprising SEQ ID NO: 6 such as miR-26a, miR-26b or miR-1297), which in turn inhibit the UCP1-suppressors RB1, NRIP1, and RPS6KB1.

Example 9

$\beta_3$-Adrenergic Stimulation Elevated In Vivo miR-26a Levels in Murine WAT

When increasing the rate of food combustion (decreased metabolic efficiency) or the rate of heat production (e.g., upon cold exposure), a signal is transmitted via the sympathetic nervous system to the individual adipocytes (Cannon and Nedergaard, Physiol Rev (2004), 84: 277-359). The released transmitter is norepinephrine (NE) which primarily signals through $\beta_3$-adrenergic receptors which are primarily found in white (WAT) and brown adipose tissue (BAT). To investigate whether miR-26a induction is also mediated by $\beta_3$-adrenergic signalling, mice were subjected to short-term (3 h) and long-term (10 days) treatment with CL316243 (Tocris Bioscience, intraperitoneal injection of 1 mg/kg), the most selective $\beta_3$-agonist available (Himms-Hagen, Biochem Biophys Res Commun (1994), 266: R1371-R1382). Subsequently, mice were sacrificed to isolate perigonadal WAT depots for RNA isolation, followed by qRT-PCR for analysis of mmu-miR-26a (using the miRCURY LNA Universal RT microRNA PCR system (Exiqon)) and Ptgs2 and Ucp1 mRNA levels as described in Example 1. Indeed, miR-26a levels immediately doubled in murine WAT upon $\beta_3$-adrenergic stimulation (assayed 3 h after a single intraperitoneal injection), comparable to the already described immediate induction of Ptgs2 (COX-2, Vegiopoulos, Science (2010), 328:1158-61) (FIG. 11A). A similar elevation of miR-26a levels was evident after repeated $\beta_3$-adrenergic stimulation for 10 days (daily intraperitoneal injection), comparable to changes in Ucp1 mRNA levels (FIG. 11B). This is in line with the previously described induction of miR-26a by cold exposure (FIG. 9). Especially the $\beta_3$-adrenergic agonist CL316243 is known to stimulate UCP1-mediated thermogenesis, and as the present results demonstrate elevated miR-26a levels upon treatment with this $\beta_3$-agonist in vivo, it can be concluded that agents such as polynucleotides described herein (e.g., miR-26a) are involved in the induction of UCP1-mediated thermogenesis.

Example 10 miR-26a Inhibition Diminished UCP1 Induction on mRNA Level and Abolished UCP1 Induction on Protein Level As miR-26a overexpression induced UCP1 mRNA and protein levels in hMADS adipocytes (FIG. 2), it was investigated whether this regulation also works in the opposite direction. Moreover, as UCP1 induction during brown adipocyte differentiation was stimulated by permanent rosiglitazone treatment as shown herein, miR-26a inhibition may answer the question whether rosiglitazone mediated UCP1 induction is dependent on miR-26a. Thus, we transfected hMADS-2 cells at confluence with 25 nM anti-miR-26a antisense oligonucleotide, or with a non-targeting control antisense oligonucleotide, as described in Example 1. Subsequently, adipocyte differentiation was induced as described in Example 1. Cells were analyzed at day 16 of adipogenesis by qRT-PCR and Western blots for UCP1 mRNA and protein levels as described in Example 1. Upon rosiglitazone stimulated brown adipocyte differentiation ((B)AD), hMADS-2 cells had detectable UCP1 mRNA and protein levels if treated with the control oligonucleotide ASO-NTC (left panel in FIGS. 12A and 12B, respectively). Upon miR-26a inhibition with the LNA-based miR-26a antisense oligonucleotide (ASO-26a), UCP1 mRNA levels significantly decreased and UCP1 protein levels were even abolished (right panel in FIGS. 12A and 12B, respectively). These results are in line with the finding presented herein that agents such as polynucleotides described herein (e.g., miR-26a) induced UCP1 when overexpressed and indicates that the rosiglitazone mediated brown phenotype in hMADS adipocytes is dependent on polynucleotides described herein such as miR-26a. As rosiglitazone is a thiazolidinedione (TZD), a class of anti-diabetic drugs which work as insulin sensitizers, treatment with polynucleotides (e.g., miRNAs such as miR-26a) are of therapeutic use for the medical interventions as described and provided herein.

Example 11 miR-26a Mediated Induction of UCP1 in hPASCs of Adult Donors

Body mass index (BMI), percentage of body fat, and age have an inverse correlation with the existence of brown adipose tissue (van Marken Lichtenbelt, NEJM (2009), 360(15): 1500-8; Cypess, NEJM (2009), 360(15):1509-17). Hence, there is a need for the induction of UCP1, non-shivering thermogenesis, increased uncoupled respiration, and finally increased energy dissipation in human adults. As Example 3 and FIG. 2 provided herein demonstrated that miR-26a induced UCP1 in hMADS cells which have been isolated from white adipose tissue of infants, it was investigated whether miR-26a-mediated UCP1 induction also keeps promise in adults, particularly in middle-aged people. Therefore, human primary adipose derived stromal cells (hPASCs) were isolated from four distinct donors (age between 31 and 47 years) from the stromal vascular fraction (SVF) of human subcutaneous white adipose tissue (WAT), transfected with miR-26a, and differentiated to adipocytes as described in Example 1. Indeed, the ability of miR-26a to induce UCP1 during adipocyte differentiation of hMADS cells of infants could be congruently reproduced in hPASCs of four independent middle-aged adult donors (FIG. 13). Thus, the "fat browning" by polynucleotides described herein such as miR-26a appears as a general mechanism in both, young and adult, as well as middle-aged individuals. In sum, these results allow treatment of diseases and disorders of the energy homeostasis such as obesity, overweight, adiposity, metabolic syndrome, or diseases or disorders related to energy homeostasis disorders such as diabetes (e.g., diabetes type II), hypercholesterolemia or hypertension by using an agent (e.g., a polynucleotide, such as miR-26a, miR-26b or miR-1297) as described herein.

Example 12 miR-26a Elevated Energy Expenditure of hMADS Adipocytes

As miR-26a was shown herein to be able to increase UCP1 expression in adipose derived stromal vascular cell populations independent of donor age (FIG. 2, FIG. 13), it was investigated whether increased UCP1 expression ultimately results in augmented energy expenditure. While the measure of basal oxygen consumption reflects the cellular energy consumption, the measure of uncoupled respiration defines the part of energy expenditure by UCP1-dependent thermogenesis in brown adipocytes. Therefore, basal and uncoupled respiration of hMADS adipocytes was measured upon miR-26a overexpression as described in Example 1. Indeed, miR-26a was able to augment energy expenditure, reflected by an increased respiratory rate, of hMADS cells subjected to brown adipocyte differentiation by approximately 40% (FIG. 14A). This effect was due to increased UCP1 expression, as miR-26a transfection also increased uncoupled respiration (FIG. 14B). Thus, these results highlight agents such as polynucleotides as described herein (e.g., miR-26a) as agents that are able to switch adipocyte differentiation from energy storing white to energy dissipating thermogenic adipocytes.

Given the striking capacity of brown adipocytes to dissipate stored chemical energy, these results allow treatment of diseases and disorders of the energy homeostasis such as obesity, overweight, adiposity, metabolic syndrome, or diseases or disorders related to energy homeostasis disorders such as diabetes (e.g., diabetes type II), hypercholesterolemia or hypertension by using agents such as polynucleotides (e.g., miR-26a) as described herein.

TABLE 4

Primer sequences
Sequences of self-designed primers for qRT-PCR, or for establishment of luciferase reporter vectors, are listed below.

| Primer name | gene | forward primer (5'→3') | reverse primer (5'→3') |
|---|---|---|---|
| hUCP1 | UCP1 (NM_021833.4) | GTGTGCCCAACTGTGCAATG (SEQ ID NO: 35) | CCAGGATCCAAGTCGCAAGA (SEQ ID NO: 36) |
| hTBP | TBP (NM_003194.4) | ACGCCAGCTTCGGAGAGTTC (SEQ ID NO: 37) | CAAACCGCTTGGGATTATATTCG (SEQ ID NO: 38) |
| mUcp1 | UCP1 (NM_009463.3) | TGAACCCGACAACTTCCGAA (SEQ ID NO: 39) | GGCCTTCACCTTGGATCTGAA (SEQ ID NO: 40) |
| mUxt | Uxt (NM_013840.3) | CTCACAGAGCTCAGCGACAGC (SEQ ID NO: 41) | AAATTCTGCAGGCCTTGTAGTTCTC (SEQ ID NO: 42) |
| mRb1 | RB1 (NM_009029.2) | TGAGAGACCGACATTTGGACCAGA (SEQ ID NO: 43) | AACACGTTTAAAGGTCTCCTGGGC (SEQ ID NO: 44) |
| mNrip1 | NRIP1 (NM_173440.2) | TCAGGCTGAGGCAGACGATAC (SEQ ID NO: 45) | CCTCGCAACTTCCTTAGCACA (SEQ ID NO: 46) |
| mRps6kb1 | RPS6KB1 (NM_028259.4) | TGGACCATGGGGGAGTTGGACC (SEQ ID NO: 47) | AGCCCCCTTTACCAAGTACCCGA (SEQ ID NO: 48) |
| mPtgs2 | Ptgs2 (NM_011198.3) | CGCAAACGCTTCTCCCTGAAGCC (SEQ ID NO: 49) | TTTTCCACCAGCAGGGCAGGGT (SEQ ID NO: 50) |
| RB1-Luc | RB1 (NM_000321.2) | CATCAGCTCGAGATCTCAGGACCTTGGTGG (SEQ ID NO: 51) | CGGATCGCGGCCGCAGAACACAACATCAGACCATT (SEQ ID NO: 52) |
| NRIP1-Luc | NRIP1 (NM_003489.3) | CATCAGCTCGAGCTGGGAAGCGTGCTAACGATAAAGA (SEQ ID NO: 53) | CGGATCGCGGCCGCACAAAGTGAATCTGTGGATGTATGCCC (SEQ ID NO: 54) |
| RPS6KB1-Luc | RPS6KB1 (NM_003161.2) | CATCAGCTCGAGCAGAGCAATGCTTTTAATGA (SEQ ID NO: 55) | CGGATCGCGGCCGCTTTACATTCATTCAATCCGAA (SEQ ID NO: 56) |
| psiCHECK-2_seq | — | TAAGAAGTTCCCTAACACCG (SEQ ID NO: 57) | CGAGGTCCGAAGACTCATTTAG (SEQ ID NO: 58) |

The invention claimed is:

1. A method of treating diseases or disorders of the energy homeostasis, selected from the group consisting of obesity, overweight, hyperglycemia, adiposity and metabolic syndrome, in a patient comprising administering to the patient an effective amount of a composition comprising a polynucleotide selected from the group consisting of:
   (i) a polynucleotide comprising the nucleotide sequence of SEQ ID NO: 1;
   (ii) a polynucleotide comprising the nucleotide sequence of SEQ ID NO: 2;
   (iii) a polynucleotide comprising the nucleotide sequence of SEQ ID NO: 3;
   (iv) a polynucleotide which is at least 90% identical to any one of (i) to (iii); and
   (v) a polynucleotide according to (iv), which comprises the nucleotide sequence of SEQ ID NO: 6.

2. The method of claim 1, wherein said polynucleotide is about 15 to about 100 nucleotides in length.

3. The method of claim 1, wherein the composition contains about 1 ng/kg body weight to about 100 mg/kg body weight of said polynucleotide.

4. The method of claim 1, wherein said polynucleotide or a nucleotide sequence encoding said polynucleotide is positioned in a vector.

5. The method according to claim 4, wherein said vector is transduced, transformed or transfected into a cell of the patient.

6. The method of claim 1, wherein the composition is administered parenterally, via injection, orally, rectally, via inhalation, topically or vaginally.

7. The method according to claim 1, wherein said composition comprises two or more of said agents.

8. The method according to claim 1, wherein said subject is a human subject.

9. The method according to claim 1, wherein said composition comprises a polynucleotide comprising the nucleotide sequence of SEQ ID NO: 1.

10. The method according to claim 1, wherein said composition comprises a polynucleotide comprising the nucleotide sequence of SEQ ID NO: 2.

11. The method according to claim 1, wherein said composition comprises a polynucleotide comprising the nucleotide sequence of SEQ ID NO: 3.

12. The method according to claim 1, wherein said composition comprises a polynucleotide comprising the nucleotide sequence which is at least 90% identical to any one of (i) to (iii).

13. The method according to claim 1, wherein said composition comprises a polynucleotide which is at least 90% identical to any one of (i) to (iii), and which polynucleotide comprises the nucleotide sequence of SEQ ID NO: 6.

* * * * *

SEQUENCE LISTING

<160> NUMBER OF SEQ ID NOS: 78

<210> SEQ ID NO 1
<211> LENGTH: 22
<212> TYPE: RNA
<213> ORGANISM: Homo sapiens

<400> SEQUENCE: 1
uucaaguaau ccaggauagg cu                                              22

<210> SEQ ID NO 2
<211> LENGTH: 21
<212> TYPE: RNA
<213> ORGANISM: Homo sapiens

<400> SEQUENCE: 2
uucaaguaau ucaggauagg u                                               21

<210> SEQ ID NO 3

```
<211> LENGTH: 17
<212> TYPE: RNA
<213> ORGANISM: Homo sapiens

<400> SEQUENCE: 3
uucaaguaau ucaggug                                                     17

<210> SEQ ID NO 4
<211> LENGTH: 22
<212> TYPE: RNA
<213> ORGANISM: Homo sapiens

<400> SEQUENCE: 4
cucaguagcc aguguagauc cu                                               22

<210> SEQ ID NO 5
<211> LENGTH: 23
<212> TYPE: RNA
<213> ORGANISM: Homo sapiens

<400> SEQUENCE: 5
ucaagagcaa uaacgaaaaa ugu                                              23

<210> SEQ ID NO 6
<211> LENGTH: 6
<212> TYPE: RNA
<213> ORGANISM: artificial sequence
<220> FEATURE:
<223> OTHER INFORMATION: Synthetic oligonucleotide (seed sequence SEQ
      ID NOs: 1-3)

<400> SEQUENCE: 6 ucaagu                                                                  6

<210> SEQ ID NO 7
<211> LENGTH: 22
<212> TYPE: RNA
<213> ORGANISM: Homo sapiens

<400> SEQUENCE: 7
aacuguuugc agaggaaacu ga                                               22

<210> SEQ ID NO 8
<211> LENGTH: 22
<212> TYPE: RNA
<213> ORGANISM: Mus musculus

<400> SEQUENCE: 8
uguuugcaga ggaaacugag ac                                               22

<210> SEQ ID NO 9
<211> LENGTH: 23
<212> TYPE: RNA
<213> ORGANISM: Homo sapiens

<400> SEQUENCE: 9
aaaagugcuu acagugcagg uag                                              23

<210> SEQ ID NO 10
<211> LENGTH: 23
<212> TYPE: RNA
<213> ORGANISM: Homo sapiens

<400> SEQUENCE: 10
```
caaagugcuu acagugcagg uag                                          23

<210> SEQ ID NO 11
<211> LENGTH: 23
<212> TYPE: RNA
<213> ORGANISM: Homo sapiens

<400> SEQUENCE: 11
uaaagugcuu auagugcagg uag                                          23

<210> SEQ ID NO 12
<211> LENGTH: 23
<212> TYPE: RNA
<213> ORGANISM: Homo sapiens

<400> SEQUENCE: 12
uaaggugcau cuagugcaga uag                                          23

<210> SEQ ID NO 13
<211> LENGTH: 23
<212> TYPE: RNA
<213> ORGANISM: Homo sapiens

<400> SEQUENCE: 13
uaaggugcau cuagugcagu uag                                          23

<210> SEQ ID NO 14
<211> LENGTH: 22
<212> TYPE: RNA
<213> ORGANISM: Homo sapiens

<400> SEQUENCE: 14
cagugguuuu acccuauggu ag                                           22

<210> SEQ ID NO 15
<211> LENGTH: 23
<212> TYPE: RNA
<213> ORGANISM: Homo sapiens

<400> SEQUENCE: 15
cagugcaaua guauugucaa agc                                          23

<210> SEQ ID NO 16
<211> LENGTH: 22
<212> TYPE: RNA
<213> ORGANISM: Homo sapiens

<400> SEQUENCE: 16
uauugcacau uacuaaguug ca                                           22

<210> SEQ ID NO 17
<211> LENGTH: 22
<212> TYPE: RNA
<213> ORGANISM: Homo sapiens

<400> SEQUENCE: 17
cagcagcaau ucauguuuug aa                                           22

<210> SEQ ID NO 18
<211> LENGTH: 22
<212> TYPE: RNA
<213> ORGANISM: Mus musculus

<400> SEQUENCE: 18

-continued

| | |
|---|---|
| cagcagcaau ucauguuuug ga | 22 |

<210> SEQ ID NO 19
<211> LENGTH: 22
<212> TYPE: RNA
<213> ORGANISM: Homo sapiens

<400> SEQUENCE: 19

| | |
|---|---|
| acggguuagg cucuugggag cu | 22 |

<210> SEQ ID NO 20
<211> LENGTH: 21
<212> TYPE: RNA
<213> ORGANISM: Homo sapiens

<400> SEQUENCE: 20

| | |
|---|---|
| ugagaugaag cacuguagcu c | 21 |

<210> SEQ ID NO 21
<211> LENGTH: 22
<212> TYPE: RNA
<213> ORGANISM: Homo sapiens

<400> SEQUENCE: 21

| | |
|---|---|
| ggauuccugg aaauacuguu cu | 22 |

<210> SEQ ID NO 22
<211> LENGTH: 22
<212> TYPE: RNA
<213> ORGANISM: Homo sapiens

<400> SEQUENCE: 22

| | |
|---|---|
| ugagaacuga auuccauagg cu | 22 |

<210> SEQ ID NO 23
<211> LENGTH: 22
<212> TYPE: RNA
<213> ORGANISM: Homo sapiens

<400> SEQUENCE: 23

| | |
|---|---|
| aggggcuggc uuuccucugg uc | 22 |

<210> SEQ ID NO 24
<211> LENGTH: 22
<212> TYPE: RNA
<213> ORGANISM: Homo sapiens

<400> SEQUENCE: 24

| | |
|---|---|
| caaagaauuc uccuuuuggg cu | 22 |

<210> SEQ ID NO 25
<211> LENGTH: 21
<212> TYPE: RNA
<213> ORGANISM: Homo sapiens

<400> SEQUENCE: 25

| | |
|---|---|
| agcuacaucu ggcuacuggg u | 21 |

<210> SEQ ID NO 26
<211> LENGTH: 21
<212> TYPE: RNA
<213> ORGANISM: Homo sapiens -continued

```
<400> SEQUENCE: 26
gcaguccaug ggcauauaca c                                              21

<210> SEQ ID NO 27
<211> LENGTH: 22
<212> TYPE: RNA
<213> ORGANISM: Homo sapiens

<400> SEQUENCE: 27
uaugugccuu uggacuacau cg                                             22

<210> SEQ ID NO 28
<211> LENGTH: 22
<212> TYPE: RNA
<213> ORGANISM: Homo sapiens

<400> SEQUENCE: 28
ugaguauuac auggccaauc uc                                             22

<210> SEQ ID NO 29
<211> LENGTH: 22
<212> TYPE: RNA
<213> ORGANISM: Homo sapiens

<400> SEQUENCE: 29
ugcggggcua gggcuaacag ca                                             22

<210> SEQ ID NO 30
<211> LENGTH: 21
<212> TYPE: RNA
<213> ORGANISM: Mus musculus

<400> SEQUENCE: 30
aacauccugg uccuguggag a                                              21

<210> SEQ ID NO 31
<211> LENGTH: 23
<212> TYPE: RNA
<213> ORGANISM: Mus musculus

<400> SEQUENCE: 31
aaggagcuua caaucuagcu ggg                                            23

<210> SEQ ID NO 32
<211> LENGTH: 21
<212> TYPE: RNA
<213> ORGANISM: Mus musculus

<400> SEQUENCE: 32
cuccgugcac acccccgcgu g                                              21

<210> SEQ ID NO 33
<211> LENGTH: 6
<212> TYPE: RNA
<213> ORGANISM: artificial sequence
<220> FEATURE:
<223> OTHER INFORMATION: Synthetic oligonucleotide (seed sequence SEQ
      ID NOs: 9-11)

<400> SEQUENCE: 33 aaagug                                                                6

<210> SEQ ID NO 34
```

```
<211> LENGTH: 19
<212> TYPE: RNA
<213> ORGANISM: artificial sequence
<220> FEATURE:
<223> OTHER INFORMATION: Synthetic oligonucleotide (consensus sequence
      SEQ ID NOs: 7 and 8)

<400> SEQUENCE: 34
uguuugcaga ggaaacuga                                                  19

<210> SEQ ID NO 35
<211> LENGTH: 20
<212> TYPE: DNA
<213> ORGANISM: artificial sequence
<220> FEATURE:
<223> OTHER INFORMATION: Synthetic primer

<400> SEQUENCE: 35
gtgtgcccaa ctgtgcaatg                                                 20

<210> SEQ ID NO 36
<211> LENGTH: 20
<212> TYPE: DNA
<213> ORGANISM: artificial sequence
<220> FEATURE:
<223> OTHER INFORMATION: Synthetic primer

<400> SEQUENCE: 36
ccaggatcca agtcgcaaga                                                 20

<210> SEQ ID NO 37
<211> LENGTH: 20
<212> TYPE: DNA
<213> ORGANISM: artificial sequence
<220> FEATURE:
<223> OTHER INFORMATION: Synthetic primer

<400> SEQUENCE: 37
acgccagctt cggagagttc                                                 20

<210> SEQ ID NO 38
<211> LENGTH: 23
<212> TYPE: DNA
<213> ORGANISM: artificial sequence
<220> FEATURE:
<223> OTHER INFORMATION: Synthetic primer

<400> SEQUENCE: 38
caaaccgctt gggattatat tcg                                             23

<210> SEQ ID NO 39
<211> LENGTH: 20
<212> TYPE: DNA
<213> ORGANISM: artificial sequence
<220> FEATURE:
<223> OTHER INFORMATION: Synthetic primer

<400> SEQUENCE: 39
tgaacccgac aacttccgaa                                                 20

<210> SEQ ID NO 40
<211> LENGTH: 21
<212> TYPE: DNA
<213> ORGANISM: artificial sequence
<220> FEATURE:
<223> OTHER INFORMATION: Synthetic primer
```

```
<400> SEQUENCE: 40
ggccttcacc ttggatctga a                                              21

<210> SEQ ID NO 41
<211> LENGTH: 21
<212> TYPE: DNA
<213> ORGANISM: artificial sequence
<220> FEATURE:
<223> OTHER INFORMATION: Synthetic primer

<400> SEQUENCE: 41
ctcacagagc tcagcgacag c                                              21

<210> SEQ ID NO 42
<211> LENGTH: 25
<212> TYPE: DNA
<213> ORGANISM: artificial sequence
<220> FEATURE:
<223> OTHER INFORMATION: Synthetic primer

<400> SEQUENCE: 42
aaattctgca ggccttgtag ttctc                                          25

<210> SEQ ID NO 43
<211> LENGTH: 24
<212> TYPE: DNA
<213> ORGANISM: artificial sequence
<220> FEATURE:
<223> OTHER INFORMATION: Synthetic primer

<400> SEQUENCE: 43
tgagagaccg acatttggac caga                                           24

<210> SEQ ID NO 44
<211> LENGTH: 24
<212> TYPE: DNA
<213> ORGANISM: artificial sequence
<220> FEATURE:
<223> OTHER INFORMATION: Synthetic primer

<400> SEQUENCE: 44
aacacgttta aggtctcct gggc                                            24

<210> SEQ ID NO 45
<211> LENGTH: 21
<212> TYPE: DNA
<213> ORGANISM: artificial sequence
<220> FEATURE:
<223> OTHER INFORMATION: Synthetic primer

<400> SEQUENCE: 45
tcaggctgag gcagacgata c                                              21

<210> SEQ ID NO 46
<211> LENGTH: 21
<212> TYPE: DNA
<213> ORGANISM: artificial sequence
<220> FEATURE:
<223> OTHER INFORMATION: Synthetic primer

<400> SEQUENCE: 46
cctcgcaact tccttagcac a                                              21

<210> SEQ ID NO 47
<211> LENGTH: 22
```

```
<212> TYPE: DNA
<213> ORGANISM: artificial sequence
<220> FEATURE:
<223> OTHER INFORMATION: Synthetic primer

<400> SEQUENCE: 47
tggaccatgg gggagttgga cc                                           22

<210> SEQ ID NO 48
<211> LENGTH: 23
<212> TYPE: DNA
<213> ORGANISM: artificial sequence
<220> FEATURE:
<223> OTHER INFORMATION: Synthetic primer

<400> SEQUENCE: 48 agccccctttt accaagtacc cga                                         23

<210> SEQ ID NO 49
<211> LENGTH: 23
<212> TYPE: DNA
<213> ORGANISM: artificial sequence
<220> FEATURE:
<223> OTHER INFORMATION: Synthetic primer

<400> SEQUENCE: 49
cgcaaacgct tctccctgaa gcc                                          23

<210> SEQ ID NO 50
<211> LENGTH: 22
<212> TYPE: DNA
<213> ORGANISM: artificial sequence
<220> FEATURE:
<223> OTHER INFORMATION: Synthetic primer

<400> SEQUENCE: 50
ttttccacca gcagggcagg gt                                           22

<210> SEQ ID NO 51
<211> LENGTH: 30
<212> TYPE: DNA
<213> ORGANISM: artificial sequence
<220> FEATURE:
<223> OTHER INFORMATION: Synthetic primer

<400> SEQUENCE: 51
catcagctcg agatctcagg accttggtgg                                   30

<210> SEQ ID NO 52
<211> LENGTH: 35
<212> TYPE: DNA
<213> ORGANISM: artificial sequence
<220> FEATURE:
<223> OTHER INFORMATION: Synthetic primer

<400> SEQUENCE: 52
cggatcgcgg ccgcagaaca caacatcaga ccatt                             35

<210> SEQ ID NO 53
<211> LENGTH: 37
<212> TYPE: DNA
<213> ORGANISM: artificial sequence
<220> FEATURE:
<223> OTHER INFORMATION: Synthetic primer

<400> SEQUENCE: 53
```
catcagctcg agctgggaag cgtgctaacg ataaaga     37

<210> SEQ ID NO 54
<211> LENGTH: 41
<212> TYPE: DNA
<213> ORGANISM: artificial sequence
<220> FEATURE:
<223> OTHER INFORMATION: Synthetic primer

<400> SEQUENCE: 54
cggatcgcgg ccgcacaaag tgaatctgtg gatgtatgcc c     41

<210> SEQ ID NO 55
<211> LENGTH: 32
<212> TYPE: DNA
<213> ORGANISM: artificial sequence
<220> FEATURE:
<223> OTHER INFORMATION: Synthetic primer

<400> SEQUENCE: 55
catcagctcg agcagagcaa tgcttttaat ga     32

<210> SEQ ID NO 56
<211> LENGTH: 35
<212> TYPE: DNA
<213> ORGANISM: artificial sequence
<220> FEATURE:
<223> OTHER INFORMATION: Synthetic primer

<400> SEQUENCE: 56
cggatcgcgg ccgctttaca ttcattcaat ccgaa     35

<210> SEQ ID NO 57
<211> LENGTH: 20
<212> TYPE: DNA
<213> ORGANISM: artificial sequence
<220> FEATURE:
<223> OTHER INFORMATION: Synthetic primer

<400> SEQUENCE: 57
taagaagttc cctaacaccg     20

<210> SEQ ID NO 58
<211> LENGTH: 22
<212> TYPE: DNA
<213> ORGANISM: artificial sequence
<220> FEATURE:
<223> OTHER INFORMATION: Synthetic primer

<400> SEQUENCE: 58
cgaggtccga agactcattt ag     22

<210> SEQ ID NO 59
<211> LENGTH: 23
<212> TYPE: RNA
<213> ORGANISM: Artificial sequence
<220> FEATURE:
<223> OTHER INFORMATION: Synthetic oligonucleotide

<400> SEQUENCE: 59
aaguucauga ucuacccaug aaa     23

<210> SEQ ID NO 60
<211> LENGTH: 22
<212> TYPE: RNA
<213> ORGANISM: Homo sapiens -continued

<400> SEQUENCE: 60
ucggauagga ccuaaugaac uu 22

<210> SEQ ID NO 61
<211> LENGTH: 39
<212> TYPE: RNA
<213> ORGANISM: Homo sapiens

<400> SEQUENCE: 61
ugaauuuaua aaguacccau cuaguacuug aaaaaguaa 39

<210> SEQ ID NO 62
<211> LENGTH: 39
<212> TYPE: RNA
<213> ORGANISM: Pan troglodytes

<400> SEQUENCE: 62
ugaauuuaua aaguacccau cuaguacuug aaaaaguaa 39

<210> SEQ ID NO 63
<211> LENGTH: 39
<212> TYPE: RNA
<213> ORGANISM: Mycoplasma mycoides

<400> SEQUENCE: 63
ugaauuuaua aaguacucau cuaguacuug aaaaaguaa 39

<210> SEQ ID NO 64
<211> LENGTH: 38
<212> TYPE: RNA
<213> ORGANISM: Mus musculus

<400> SEQUENCE: 64
ugaauuuaua aguacccaug uaguacuuga aagucaag 38

<210> SEQ ID NO 65
<211> LENGTH: 38
<212> TYPE: RNA
<213> ORGANISM: Rattus norvegicus

<400> SEQUENCE: 65
ugaaucuuua aguacccaug uaguacuuga aaaucaag 38

<210> SEQ ID NO 66
<211> LENGTH: 38
<212> TYPE: RNA
<213> ORGANISM: Coprothermobacter proteolyticus

<400> SEQUENCE: 66
ugaauuuaua aguacccauc uaguacuuga aaaacuaa 38

<210> SEQ ID NO 67
<211> LENGTH: 38
<212> TYPE: RNA
<213> ORGANISM: Staphylococcus aureus

<400> SEQUENCE: 67
ugaauuaaua aacuacccac cuaguacuug aaagcuaa 38

<210> SEQ ID NO 68
<211> LENGTH: 23
<212> TYPE: RNA

```
<213> ORGANISM: Artificial sequence
<220> FEATURE:
<223> OTHER INFORMATION: Synthetic oligonucleotide

<400> SEQUENCE: 68
aaguucaucu uguuaaaauu uag                                           23

<210> SEQ ID NO 69
<211> LENGTH: 42
<212> TYPE: RNA
<213> ORGANISM: Homo sapiens

<400> SEQUENCE: 69
cuaguuagga uauugauuua aaauuguucu acuugaagug gu                      42

<210> SEQ ID NO 70
<211> LENGTH: 45
<212> TYPE: RNA
<213> ORGANISM: Pan troglodytes

<400> SEQUENCE: 70
cuaguuagaa ggauauugau uuaaaauugu ucuacuugaa guggu                   45

<210> SEQ ID NO 71
<211> LENGTH: 45
<212> TYPE: RNA
<213> ORGANISM: Mycoplasma mycoides

<400> SEQUENCE: 71
cuaguuagaa ggauauugau uuaaaguugu ucuucuugaa guggu                   45

<210> SEQ ID NO 72
<211> LENGTH: 49
<212> TYPE: RNA
<213> ORGANISM: Mus musculus

<400> SEQUENCE: 72
uuaaguagga agaaguuuau uuggaauugu uauacauacu ugaaguugu               49

<210> SEQ ID NO 73
<211> LENGTH: 49
<212> TYPE: RNA
<213> ORGANISM: Rattus norvegicus

<400> SEQUENCE: 73
uuacguagga agaagcuuau uugaaguugu cguacguacu ugaaguugu               49

<210> SEQ ID NO 74
<211> LENGTH: 45
<212> TYPE: RNA
<213> ORGANISM: Coprothermobacter proteolyticus

<400> SEQUENCE: 74
uuaauuagaa ggcaauuaau uugaaguugc ucuacuugaa guugu                   45

<210> SEQ ID NO 75
<211> LENGTH: 42
<212> TYPE: RNA
<213> ORGANISM: Staphylococcus aureus

<400> SEQUENCE: 75
ucaauuagga ggaaauguau uugaaguucu acuugaagcu gu                      42
```

```
<210> SEQ ID NO 76
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 76
uaguuuauua ugucaguuga uu                                                  22

<210> SEQ ID NO 77
<211> LENGTH: 21
<212> TYPE: RNA
<213> ORGANISM: Homo sapiens

<400> SEQUENCE: 77
uggauaggac uuaaugaacu u                                                   21

<210> SEQ ID NO 78
<211> LENGTH: 17
<212> TYPE: RNA
<213> ORGANISM: Homo sapiens

<400> SEQUENCE: 78
guggacuuaa ugaacuu                                                        17
```